US007632862B2

(12) United States Patent
Peters et al.

(10) Patent No.: US 7,632,862 B2
(45) Date of Patent: Dec. 15, 2009

(54) PHARMACEUTICAL COMPOSITIONS THAT MODULATE HPTPBETA ACTIVITY

(75) Inventors: Kevin Gene Peters, Loveland, OH (US); Michael Glen Davis, Lebanon, OH (US)

(73) Assignee: Procter & Gamble Company, Cincinnati, OH (US)

(*) Notice: Subject to any disclaimer, the term of this patent is extended or adjusted under 35 U.S.C. 154(b) by 0 days.

(21) Appl. No.: 11/787,535

(22) Filed: Apr. 17, 2007

(65) Prior Publication Data

US 2008/0076764 A1 Mar. 27, 2008

Related U.S. Application Data

(62) Division of application No. 10/633,742, filed on Aug. 4, 2003, now Pat. No. 7,226,755.

(60) Provisional application No. 60/413,547, filed on Sep. 25, 2002.

(51) Int. Cl.
*A61K 31/27* (2006.01)
(52) U.S. Cl. .................................................. 514/478
(58) Field of Classification Search ........................ None
See application file for complete search history.

(56) References Cited

U.S. PATENT DOCUMENTS

| | | | |
|---|---|---|---|
| 4,673,641 A | 6/1987 | George et al. | |
| 5,424,398 A | 6/1995 | Middeldorp et al. | |
| 5,585,089 A | 12/1996 | Queen et al. | |
| 5,807,819 A | 9/1998 | Cheng et al. | |
| 5,994,128 A | 11/1999 | Fallaux et al. | |
| 6,033,908 A | 3/2000 | Bout et al. | |
| 6,342,219 B1 | 1/2002 | Thorpe et al. | |
| 6,589,758 B1 | 7/2003 | Zhu | |
| 6,596,722 B2 | 7/2003 | Moltzen et al. | |
| 7,226,755 B1 | 6/2007 | Peters et al. | |
| 7,507,568 B2 | 3/2009 | Evdokimov et al. | |
| 2004/0167183 A1* | 8/2004 | Klopfenstein et al. | 514/357 |
| 2007/0299116 A1 | 12/2007 | Gray | |
| 2008/0004267 A1 | 1/2008 | Gray | |
| 2008/0108631 A1 | 5/2008 | Gray | |

FOREIGN PATENT DOCUMENTS

| | | |
|---|---|---|
| WO | WO 00/65085 | 11/2000 |
| WO | WO 00/65088 | 11/2000 |
| WO | WO 02/26774 | 4/2002 |

OTHER PUBLICATIONS

Meadows; "Keeping Up With Drug Safety Information"; 2006; FDA Consumer magazine; http://www.fda.gov/fdac/features/2006/306_drugsafety.html, accessed Mar. 17, 2008.*
Saliba; "Heparin in the treatment of burns: a review"; May 2001; Burns 27(4): 349-358; full text edition, pp. 1-16.*
Suggitt et al.; "50 Years of Preclinical Anticancer Drug Screening: Empirical to Target-Driven Approaches"; 2005; Clinical Cancer Research; 11:971-981.*
Daar; "Perspective: Emerging Resistance Profiles of Newly Approved Antiretroviral Drugs"; 2008; Topics in HIV Medicine; 16(4): 110-6.*
U.S. Appl. No. 10/634,027, filed Aug. 4, 2003, Evdokimov et al.
Chanteau, S.H. et al., "Synthesis of Anthropomorphic Molecules: The NanoPutians," *J. Org. Chem.* 2003, vol. 68, pp. 8750-8766.
Fachinger, G., et al., "Functional Interaction of Vascular Endothelial-Protein-Tyrosine Phosphatase with the Angiopoietin Receptor Tic-2", Oncogene, 1999, vol. 18, pp. 5948-5953.
Gaits, F., et al., "Increase in Receptor-like Protein Tyrosine Phosphatase Activity and Expression Level on Density-Dependent Growth Arrest of Endothelial Cells", Biochem. J., 1995, vol. 311, pp. 97-103.
Harder, K.W., et al., "Characterization and Kinetic Analysis of the Intracellular Domain of Human Protein Tyrosine Phosphatase β (HPTPβ) Using Synthetic Phosphopeptides", Biochem. J., 1994, vol. 296, pp. 395-401.
Hopkins, S.C. et al., "Inhibitors of Kinesin Activity from Structure-Based Computer Screening," *Biochemistry*, 2000, vol. 39, pp. 2805-2814.
Huang et al., HCPTPA, a Protein tyrosine phosphotase that regulates vascular endothelial growth factor receptor-mediated signal transduction and biological activity, J. Biol. Chem. 1999, 53, 38183-38188.
Jones, G. et al., "Development and Validation of a Genetic Algorithm for Flexible Docking," *J. Mol. Biol.* 1997, vol. 267, pp. 727-748.
Krueger, N.X., et al., "Structural Diversity and Evolution of Human Receptor-Like Protein Tyrosine Phosphatases", The EMBRO J., 1990, vol. 9, No. 10, pp. 3241-3252.
Harder, K.W., et al., "Characterization and Kinetic Analysis of the Intracellular Domain of Human Protein Tyrosine Phosphatase β (HPTPβ) Using Synthetic Phosphopeptides", Biochem. J., 1994, vol. 296, pp. 395-401.
Rarey, M. et al., "A Fast Flexible Docking Method Using An Incremental Construction Algorithm," *J. Mol. Biol.*, 1996, vol. 261, pp. 470-489.
Skoichet, B.K. et al., "Lead Discovery Using Molecular Docking," *Chem. Biology*, 2002, vol. 6, pp. 439-446.
Stahl, M. et al., "Detailed Analysis of Scoring Functions for Virtual Screening," *J. Med. Chem.*, 2001, vol. 44, pp. 1035-1042.
Wang, Y. et al., "Expressions and Characterization of Wild Type, Truncated, and Mutant Forms of the Intracellular Region of the Receptor-Like Protein Tyrosine Phosphatase HPTPβ", The J. of Biological Chem., 1992, vol. 267, No. 23.
Wright, M.B. et al., "Protein-Tyrosine Phosphatases in the Vessel Wall Differential Expression After Acute Arterial Injury", Arterioscler Thromb Vasc., 2000, pp. 1189-1198.
Annex, "Growth Factor-Induced Therapeutic Angiogenesis in the Heart: Protein Therapy," *Cardiovascular Research*, 65(3):649-655 (2005).
Ardelt, "Estradiol Regulates Angiopoietin-1 mRNA Expression Through Estrogen Receptor-α in a Rodent Experimental," *Stroke*, 36:337-341 (2005).

(Continued)

*Primary Examiner*—Ardin Marschel
*Assistant Examiner*—Timothy P Thomas
(74) *Attorney, Agent, or Firm*—Ballard Spahr LLP

(57) ABSTRACT

HPTPbeta is useful as a target in screening agents effective for the treatment of angiogenesis mediated disorders.

4 Claims, 13 Drawing Sheets

OTHER PUBLICATIONS

Altschul et al., "Gapped Blast and PSI-Blast: A New Generation of Protein Database Search Programs," *Nucleic Acids Res.*, 25(27):3389-3402 (1997).

Auerbach et al., "Angiogenesis Assays: A Critical Overview," *Clinical Chemistry*, 49(1):32-40 (2003).

Barany et al., "Solid-phase Peptide Synthesis: A Silver Anniversary Report," *Int J. Peptide Protein Res.*, 30(6):705-739 (1987).

Bartlett et al., "Molecular Recognition in Chemical and Biological Problems; Cavet: A Program to Facilitate the Structure-Derived Design of Biologically Active Molecules," *Special Pub., Royal Chem. Soc.*, 78:182-196 (1989).

Bohm, "The Computer Program LUDI: A New Method for the De Novo Design of Enzyme Inhibitors," *J. Comuter-Aided. Molec. Design*, 6(1):61-78 (1992).

Bussolino et al., "Molecular Mechanisms of Blood Vessel Formation," *Trends Biochem Sci.* 22(7):251-256 (1997).

Carano et al., "Angiogenesis and Bone Repair," *Drug Discovery Today*, 8(21):980-989 (2003).

Carvalho et al., "The Role of Angiogenesis in a Murine Tibial Model of Distraction Osteogenesis," *Bone.* 34:849-861 (2004).

Cohen et al., "Molecular Modeling Software and Methods for Medicinal Chemistry," *J. Med. Chem.*, 33(3):883-894 (1990).

Flower, "Modelling G-Protein-Coupled Receptors for Drug Design," *Biochimica et Biophysica Acta*, 1422:207-234 (1999).

Folkman, "Tumor Angiogenesis," *The Molecular Basis of Cancer* (eds. Mendelsohn, J., Howley, P. M., Israel, M. A. & Liotta, L. A.) 10:206-232 (1995).

Goodford, "A Computational Procedure for Determining Energetically Favorable Binding Sites on Biologically Important Macromolecules," *J. Med. Chem.*, 28(7):849-57 (1985).

Goodsell et al., "Automated Docking of Substrates to Proteins by Simulated Annealing," *Proteins Struct. Funct. Genet.* 8:195-202 (1990).

Henikoff et al., "Amino Acid Substitution Matrices from Protein Blocks," *Proc. Natl. Acad. Sci. USA* 89:10915-10919 (1992).

Itoh et al., "Purification and Characterization of the Catalytic Domains of the Human Receptor-Linked Protein Tyrosine Phosphatases HPTPβ, Leukocyte Common Antigen (LCA), and Leukocyte Common Antigen-Related Molecule (LAR)," *Journal of Biological Chemistry*, 267(17):12356-12363 (1992).

Keen, "Radioligand Binding Methods for Membrane Preparations and Intact cells," *Methods in Molecular Biology*, 83:*Receptor Signal Transduction Protocols*, edited Humana Press Inc., Totoway N.J. (1997).

Kohler et al., "Continuous Cultures of Fused Cells Secreting Antibody of Predefined Specificity," *Nature*, 256:495-497 (1975).

Kugathasan et al, "Role of Angiopoietin-1 in Experimental and Human Pulmonary Arterial Hypertension," *Chest*, 128(6):633S-642S (2005).

Kuntz et al., "A Geometric Approach to Macromolecule—Ligand Interactions," *J. Mol. Biol.* 161:269-288 (1982).

Lin et al., "Inhibition of Tumor Angiogenesis Using a Soluble Receptor Establishes a Role for Tie2 in Pathologic Vascular Growth," *J. Clinical Invest.*, 100(8):2072-2078 (1997).

Ma et al., "RNase Protection Assay," *Methods*, 10(3):273-8 (1996).

Merrifield, "Solid Phase Peptide Synthesism. I. The Synthesis of a Tetrapeptide," *J. Am. Chem. Soc.*, 85:2149-2154 (1963).

Miranker et al., "Functionality Maps of Binding Sites: A Multiple Copy Simultaneous Search Method," *Proteins: Struc. Func. And Genectics*, 11(1):29-34 (1991).

Navaza, "*AMoRe*: An Automated Package for Molecular Replacement," *J. Acta Cryst.* A50:157-163 (1994).

Nguyen et al., "Cellular Interactions in Vascular Growth and Differentiation," *Int Rev. Cytol.*, 204:1-48 (2001).

Nishibata et al., "Automatic Creation of Drug Candidate Structures Based on Receptor Structure. Starting Point for Artificial Lead Generation," *Tetrahedron*, 47(43):8985-8990 (1991).

O'Reilly et al., "Angiostatin: a Novel Angiogenesis Inhibitor That Mediates the Suppression of Metastases by a Lewis Lung Carcinoma," *Cell*, 79(2):315-328 (1994).

O'Reilly et al., "Endostatin: An Endogenous Inhibitor of Angiogenesis and Tumor Growth," *Cell*, 88(2):277-285 (1997).

Riechmann et al., "Reshaping Human Antibodies for Therapy," *Nature*, 332:323-327 (1988).

Schoneberg et al., "Structural basis of G protein-coupled receptor function," *Molecular and Cellular Endocrinology*, 151:181-193 (1999).

Sexton, "Recent advances in our understanding of peptide hormone receptors and Ramps," *Current Opinion in Drug Discovery and Development*, 2(5):440-448 (1999).

Shiojima et al., "Disruption of Coordinated Cardiac Hypertrophy and Angiogenesis Contributes to the Transition to Heart Failure," *J. Clinical Invest.*, 115(8):2108-2118 (2005).

Siddiqui et al., "Combination of Angiopoietin-1 and Vascular Endothelial Growth Factor Gene Therapy Enhances Arteriogenesis in the Ischemic Myocardium," *Biochem. Biophys. Res. Comm.*, 310(3):1002-1009 (2003).

Simons, "Angiogenesis: Where Do We Stand Now?" *Circulation*, 111:1556-1566 (2005).

Simons et al., "Clinical Trials in Coronary Angiogenesis: Issues, Problems, Consensus," *Circulation*, 102:e73-e86 (2000).

Stetler-Stevenson, "The Role of Matrix Metalloproteinases in Tumor Invasion, Metastasis, and Angiogenesis," *Surg. Oncol. Clin. N. Am.*, 10(2):383-392 (2001).

Suri et al., "Increased Vascularization in Mice Overexpressing Angiopoietin-1," *Science*, 282:468-471 (1998).

Takahashi, "Adenoviral-delivered Angiopoietin-1 Reduces the Infarction and Attenuates the Progression of Cardiac Dysfunction in the Rat Model of Acute Myocardial Infarction," *Molecular Therapy*, 8(4):584-592 (2003).

Teischer et al., "Potentiation of Cytotoxic Cancer Therapies by TNP-470 Alone and with Other Anti-Angiogenic Agents," *Int J. Cancer*, 57(6)920-925 (1994).

Thurston et al., "Angiopoietin-1 Protects the Adult Vasculature Against Plasma Leakage," *Nature Medicine*, 6(4):460-463 (2000).

Thurston, "Complementary Actions of VEGF and Angiopoietin-1 on Blood Vessel Growth and Leakage," *J. Anat.*, 200(6):575-580 (2002).

Vailhe et al., "In vitro Models of Vasculogenesis and Angiogenesis," *Laboratory Investigation*, 81(4):439-452 (2001).

Weidner et al., "Tumor Angiogenesis and Metastasis—Correlation in Invasive Breast Carcinoma," *New Eng. J. Med.*, 324(1):1-8 (1991).

Whitaker et al., "Vascular Endothelial Growth Factor Receptor-2 and Neuropilin-1 Form a Receptor Complex That Is Responsible for the Differential Signaling Potency of VEGF$_{165}$ and VEGF$_{121}$," *Journal of Biological Chemistry*, 276(27):25520-25531 (2001).

Yancopoulos et al., "Vascular-Specific Growth Factors and Blood Vessel Formation," *Nature*, 407(6801):242-248 (2000).

Zhang et al., "Vascular Endothelial Growth Factor and Angopoietins in Focal Cerebral Ischemia," *Trends Cardio. Med.*, 12(2):62-66 (2002).

U.S. Appl. No. 11/823,086, filed Jun. 26, 2007, Gray, Restriction Requirement, Oct. 2, 2008.

U.S. Appl. No. 11/823,086, filed Jun. 26, 2007, Gray, Response to Restriction Requirement, Dec. 2, 2008.

U.S. Appl. No. 11/823,086, filed Jun. 26, 2007, Gray, Preliminary Amendment, Jan. 20, 2009.

U.S. Appl. No. 11/823,086, filed Jun. 26, 2007, Gray, Non-Final Office Action, Mar. 4, 2009.

U.S. Appl. No. 11/821,868, filed Jun. 26, 2007, Gray, Restriction Requirement, Mar. 27, 2008.

U.S. Appl. No. 11/821,868, filed Jun. 26, 2007, Gray, Response to Restriction Requirement, Jun. 26, 2008.

U.S. Appl. No. 11/821,868, filed Jun. 26, 2007, Gray, Non-Final Office Action, Oct. 2, 2008.

U.S. Appl. No. 11/821,868, filed Jun. 26, 2007, Gray, Amendment and Response to Office Action, Nov. 3, 2008.

U.S. Appl. No. 11/821,868, filed Jun. 26, 2007, Gray, Final Office Action, Jan. 9, 2009.

U.S. Appl. No. 11/821,868, filed Jun. 26, 2007, Gray, Amendment After Final Rejection, Mar. 9, 2009.

U.S. Appl. No. 11/821,868, filed Jun. 26, 2007, Gray, Notice of Allowance, Mar. 25, 2009.

U.S. Appl. No. 11/821,868, filed Jun. 26, 2007, Gray, Amendment After Final and Response to Office Action, Apr. 21, 2009.

U.S. Appl. No. 10/633,742, filed Aug. 4, 2003, Peters, Requirement for Restriction/Election, Feb. 9, 2006.

U.S. Appl. No. 10/633,742, filed Aug. 4, 2003, Peters, Response to Election / Restriction, Mar. 6, 2006.

U.S. Appl. No. 10/633,742, filed Aug. 4, 2003, Peters, Non-Final Rejection, May 1, 2006.

U.S. Appl. No. 10/633,742, filed Aug. 4, 2003, Amendment/Request Reconsideration After Non-Final Rejection, Oct. 31, 2006.

U.S. Appl. No. 10/633,742, filed Aug. 4, 2003, Peters, Supplemental Response or Supplemental Amendment, Jan. 19, 2007.

U.S. Appl. No. 10/633,742, filed Aug. 4, 2003, Peters, Notice of Allowance, Feb. 6, 2007.

U.S. Appl. No. 10/633,742, filed Aug. 4, 2003, Peters, Issue Notification, May 16, 2007.

U.S. Appl. No. 10/633,742, filed Aug. 4, 2003, Peters, Request for Certificate of Correction, Apr. 10, 2008.

U.S. Appl. No. 10/633,742, filed Aug. 4, 2003, Peters, Certificate of Correction—Post Issue Communication, Apr. 22, 2008.

U.S. Appl. No. 10/633,742, filed Aug. 4, 2003, Peters, Certificate of Correction—Post Issue Communication, May 20, 2008.

U.S. Appl. No. 10/634,027, filed Aug. 4, 2003, Evdokimov, Restriction Requirement, Jan. 19, 2006.

U.S. Appl. No. 10/634,027, filed Aug. 4, 2003, Evdokimov, Response to Restriction Requirement, Feb. 13, 2006.

U.S. Appl. No. 10/634,027, filed Aug. 4, 2003, Evdokimov, Non-Final Office Action, Apr. 13, 2006.

U.S. Appl. No. 10/634,027, filed Aug. 4, 2003, Evdokimov, Reply After 1st Office Action, Oct. 16, 2006.

U.S. Appl. No. 10/634,027, filed Aug. 4, 2003, Evdokimov, Final Office Action, Nov. 22, 2006.

U.S. Appl. No. 10/634,027, filed Aug. 4, 2003, Evdokimov, Amendment After Final Office Action, May 21, 2007.

U.S. Appl. No. 10/634,027, filed Aug. 4, 2003, Evdokimov, Non-Final Office Action, Jun. 12, 2007.

U.S. Appl. No. 10/634,027, filed Aug. 4, 2003, Evdokimov, Amendment in Response to Non-Final Office Action, Sep. 17, 2007.

U.S. Appl. No. 10/634,027, filed Aug. 4, 2003, Evdokimov, Final Office Action, Nov. 9, 2007.

U.S. Appl. No. 10/634,027, filed Aug. 4, 2003, Evdokimov, Amendment and Response to Final Office Action, May 8, 2008.

U.S. Appl. No. 10/634,027, filed Aug. 4, 2003, Evdokimov, Non-Final Office Action, Jun. 17, 2008.

U.S. Appl. No. 10/634,027, filed Aug. 4, 2003, Evdokimov, Amendment and Response to Non-Final Office Action, Sep. 16, 2008.

U.S. Appl. No. 10/634,027, filed Aug. 4, 2003, Evdokimov, Notice of Allowance, Jan. 14, 2009.

U.S. Appl. No. 10/634,027, filed Aug. 4, 2003, Evdokimov, Issue Notification, Mar. 4, 2009.

PCT/US2007/014822, filed Jun. 27, 2007, Akebia Pharmaceuticals, Written Opinion, Dec. 27, 2008.

PCT/US2007/014822, filed Jun. 27, 2007, Akebia Pharmaceuticals, International Search Report, Feb. 14, 2008.

PCT/US2007/014822, filed Jun. 27, 2007, Akebia Pharmaceuticals, International Preliminary Report on Patentability, Jan. 6, 2009.

PCT/US2007/014823, filed Jun. 27, 2007, Akebia Pharmaceuticals, International Search Report, Oct. 12, 2007.

PCT/US2007/014823, filed Jun. 27, 2007, Akebia Pharmaceuticals, Written Opinion, Oct. 12, 2007.

PCT/US2007/014823, filed Jun. 27, 2007, Akebia Pharmaceuticals, Response to Search Report and Amendment, Feb. 8, 2008.

PCT/US2007/014823, filed Jun. 27, 2007, Akebia Pharmaceuticals, International Preliminary Report on Patentability, Jan. 6, 2009.

PCT/US2007/014824, filed Jun. 27, 2007, Akebia Pharmaceuticals, Written Opinion, Nov. 12, 2007.

PCT/US2007/014824, filed Jun. 27, 2007, Akebia Pharmaceuticals, Response to Search Report and Amendment, Feb. 8, 2008.

PCT/US2007/014824, filed Jun. 27, 2007, Akebia Pharmaceuticals, International Search Report, Feb. 14, 2008.

PCT/US2007/014824, filed Jun. 27, 2007, Akebia Pharmaceuticals, International Preliminary Report on Patentability, Jan. 6, 2009.

* cited by examiner

SEQUENCE LISTING

```
<160> NUMBER OF SEQ ID NOS: 17

<210> SEQ ID NO 1
<211> LENGTH: 6075
<212> TYPE: DNA
<213> ORGANISM: Homo sapiens
<220> FEATURE:
<221> NAME/KEY: CDS
<222> LOCATION: (31)..(6024)

<400> SEQUENCE: 1
gtctcctctg gatcttaact actgagcgca atg ctg agc cat gga gcc ggg ttg       54
                                 Met Leu Ser His Gly Ala Gly Leu
                                   1               5 gcc ttg tgg atc aca ctg agc ctg ctg cag act gga ctg gcg gag cca      102
Ala Leu Trp Ile Thr Leu Ser Leu Leu Gln Thr Gly Leu Ala Glu Pro
 10              15                  20 gag aga tgt aac ttc acc ctg gcg gag tcc aag gcc tcc agc cat tct      150
Glu Arg Cys Asn Phe Thr Leu Ala Glu Ser Lys Ala Ser Ser His Ser
 25                  30                  35                  40 gtg tct atc cag tgg aga att ttg ggc tca ccc tgt aac ttt agc ctc      198
Val Ser Ile Gln Trp Arg Ile Leu Gly Ser Pro Cys Asn Phe Ser Leu
                 45                  50                  55 atc tat agc agt gac acc ctg ggg gcc gcg ttg tgc cct acc ttt cgg      246
Ile Tyr Ser Ser Asp Thr Leu Gly Ala Ala Leu Cys Pro Thr Phe Arg
             60                  65                  70 ata gac aac acc aca tac gga tgt aac ctt caa gat tta caa gca gga      294
Ile Asp Asn Thr Thr Tyr Gly Cys Asn Leu Gln Asp Leu Gln Ala Gly
         75                  80                  85 acc atc tat aac ttc aag att att tct ctg gat gaa gag aga act gtg      342
Thr Ile Tyr Asn Phe Lys Ile Ile Ser Leu Asp Glu Glu Arg Thr Val
     90                  95                 100 gtc ttg caa aca gat cct tta cct cct gct agg ttt gga gtc agt aaa      390
Val Leu Gln Thr Asp Pro Leu Pro Pro Ala Arg Phe Gly Val Ser Lys
105                 110                 115                 120 gag aag acg act tca acc ggc ttg cat gtt tgg tgg act cct tct tcc      438
Glu Lys Thr Thr Ser Thr Gly Leu His Val Trp Trp Thr Pro Ser Ser
                125                 130                 135 gga aaa gtc acc tca tat gag gtg caa tta ttt gat gaa aat aac caa      486
Gly Lys Val Thr Ser Tyr Glu Val Gln Leu Phe Asp Glu Asn Asn Gln
            140                 145                 150 aag ata cag ggg gtt caa att caa gaa agt act tca tgg aat gaa tac      534
Lys Ile Gln Gly Val Gln Ile Gln Glu Ser Thr Ser Trp Asn Glu Tyr
        155                 160                 165 act ttt ttc aat ctc act gct ggt agt aaa tac aat att gcc atc aca      582
Thr Phe Phe Asn Leu Thr Ala Gly Ser Lys Tyr Asn Ile Ala Ile Thr
    170                 175                 180 gct gtt tct gga gga aaa cgt tct ttt tca gtt tat acc aat gga tca      630
Ala Val Ser Gly Gly Lys Arg Ser Phe Ser Val Tyr Thr Asn Gly Ser
```

```
                                                              -continued
         185                 190                 195                 200
aca gtg cca tct cca gtg aaa gat att ggt att tcc aca aaa gcc aat         678
Thr Val Pro Ser Pro Val Lys Asp Ile Gly Ile Ser Thr Lys Ala Asn
                205                 210                 215 tct ctc ctg att tcc tgg tcc cat ggt tct ggg aat gtg gaa cga tac         726
Ser Leu Leu Ile Ser Trp Ser His Gly Ser Gly Asn Val Glu Arg Tyr
                220                 225                 230 cgg ctg atg cta atg gat aaa ggg atc cta gtt cat ggc ggt gtt gtg         774
Arg Leu Met Leu Met Asp Lys Gly Ile Leu Val His Gly Gly Val Val
                235                 240                 245 gac aaa cat gct act tcc tat gct ttt cac ggg ctg tcc cct ggc tac         822
Asp Lys His Ala Thr Ser Tyr Ala Phe His Gly Leu Ser Pro Gly Tyr
            250                 255                 260 ctc tac aac ctc act gtt atg act gag gct gca ggg ctg caa aac tac         870
Leu Tyr Asn Leu Thr Val Met Thr Glu Ala Ala Gly Leu Gln Asn Tyr
265                 270                 275                 280 agg tgg aaa cta gtc agg aca gcc ccc atg gaa gtc tca aat ctg aag         918
Arg Trp Lys Leu Val Arg Thr Ala Pro Met Glu Val Ser Asn Leu Lys
                285                 290                 295 gtg aca aat gat ggc agt ttg acc tct cta aaa gtc aaa tgg caa aga         966
Val Thr Asn Asp Gly Ser Leu Thr Ser Leu Lys Val Lys Trp Gln Arg
                300                 305                 310 cct cct gga aat gtg gat tct tac aat atc acc ctg tct cac aaa ggg        1014
Pro Pro Gly Asn Val Asp Ser Tyr Asn Ile Thr Leu Ser His Lys Gly
                315                 320                 325 acc atc aag gaa tcc aga gta tta gca cct tgg att act gaa act cac        1062
Thr Ile Lys Glu Ser Arg Val Leu Ala Pro Trp Ile Thr Glu Thr His
            330                 335                 340 ttt aaa gag tta gtc ccc ggt cga ctt tat caa gtt act gtc agc tgt        1110
Phe Lys Glu Leu Val Pro Gly Arg Leu Tyr Gln Val Thr Val Ser Cys
345                 350                 355                 360 gtc tct ggt gaa ctg tct gct cag aag atg gca gtg ggc aga aca ttt        1158
Val Ser Gly Glu Leu Ser Ala Gln Lys Met Ala Val Gly Arg Thr Phe
                365                 370                 375 cca gac aaa gtt gca aac ctg gag gca aac aat aat ggc agg atg agg        1206
Pro Asp Lys Val Ala Asn Leu Glu Ala Asn Asn Asn Gly Arg Met Arg
                380                 385                 390 tct ctt gta gtg agc tgg tcg ccc cct gct gga gac tgg gag cag tat        1254
Ser Leu Val Val Ser Trp Ser Pro Pro Ala Gly Asp Trp Glu Gln Tyr
                395                 400                 405 cgg atc cta ctc ttc aat gat tct gtg gtg ctg ctc aac atc act gtg        1302
Arg Ile Leu Leu Phe Asn Asp Ser Val Val Leu Leu Asn Ile Thr Val
        410                 415                 420 gga aag gaa gaa aca cag tat gtc atg gat gac acg ggg ctc gta ccg        1350
Gly Lys Glu Glu Thr Gln Tyr Val Met Asp Asp Thr Gly Leu Val Pro
425                 430                 435                 440 gga aga cag tat gag gtg gaa gtc att gtt gag agt gga aat ttg aag        1398
Gly Arg Gln Tyr Glu Val Glu Val Ile Val Glu Ser Gly Asn Leu Lys
                445                 450                 455 aat tct gag cgt tgc caa ggc agg aca gtc ccc ctg gct gtc ctc cag        1446
Asn Ser Glu Arg Cys Gln Gly Arg Thr Val Pro Leu Ala Val Leu Gln
                460                 465                 470 ctt cgt gtc aaa cat gcc aat gaa acc tca ctg agt atc atg tgg cag        1494
Leu Arg Val Lys His Ala Asn Glu Thr Ser Leu Ser Ile Met Trp Gln
            475                 480                 485 acc cct gta gca gaa tgg gag aaa tac atc att tcc cta gct gac aga        1542
Thr Pro Val Ala Glu Trp Glu Lys Tyr Ile Ile Ser Leu Ala Asp Arg
            490                 495                 500 gac ctc tta ctg atc cac aag tca ctc tcc aaa gat gcc aaa gaa ttc        1590
```

-continued

```
Asp Leu Leu Leu Ile His Lys Ser Leu Ser Lys Asp Ala Lys Glu Phe
505                 510                 515                 520 act ttt act gac ctg gtg cct gga cga aaa tac atg gct aca gtc acc    1638
Thr Phe Thr Asp Leu Val Pro Gly Arg Lys Tyr Met Ala Thr Val Thr
                    525                 530                 535 agt att agt gga gac tta aaa aat tcc tct tca gta aaa gga aga aca    1686
Ser Ile Ser Gly Asp Leu Lys Asn Ser Ser Ser Val Lys Gly Arg Thr
                540                 545                 550 gtg cct gcc caa gtg act gac ttg cat gtg gcc aac caa gga atg acc    1734
Val Pro Ala Gln Val Thr Asp Leu His Val Ala Asn Gln Gly Met Thr
            555                 560                 565 agt agt ctg ttt act aac tgg acc cag gca caa gga gac gta gaa ttt    1782
Ser Ser Leu Phe Thr Asn Trp Thr Gln Ala Gln Gly Asp Val Glu Phe
        570                 575                 580 tac caa gtc tta ctg atc cat gaa aat gtg gtc att aaa aat gaa agc    1830
Tyr Gln Val Leu Leu Ile His Glu Asn Val Val Ile Lys Asn Glu Ser
585                 590                 595                 600 atc tcc agt gag acc agc aga tac agc ttc cac tct ctc aag tcc ggc    1878
Ile Ser Ser Glu Thr Ser Arg Tyr Ser Phe His Ser Leu Lys Ser Gly
                    605                 610                 615 agc ctg tac tcc gtg gtg gta aca aca gtg agt gga ggg atc tct tcc    1926
Ser Leu Tyr Ser Val Val Val Thr Thr Val Ser Gly Gly Ile Ser Ser
                620                 625                 630 cga caa gtg gtt gtg gag gga aga aca gtc cct tcc agt gtg agt gga    1974
Arg Gln Val Val Val Glu Gly Arg Thr Val Pro Ser Ser Val Ser Gly
            635                 640                 645 gta acg gtg aac aat tcc ggt cgt aat gac tac ctc agc gtt tcc tgg    2022
Val Thr Val Asn Asn Ser Gly Arg Asn Asp Tyr Leu Ser Val Ser Trp
        650                 655                 660 ctc gtg gcg ccc gga gat gtg gat aac tat gag gta aca ttg tct cat    2070
Leu Val Ala Pro Gly Asp Val Asp Asn Tyr Glu Val Thr Leu Ser His
665                 670                 675                 680 gac ggc aag gtg gtt cag tcc ctt gtc att gcc aag tct gtc aga gaa    2118
Asp Gly Lys Val Val Gln Ser Leu Val Ile Ala Lys Ser Val Arg Glu
                    685                 690                 695 tgt tcc ttc agc tcc ctc acc cca ggc cgc ctc tac acc gtg acc ata    2166
Cys Ser Phe Ser Ser Leu Thr Pro Gly Arg Leu Tyr Thr Val Thr Ile
                700                 705                 710 act aca agg agt ggc aag tat gaa aat cac tcc ttc agc caa gag cgg    2214
Thr Thr Arg Ser Gly Lys Tyr Glu Asn His Ser Phe Ser Gln Glu Arg
            715                 720                 725 aca gtg cct gac aaa gtc cag gga gtc agt gtt agc aac tca gcc agg    2262
Thr Val Pro Asp Lys Val Gln Gly Val Ser Val Ser Asn Ser Ala Arg
        730                 735                 740 agt gac tat tta agg gta tcc tgg gtg cat gcc act gga gac ttt gat    2310
Ser Asp Tyr Leu Arg Val Ser Trp Val His Ala Thr Gly Asp Phe Asp
745                 750                 755                 760 cac tat gaa gtc acc att aaa aac aaa aac ttc att caa act aaa       2358
His Tyr Glu Val Thr Ile Lys Asn Lys Asn Asn Phe Ile Gln Thr Lys
                    765                 770                 775 agc att ccc aag tca gaa aac gaa tgt gta ttt gtt cag cta gtc cct   2406
Ser Ile Pro Lys Ser Glu Asn Glu Cys Val Phe Val Gln Leu Val Pro
                780                 785                 790 gga cgg ttg tac agt gtc act gtt act aca aaa agt gga caa tat gaa   2454
Gly Arg Leu Tyr Ser Val Thr Val Thr Thr Lys Ser Gly Gln Tyr Glu
            795                 800                 805 gcc aat gaa caa ggg aat ggg aga aca att cca gag cct gtt aag gat   2502
Ala Asn Glu Gln Gly Asn Gly Arg Thr Ile Pro Glu Pro Val Lys Asp
        810                 815                 820
```

```
cta aca ttg cgc aac agg agc act gag gac ttg cat gtg act tgg tca      2550
Leu Thr Leu Arg Asn Arg Ser Thr Glu Asp Leu His Val Thr Trp Ser
825             830             835             840 gga gct aat ggg gat gtc gac caa tat gag atc cag ctg ctc ttc aat      2598
Gly Ala Asn Gly Asp Val Asp Gln Tyr Glu Ile Gln Leu Leu Phe Asn
            845             850             855 gac atg aaa gta ttt cct cct ttt cac ctt gta aat acc gca acc gag      2646
Asp Met Lys Val Phe Pro Pro Phe His Leu Val Asn Thr Ala Thr Glu
        860             865             870 tat cga ttt act tcc cta aca cca ggc cgc caa tac aaa att ctt gtc      2694
Tyr Arg Phe Thr Ser Leu Thr Pro Gly Arg Gln Tyr Lys Ile Leu Val
    875             880             885 ttg acg att agc ggg gat gta cag cag tca gcc ttc att gag ggc ttc      2742
Leu Thr Ile Ser Gly Asp Val Gln Gln Ser Ala Phe Ile Glu Gly Phe
890             895             900 aca gtt cct agt gct gtc aaa aat att cac att tct ccc aat gga gca      2790
Thr Val Pro Ser Ala Val Lys Asn Ile His Ile Ser Pro Asn Gly Ala
905             910             915             920 aca gat agc ctg acg gtg aac tgg act cct ggt ggg gga gac gtt gat      2838
Thr Asp Ser Leu Thr Val Asn Trp Thr Pro Gly Gly Gly Asp Val Asp
            925             930             935 tcc tac acg gtg tcg gca ttc agg cac agt caa aag gtt gac tct cag      2886
Ser Tyr Thr Val Ser Ala Phe Arg His Ser Gln Lys Val Asp Ser Gln
        940             945             950 act att ccc aag cac gtc ttt gag cac acg ttc cac aga ctg gag gcc      2934
Thr Ile Pro Lys His Val Phe Glu His Thr Phe His Arg Leu Glu Ala
    955             960             965 ggg gag cag tac cag atc atg att gcc tca gtc agc ggg tcc ctg aag      2982
Gly Glu Gln Tyr Gln Ile Met Ile Ala Ser Val Ser Gly Ser Leu Lys
970             975             980 aat cag ata aat gtg gtt ggg cgg aca gtt cca gca tct gtc caa gga      3030
Asn Gln Ile Asn Val Val Gly Arg Thr Val Pro Ala Ser Val Gln Gly
985             990             995             1000 gta att gca gac aat gca tac agc agt tat tcc tta ata gta agt         3075
Val Ile Ala Asp Asn Ala Tyr Ser Ser Tyr Ser Leu Ile Val Ser
        1005            1010            1015 tgg caa aaa gct gct ggt gtg gca gaa aga tat gat atc ctg ctt         3120
Trp Gln Lys Ala Ala Gly Val Ala Glu Arg Tyr Asp Ile Leu Leu
        1020            1025            1030 cta act gaa aat gga atc ctt ctg cgc aac aca tca gag cca gcc         3165
Leu Thr Glu Asn Gly Ile Leu Leu Arg Asn Thr Ser Glu Pro Ala
        1035            1040            1045 acc act aag caa cac aaa ttt gaa gat cta aca cca ggc aag aaa         3210
Thr Thr Lys Gln His Lys Phe Glu Asp Leu Thr Pro Gly Lys Lys
        1050            1055            1060 tac aag ata cag atc cta act gtc agt gga ggc ctc ttt agc aag         3255
Tyr Lys Ile Gln Ile Leu Thr Val Ser Gly Gly Leu Phe Ser Lys
        1065            1070            1075 gaa gcc cag act gaa ggc cga aca gtc cca gca gct gtc acc gac         3300
Glu Ala Gln Thr Glu Gly Arg Thr Val Pro Ala Ala Val Thr Asp
        1080            1085            1090 ctg agg atc aca gag aac tcc acc agg cac ctg tcc ttc cgc tgg         3345
Leu Arg Ile Thr Glu Asn Ser Thr Arg His Leu Ser Phe Arg Trp
        1095            1100            1105 acc gcc tca gag ggg gag ctc agc tgg tac aac atc ttt ttg tac         3390
Thr Ala Ser Glu Gly Glu Leu Ser Trp Tyr Asn Ile Phe Leu Tyr
        1110            1115            1120 aac cca gat ggg aat ctc cag gag aga gct caa gtt gac cca cta         3435
Asn Pro Asp Gly Asn Leu Gln Glu Arg Ala Gln Val Asp Pro Leu
        1125            1130            1135
```

-continued

| | |
|---|---|
| gtc cag agc ttc tct ttc cag aac ttg cta caa ggc aga atg tac<br>Val Gln Ser Phe Ser Phe Gln Asn Leu Leu Gln Gly Arg Met Tyr<br>                  1140                             1145                            1150 | 3480 |
| aag atg gtg att gta act cac agt ggg gag ctg tct aat gag tct<br>Lys Met Val Ile Val Thr His Ser Gly Glu Leu Ser Asn Glu Ser<br>                  1155                             1160                            1165 | 3525 |
| ttc ata ttt ggt aga aca gtc cca gcc tct gtg agt cat ctc agg<br>Phe Ile Phe Gly Arg Thr Val Pro Ala Ser Val Ser His Leu Arg<br>                  1170                             1175                            1180 | 3570 |
| ggg tcc aat cgg aac acg aca gac agc ctt tgg ttc aac tgg agt<br>Gly Ser Asn Arg Asn Thr Thr Asp Ser Leu Trp Phe Asn Trp Ser<br>                  1185                             1190                            1195 | 3615 |
| cca gcc tct ggg gac ttt gac ttt tat gag ctg att ctc tat aat<br>Pro Ala Ser Gly Asp Phe Asp Phe Tyr Glu Leu Ile Leu Tyr Asn<br>                  1200                             1205                            1210 | 3660 |
| ccc aat ggc aca aag aag gaa aac tgg aaa gac aag gac ctg acg<br>Pro Asn Gly Thr Lys Lys Glu Asn Trp Lys Asp Lys Asp Leu Thr<br>                  1215                             1220                            1225 | 3705 |
| gag tgg cgg ttt caa ggc ctt gtt cct gga agg aag tac gtg ctg<br>Glu Trp Arg Phe Gln Gly Leu Val Pro Gly Arg Lys Tyr Val Leu<br>                  1230                             1235                            1240 | 3750 |
| tgg gtg gta act cac agt gga gat ctc agc aat aaa gtc aca gcg<br>Trp Val Val Thr His Ser Gly Asp Leu Ser Asn Lys Val Thr Ala<br>                  1245                             1250                            1255 | 3795 |
| gag agc aga aca gct cca agt cct ccc agt ctt atg tca ttt gct<br>Glu Ser Arg Thr Ala Pro Ser Pro Pro Ser Leu Met Ser Phe Ala<br>                  1260                             1265                            1270 | 3840 |
| gac att gca aac aca tcc ttg gcc atc acg tgg aaa ggg ccc cca<br>Asp Ile Ala Asn Thr Ser Leu Ala Ile Thr Trp Lys Gly Pro Pro<br>                  1275                             1280                            1285 | 3885 |
| gac tgg aca gac tac aac gac ttt gag ctg cag tgg ttg ccc aga<br>Asp Trp Thr Asp Tyr Asn Asp Phe Glu Leu Gln Trp Leu Pro Arg<br>                  1290                             1295                            1300 | 3930 |
| gat gca ctt act gtc ttc aac ccc tac aac aac aga aaa tca gaa<br>Asp Ala Leu Thr Val Phe Asn Pro Tyr Asn Asn Arg Lys Ser Glu<br>                  1305                             1310                            1315 | 3975 |
| gga cgc att gtg tat ggt ctt cgt cca ggg aga tcc tat caa ttc<br>Gly Arg Ile Val Tyr Gly Leu Arg Pro Gly Arg Ser Tyr Gln Phe<br>                  1320                             1325                            1330 | 4020 |
| aac gtc aag act gtc agt ggt gat tcc tgg aaa act tac agc aaa<br>Asn Val Lys Thr Val Ser Gly Asp Ser Trp Lys Thr Tyr Ser Lys<br>                  1335                             1340                            1345 | 4065 |
| cca att ttt gga tct gtg agg aca aag cct gac aag ata caa aac<br>Pro Ile Phe Gly Ser Val Arg Thr Lys Pro Asp Lys Ile Gln Asn<br>                  1350                             1355                            1360 | 4110 |
| ctg cat tgc cgg cct cag aac tcc acg gcc att gcc tgt tct tgg<br>Leu His Cys Arg Pro Gln Asn Ser Thr Ala Ile Ala Cys Ser Trp<br>                  1365                             1370                            1375 | 4155 |
| atc cct cct gat tct gac ttt gat ggt tat agt att gaa tgc cgg<br>Ile Pro Pro Asp Ser Asp Phe Asp Gly Tyr Ser Ile Glu Cys Arg<br>                  1380                             1385                            1390 | 4200 |
| aaa atg gac acc caa gaa gtt gag ttt tcc aga aag ctg gag aaa<br>Lys Met Asp Thr Gln Glu Val Glu Phe Ser Arg Lys Leu Glu Lys<br>                  1395                             1400                            1405 | 4245 |
| gaa aaa tct ctg ctc aac atc atg atg cta gtg ccc cat aag agg<br>Glu Lys Ser Leu Leu Asn Ile Met Met Leu Val Pro His Lys Arg<br>                  1410                             1415                            1420 | 4290 |
| tac ctg gtg tcc atc aaa gtg cag tcg gcc ggc atg acc agc gag<br>Tyr Leu Val Ser Ile Lys Val Gln Ser Ala Gly Met Thr Ser Glu | 4335 |

```
                 1425              1430                1435
gtg gtt gaa gac agc act atc aca atg ata gac cgc ccc cct cct     4380
Val Val Glu Asp Ser Thr Ile Thr Met Ile Asp Arg Pro Pro Pro
            1440                1445                1450 cca ccc cca cac att cgt gtg aat gaa aag gat gtg cta att agc     4425
Pro Pro Pro His Ile Arg Val Asn Glu Lys Asp Val Leu Ile Ser
            1455                1460                1465 aag tct tcc atc aac ttt act gtc aac tgc agc tgg ttc agc gac     4470
Lys Ser Ser Ile Asn Phe Thr Val Asn Cys Ser Trp Phe Ser Asp
            1470                1475                1480 acc aat gga gct gtg aaa tac ttc aca gtg gtg gtg aga gag gct     4515
Thr Asn Gly Ala Val Lys Tyr Phe Thr Val Val Val Arg Glu Ala
            1485                1490                1495 gat ggc agt gat gag ctg aag cca gaa cag cag cac cct ctc cct     4560
Asp Gly Ser Asp Glu Leu Lys Pro Glu Gln Gln His Pro Leu Pro
            1500                1505                1510 tcc tac ctg gag tac agg cac aat gcc tcc att cgg gtg tat cag     4605
Ser Tyr Leu Glu Tyr Arg His Asn Ala Ser Ile Arg Val Tyr Gln
            1515                1520                1525 act aat tat ttt gcc agc aaa tgt gcc gaa aat cct aac agc aac     4650
Thr Asn Tyr Phe Ala Ser Lys Cys Ala Glu Asn Pro Asn Ser Asn
            1530                1535                1540 tcc aag agt ttt aac att aag ctt gga gca gag atg gag agc tta     4695
Ser Lys Ser Phe Asn Ile Lys Leu Gly Ala Glu Met Glu Ser Leu
            1545                1550                1555 ggt gga aaa cgc gat ccc act cag caa aaa ttc tgt gat gga cca     4740
Gly Gly Lys Arg Asp Pro Thr Gln Gln Lys Phe Cys Asp Gly Pro
            1560                1565                1570 ctg aag cca cac act gcc tac aga atc agc att cga gct ttt aca     4785
Leu Lys Pro His Thr Ala Tyr Arg Ile Ser Ile Arg Ala Phe Thr
            1575                1580                1585 cag ctc ttt gat gag gac ctg aag gaa ttc aca aag cca ctc tat     4830
Gln Leu Phe Asp Glu Asp Leu Lys Glu Phe Thr Lys Pro Leu Tyr
            1590                1595                1600 tca gac aca ttt ttt tct tta ccc atc act act gaa tca gag ccc     4875
Ser Asp Thr Phe Phe Ser Leu Pro Ile Thr Thr Glu Ser Glu Pro
            1605                1610                1615 ttg ttt gga gct att gaa ggt gtg agt gct ggt ctg ttt tta att     4920
Leu Phe Gly Ala Ile Glu Gly Val Ser Ala Gly Leu Phe Leu Ile
            1620                1625                1630 ggc atg cta gtg gct gtt gtt gcc tta ttg atc tgc aga cag aaa     4965
Gly Met Leu Val Ala Val Val Ala Leu Leu Ile Cys Arg Gln Lys
            1635                1640                1645 gtg agc cat ggt cga gaa aga ccc tct gcc cgt ctg agc att cgt     5010
Val Ser His Gly Arg Glu Arg Pro Ser Ala Arg Leu Ser Ile Arg
            1650                1655                1660 agg gat cga cca tta tct gtc cac tta aac ctg ggc cag aaa ggt     5055
Arg Asp Arg Pro Leu Ser Val His Leu Asn Leu Gly Gln Lys Gly
            1665                1670                1675 aac cgg aaa act tct tgt cca ata aaa ata aat cag ttt gaa ggg     5100
Asn Arg Lys Thr Ser Cys Pro Ile Lys Ile Asn Gln Phe Glu Gly
            1680                1685                1690 cat ttc atg aag cta cag gct gac tcc aac tac ctt cta tcc aag     5145
His Phe Met Lys Leu Gln Ala Asp Ser Asn Tyr Leu Leu Ser Lys
            1695                1700                1705 gaa tac gag gag tta aaa gac gtg ggc cga aac cag tca tgt gac     5190
Glu Tyr Glu Glu Leu Lys Asp Val Gly Arg Asn Gln Ser Cys Asp
            1710                1715                1720 att gca ctc ttg ccg gag aat aga ggg aaa aat cga tac aac aat     5235
```

```
Ile Ala Leu Leu Pro Glu Asn Arg Gly Lys Asn Arg Tyr Asn Asn
            1725                1730                1735 ata ttg ccc tat gat gcc acg cga gtg aag ctc tcc aat gta gat         5280
Ile Leu Pro Tyr Asp Ala Thr Arg Val Lys Leu Ser Asn Val Asp
            1740                1745                1750 gat gat cct tgc tct gac tac atc aat gcc agc tac atc cct ggc         5325
Asp Asp Pro Cys Ser Asp Tyr Ile Asn Ala Ser Tyr Ile Pro Gly
            1755                1760                1765 aac aac ttc aga aga gaa tac att gtc act cag gga ccg ctt cct         5370
Asn Asn Phe Arg Arg Glu Tyr Ile Val Thr Gln Gly Pro Leu Pro
            1770                1775                1780 ggc acc aag gat gac ttc tgg aaa atg gtg tgg gaa caa aac gtt         5415
Gly Thr Lys Asp Asp Phe Trp Lys Met Val Trp Glu Gln Asn Val
            1785                1790                1795 cac aac atc gtc atg gtg acc cag tgt gtt gag aag ggc cga gta         5460
His Asn Ile Val Met Val Thr Gln Cys Val Glu Lys Gly Arg Val
            1800                1805                1810 aag tgt gac cat tac tgg cca gcg gac cag gat tcc ctc tac tat         5505
Lys Cys Asp His Tyr Trp Pro Ala Asp Gln Asp Ser Leu Tyr Tyr
            1815                1820                1825 ggg gac ctc atc ctg cag atg ctc tca gag tcc gtc ctg cct gag         5550
Gly Asp Leu Ile Leu Gln Met Leu Ser Glu Ser Val Leu Pro Glu
            1830                1835                1840 tgg acc atc cgg gag ttt aag ata tgc ggt gag gaa cag ctt gat         5595
Trp Thr Ile Arg Glu Phe Lys Ile Cys Gly Glu Glu Gln Leu Asp
            1845                1850                1855 gca cac aga ctc atc cgc cac ttt cac tat acg gtg tgg cca gac         5640
Ala His Arg Leu Ile Arg His Phe His Tyr Thr Val Trp Pro Asp
            1860                1865                1870 cat gga gtc cca gaa acc acc cag tct ctg atc cag ttt gtg aga         5685
His Gly Val Pro Glu Thr Thr Gln Ser Leu Ile Gln Phe Val Arg
            1875                1880                1885 act gtc agg gac tac atc aac aga agc ccg ggt gct ggg ccc act         5730
Thr Val Arg Asp Tyr Ile Asn Arg Ser Pro Gly Ala Gly Pro Thr
            1890                1895                1900 gtg gtg cac tgc agt gct ggt gtg ggt agg act gga acc ttt att         5775
Val Val His Cys Ser Ala Gly Val Gly Arg Thr Gly Thr Phe Ile
            1905                1910                1915 gca ttg gac cga atc ctc cag cag tta gac tcc aaa gac tct gtg         5820
Ala Leu Asp Arg Ile Leu Gln Gln Leu Asp Ser Lys Asp Ser Val
            1920                1925                1930 gac att tat gga gca gtg cac gac cta aga ctt cac agg gtt cac         5865
Asp Ile Tyr Gly Ala Val His Asp Leu Arg Leu His Arg Val His
            1935                1940                1945 atg gtc cag act gag tgt cag tat gtc tac cta cat cag tgt gta         5910
Met Val Gln Thr Glu Cys Gln Tyr Val Tyr Leu His Gln Cys Val
            1950                1955                1960 aga gat gtc ctc aga gca aga aag cta cgg agt gaa caa gaa aac         5955
Arg Asp Val Leu Arg Ala Arg Lys Leu Arg Ser Glu Gln Glu Asn
            1965                1970                1975 ccc ttg ttt cca atc tat gaa aat gtg aat cca gag tat cac aga         6000
Pro Leu Phe Pro Ile Tyr Glu Asn Val Asn Pro Glu Tyr His Arg
            1980                1985                1990 gat cca gtc tat tca agg cat tga gaatgtacct gaagagctcc tggataaaaa    6054
Asp Pro Val Tyr Ser Arg His
            1995 ttattcactg tgtgatttgt t                                             6075

<210> SEQ ID NO 2
```

<211> LENGTH: 1997
<212> TYPE: PRT
<213> ORGANISM: Homo sapiens

<400> SEQUENCE: 2

```
Met Leu Ser His Gly Ala Gly Leu Ala Leu Trp Ile Thr Leu Ser Leu
1               5                   10                  15

Leu Gln Thr Gly Leu Ala Glu Pro Glu Arg Cys Asn Phe Thr Leu Ala
            20                  25                  30

Glu Ser Lys Ala Ser Ser His Ser Val Ser Ile Gln Trp Arg Ile Leu
        35                  40                  45

Gly Ser Pro Cys Asn Phe Ser Leu Ile Tyr Ser Ser Asp Thr Leu Gly
    50                  55                  60

Ala Ala Leu Cys Pro Thr Phe Arg Ile Asp Asn Thr Thr Tyr Gly Cys
65                  70                  75                  80

Asn Leu Gln Asp Leu Gln Ala Gly Thr Ile Tyr Asn Phe Lys Ile Ile
                85                  90                  95

Ser Leu Asp Glu Glu Arg Thr Val Val Leu Gln Thr Asp Pro Leu Pro
            100                 105                 110

Pro Ala Arg Phe Gly Val Ser Lys Glu Lys Thr Thr Ser Thr Gly Leu
        115                 120                 125

His Val Trp Trp Thr Pro Ser Ser Gly Lys Val Thr Ser Tyr Glu Val
    130                 135                 140

Gln Leu Phe Asp Glu Asn Asn Gln Lys Ile Gln Gly Val Gln Ile Gln
145                 150                 155                 160

Glu Ser Thr Ser Trp Asn Glu Tyr Thr Phe Phe Asn Leu Thr Ala Gly
                165                 170                 175

Ser Lys Tyr Asn Ile Ala Ile Thr Ala Val Ser Gly Gly Lys Arg Ser
            180                 185                 190

Phe Ser Val Tyr Thr Asn Gly Ser Thr Val Pro Ser Pro Val Lys Asp
        195                 200                 205

Ile Gly Ile Ser Thr Lys Ala Asn Ser Leu Leu Ile Ser Trp Ser His
    210                 215                 220

Gly Ser Gly Asn Val Glu Arg Tyr Arg Leu Met Leu Met Asp Lys Gly
225                 230                 235                 240

Ile Leu Val His Gly Gly Val Val Asp Lys His Ala Thr Ser Tyr Ala
                245                 250                 255

Phe His Gly Leu Ser Pro Gly Tyr Leu Tyr Asn Leu Thr Val Met Thr
            260                 265                 270

Glu Ala Ala Gly Leu Gln Asn Tyr Arg Trp Lys Leu Val Arg Thr Ala
        275                 280                 285

Pro Met Glu Val Ser Asn Leu Lys Val Thr Asn Asp Gly Ser Leu Thr
    290                 295                 300

Ser Leu Lys Val Lys Trp Gln Arg Pro Pro Gly Asn Val Asp Ser Tyr
305                 310                 315                 320

Asn Ile Thr Leu Ser His Lys Gly Thr Ile Lys Glu Ser Arg Val Leu
                325                 330                 335

Ala Pro Trp Ile Thr Glu Thr His Phe Lys Glu Leu Val Pro Gly Arg
            340                 345                 350

Leu Tyr Gln Val Thr Val Ser Cys Val Ser Gly Glu Leu Ser Ala Gln
        355                 360                 365

Lys Met Ala Val Gly Arg Thr Phe Pro Asp Lys Val Ala Asn Leu Glu
    370                 375                 380

Ala Asn Asn Asn Gly Arg Met Arg Ser Leu Val Val Ser Trp Ser Pro
```

-continued

```
            385                 390                 395                 400

Pro Ala Gly Asp Trp Glu Gln Tyr Arg Ile Leu Leu Phe Asn Asp Ser
                        405                 410                 415

Val Val Leu Leu Asn Ile Thr Val Gly Lys Glu Glu Thr Gln Tyr Val
                        420                 425                 430

Met Asp Asp Thr Gly Leu Val Pro Gly Arg Gln Tyr Glu Val Glu Val
                        435                 440                 445

Ile Val Glu Ser Gly Asn Leu Lys Asn Ser Glu Arg Cys Gln Gly Arg
                        450                 455                 460

Thr Val Pro Leu Ala Val Leu Gln Leu Arg Val Lys His Ala Asn Glu
        465                 470                 475                 480

Thr Ser Leu Ser Ile Met Trp Gln Thr Pro Val Ala Glu Trp Glu Lys
                        485                 490                 495

Tyr Ile Ile Ser Leu Ala Asp Arg Asp Leu Leu Ile His Lys Ser
                        500                 505                 510

Leu Ser Lys Asp Ala Lys Glu Phe Thr Phe Thr Asp Leu Val Pro Gly
                        515                 520                 525

Arg Lys Tyr Met Ala Thr Val Thr Ser Ile Ser Gly Asp Leu Lys Asn
                        530                 535                 540

Ser Ser Ser Val Lys Gly Arg Thr Val Pro Ala Gln Val Thr Asp Leu
        545                 550                 555                 560

His Val Ala Asn Gln Gly Met Thr Ser Ser Leu Phe Thr Asn Trp Thr
                        565                 570                 575

Gln Ala Gln Gly Asp Val Glu Phe Tyr Gln Val Leu Leu Ile His Glu
                        580                 585                 590

Asn Val Val Ile Lys Asn Glu Ser Ile Ser Ser Glu Thr Ser Arg Tyr
                        595                 600                 605

Ser Phe His Ser Leu Lys Ser Gly Ser Leu Tyr Ser Val Val Val Thr
                        610                 615                 620

Thr Val Ser Gly Gly Ile Ser Ser Arg Gln Val Val Glu Gly Arg
        625                 630                 635                 640

Thr Val Pro Ser Ser Val Ser Gly Val Thr Val Asn Asn Ser Gly Arg
                        645                 650                 655

Asn Asp Tyr Leu Ser Val Ser Trp Leu Val Ala Pro Gly Asp Val Asp
                        660                 665                 670

Asn Tyr Glu Val Thr Leu Ser His Asp Gly Lys Val Val Gln Ser Leu
                        675                 680                 685

Val Ile Ala Lys Ser Val Arg Glu Cys Ser Phe Ser Ser Leu Thr Pro
                        690                 695                 700

Gly Arg Leu Tyr Thr Val Thr Ile Thr Thr Arg Ser Gly Lys Tyr Glu
        705                 710                 715                 720

Asn His Ser Phe Ser Gln Glu Arg Thr Val Pro Asp Lys Val Gln Gly
                        725                 730                 735

Val Ser Val Ser Asn Ser Ala Arg Ser Asp Tyr Leu Arg Val Ser Trp
                        740                 745                 750

Val His Ala Thr Gly Asp Phe Asp His Tyr Glu Val Thr Ile Lys Asn
                        755                 760                 765

Lys Asn Asn Phe Ile Gln Thr Lys Ser Ile Pro Lys Ser Glu Asn Glu
                        770                 775                 780

Cys Val Phe Val Gln Leu Val Pro Gly Arg Leu Tyr Ser Val Thr Val
        785                 790                 795                 800

Thr Thr Lys Ser Gly Gln Tyr Glu Ala Asn Glu Gln Gly Asn Gly Arg
                        805                 810                 815
```

-continued

```
Thr Ile Pro Glu Pro Val Lys Asp Leu Thr Leu Arg Asn Arg Ser Thr
            820                 825                 830

Glu Asp Leu His Val Thr Trp Ser Gly Ala Asn Gly Asp Val Asp Gln
            835                 840                 845

Tyr Glu Ile Gln Leu Leu Phe Asn Asp Met Lys Val Phe Pro Pro Phe
            850                 855                 860

His Leu Val Asn Thr Ala Thr Glu Tyr Arg Phe Thr Ser Leu Thr Pro
865                 870                 875                 880

Gly Arg Gln Tyr Lys Ile Leu Val Leu Thr Ile Ser Gly Asp Val Gln
                    885                 890                 895

Gln Ser Ala Phe Ile Glu Gly Phe Thr Val Pro Ser Ala Val Lys Asn
                900                 905                 910

Ile His Ile Ser Pro Asn Gly Ala Thr Asp Ser Leu Thr Val Asn Trp
                915                 920                 925

Thr Pro Gly Gly Gly Asp Val Asp Ser Tyr Thr Val Ser Ala Phe Arg
                930                 935                 940

His Ser Gln Lys Val Asp Ser Gln Thr Ile Pro Lys His Val Phe Glu
945                 950                 955                 960

His Thr Phe His Arg Leu Glu Ala Gly Glu Gln Tyr Gln Ile Met Ile
                    965                 970                 975

Ala Ser Val Ser Gly Ser Leu Lys Asn Gln Ile Asn Val Gly Arg
                980                 985                 990

Thr Val Pro Ala Ser Val Gln Gly  Val Ile Ala Asp Asn  Ala Tyr Ser
                995                 1000                1005

Ser Tyr  Ser Leu Ile Val Ser  Trp Gln Lys Ala Ala  Gly Val Ala
    1010                1015                1020

Glu Arg  Tyr Asp Ile Leu Leu  Leu Thr Glu Asn Gly  Ile Leu Leu
    1025                1030                1035

Arg Asn  Thr Ser Glu Pro Ala  Thr Thr Lys Gln His  Lys Phe Glu
    1040                1045                1050

Asp Leu  Thr Pro Gly Lys Lys  Tyr Lys Ile Gln Ile  Leu Thr Val
    1055                1060                1065

Ser Gly  Gly Leu Phe Ser Lys  Glu Ala Gln Thr Glu  Gly Arg Thr
    1070                1075                1080

Val Pro  Ala Ala Val Thr Asp  Leu Arg Ile Thr Glu  Asn Ser Thr
    1085                1090                1095

Arg His  Leu Ser Phe Arg Trp  Thr Ala Ser Glu Gly  Glu Leu Ser
    1100                1105                1110

Trp Tyr  Asn Ile Phe Leu Tyr  Asn Pro Asp Gly Asn  Leu Gln Glu
    1115                1120                1125

Arg Ala  Gln Val Asp Pro Leu  Val Gln Ser Phe Ser  Phe Gln Asn
    1130                1135                1140

Leu Leu  Gln Gly Arg Met Tyr  Lys Met Val Ile Val  Thr His Ser
    1145                1150                1155

Gly Glu  Leu Ser Asn Glu Ser  Phe Ile Phe Gly Arg  Thr Val Pro
    1160                1165                1170

Ala Ser  Val Ser His Leu Arg  Gly Ser Asn Arg Asn  Thr Thr Asp
    1175                1180                1185

Ser Leu  Trp Phe Asn Trp Ser  Pro Ala Ser Gly Asp  Phe Asp Phe
    1190                1195                1200

Tyr Glu  Leu Ile Leu Tyr Asn  Pro Asn Gly Thr Lys  Lys Glu Asn
    1205                1210                1215
```

-continued

```
Trp Lys Asp Lys Asp Leu Thr Glu Trp Arg Phe Gln Gly Leu Val
1220                1225                1230

Pro Gly Arg Lys Tyr Val Leu Trp Val Val Thr His Ser Gly Asp
    1235                1240                1245

Leu Ser Asn Lys Val Thr Ala Glu Ser Arg Thr Ala Pro Ser Pro
1250                1255                1260

Pro Ser Leu Met Ser Phe Ala Asp Ile Ala Asn Thr Ser Leu Ala
1265                1270                1275

Ile Thr Trp Lys Gly Pro Pro Asp Trp Thr Asp Tyr Asn Asp Phe
1280                1285                1290

Glu Leu Gln Trp Leu Pro Arg Asp Ala Leu Thr Val Phe Asn Pro
    1295                1300                1305

Tyr Asn Asn Arg Lys Ser Glu Gly Arg Ile Val Tyr Gly Leu Arg
1310                1315                1320

Pro Gly Arg Ser Tyr Gln Phe Asn Val Lys Thr Val Ser Gly Asp
1325                1330                1335

Ser Trp Lys Thr Tyr Ser Lys Pro Ile Phe Gly Ser Val Arg Thr
    1340                1345                1350

Lys Pro Asp Lys Ile Gln Asn Leu His Cys Arg Pro Gln Asn Ser
1355                1360                1365

Thr Ala Ile Ala Cys Ser Trp Ile Pro Pro Asp Ser Asp Phe Asp
1370                1375                1380

Gly Tyr Ser Ile Glu Cys Arg Lys Met Asp Thr Gln Glu Val Glu
1385                1390                1395

Phe Ser Arg Lys Leu Glu Lys Glu Lys Ser Leu Leu Asn Ile Met
    1400                1405                1410

Met Leu Val Pro His Lys Arg Tyr Leu Val Ser Ile Lys Val Gln
1415                1420                1425

Ser Ala Gly Met Thr Ser Glu Val Val Glu Asp Ser Thr Ile Thr
1430                1435                1440

Met Ile Asp Arg Pro Pro Pro Pro Pro His Ile Arg Val Asn
1445                1450                1455

Glu Lys Asp Val Leu Ile Ser Lys Ser Ser Ile Asn Phe Thr Val
    1460                1465                1470

Asn Cys Ser Trp Phe Ser Asp Thr Asn Gly Ala Val Lys Tyr Phe
1475                1480                1485

Thr Val Val Val Arg Glu Ala Asp Gly Ser Asp Glu Leu Lys Pro
    1490                1495                1500

Glu Gln Gln His Pro Leu Pro Ser Tyr Leu Glu Tyr Arg His Asn
1505                1510                1515

Ala Ser Ile Arg Val Tyr Gln Thr Asn Tyr Phe Ala Ser Lys Cys
1520                1525                1530

Ala Glu Asn Pro Asn Ser Asn Ser Lys Ser Phe Asn Ile Lys Leu
1535                1540                1545

Gly Ala Glu Met Glu Ser Leu Gly Gly Lys Arg Asp Pro Thr Gln
1550                1555                1560

Gln Lys Phe Cys Asp Gly Pro Leu Lys Pro His Thr Ala Tyr Arg
1565                1570                1575

Ile Ser Ile Arg Ala Phe Thr Gln Leu Phe Asp Glu Asp Leu Lys
1580                1585                1590

Glu Phe Thr Lys Pro Leu Tyr Ser Asp Thr Phe Phe Ser Leu Pro
    1595                1600                1605

Ile Thr Thr Glu Ser Glu Pro Leu Phe Gly Ala Ile Glu Gly Val
```

-continued

```
            1610                1615                1620

Ser Ala Gly Leu Phe Leu Ile Gly Met Leu Val Ala Val Val Ala
   1625                1630                1635

Leu Leu Ile Cys Arg Gln Lys Val Ser His Gly Arg Glu Arg Pro
   1640                1645                1650

Ser Ala Arg Leu Ser Ile Arg Arg Asp Arg Pro Leu Ser Val His
   1655                1660                1665

Leu Asn Leu Gly Gln Lys Gly Asn Arg Lys Thr Ser Cys Pro Ile
   1670                1675                1680

Lys Ile Asn Gln Phe Glu Gly His Phe Met Lys Leu Gln Ala Asp
   1685                1690                1695

Ser Asn Tyr Leu Leu Ser Lys Glu Tyr Glu Leu Lys Asp Val
   1700                1705                1710

Gly Arg Asn Gln Ser Cys Asp Ile Ala Leu Leu Pro Glu Asn Arg
   1715                1720                1725

Gly Lys Asn Arg Tyr Asn Asn Ile Leu Pro Tyr Asp Ala Thr Arg
   1730                1735                1740

Val Lys Leu Ser Asn Val Asp Asp Pro Cys Ser Asp Tyr Ile
   1745                1750                1755

Asn Ala Ser Tyr Ile Pro Gly Asn Asn Phe Arg Arg Glu Tyr Ile
   1760                1765                1770

Val Thr Gln Gly Pro Leu Pro Gly Thr Lys Asp Asp Phe Trp Lys
   1775                1780                1785

Met Val Trp Glu Gln Asn Val His Asn Ile Val Met Val Thr Gln
   1790                1795                1800

Cys Val Glu Lys Gly Arg Val Lys Cys Asp His Tyr Trp Pro Ala
   1805                1810                1815

Asp Gln Asp Ser Leu Tyr Tyr Gly Asp Leu Ile Leu Gln Met Leu
   1820                1825                1830

Ser Glu Ser Val Leu Pro Glu Trp Thr Ile Arg Glu Phe Lys Ile
   1835                1840                1845

Cys Gly Glu Glu Gln Leu Asp Ala His Arg Leu Ile Arg His Phe
   1850                1855                1860

His Tyr Thr Val Trp Pro Asp His Gly Val Pro Glu Thr Thr Gln
   1865                1870                1875

Ser Leu Ile Gln Phe Val Arg Thr Val Arg Asp Tyr Ile Asn Arg
   1880                1885                1890

Ser Pro Gly Ala Gly Pro Thr Val Val His Cys Ser Ala Gly Val
   1895                1900                1905

Gly Arg Thr Gly Thr Phe Ile Ala Leu Asp Arg Ile Leu Gln Gln
   1910                1915                1920

Leu Asp Ser Lys Asp Ser Val Asp Ile Tyr Gly Ala Val His Asp
   1925                1930                1935

Leu Arg Leu His Arg Val His Met Val Gln Thr Glu Cys Gln Tyr
   1940                1945                1950

Val Tyr Leu His Gln Cys Val Arg Asp Val Leu Arg Ala Arg Lys
   1955                1960                1965

Leu Arg Ser Glu Gln Glu Asn Pro Leu Phe Pro Ile Tyr Glu Asn
   1970                1975                1980

Val Asn Pro Glu Tyr His Arg Asp Pro Val Tyr Ser Arg His
   1985                1990                1995
```

<210> SEQ ID NO 3

<211> LENGTH: 1752
<212> TYPE: DNA
<213> ORGANISM: Mus musculus
<220> FEATURE:
<221> NAME/KEY: CDS
<222> LOCATION: (2)..(1750)

<400> SEQUENCE: 3

```
g tca agg aag agg tac ctg gtg tcc atc aag gtg cag tcg gcc ggc atg        49
  Ser Arg Lys Arg Tyr Leu Val Ser Ile Lys Val Gln Ser Ala Gly Met
  1               5                  10                  15 acc agt gag gtg gtt gaa gat agc acc atc acc atg ata gac cgc ccg          97
Thr Ser Glu Val Val Glu Asp Ser Thr Ile Thr Met Ile Asp Arg Pro
              20                  25                  30 cct caa ccg cct cca cac atc cgt gtg aat gaa aag gat gtg cta atc         145
Pro Gln Pro Pro Pro His Ile Arg Val Asn Glu Lys Asp Val Leu Ile
         35                  40                  45 agc aaa tct tcc atc aac ttt act gtc aac tgc agc tgg ttc agc gac         193
Ser Lys Ser Ser Ile Asn Phe Thr Val Asn Cys Ser Trp Phe Ser Asp
 50                  55                  60 acc aac gga gcg gtt ggg tac ttt gct gtg gtg gtg aga gag gcc gac         241
Thr Asn Gly Ala Val Gly Tyr Phe Ala Val Val Val Arg Glu Ala Asp
 65                  70                  75                  80 agc atg gat gag ttg aag cca gaa cag cag cac cct ctc cct tcc tac         289
Ser Met Asp Glu Leu Lys Pro Glu Gln Gln His Pro Leu Pro Ser Tyr
                 85                  90                  95 ctg gag tac aga cac aac gcc tcc atc cga gtc tac cag acc aat tat         337
Leu Glu Tyr Arg His Asn Ala Ser Ile Arg Val Tyr Gln Thr Asn Tyr
            100                 105                 110 ttt gcc agc aaa tgt gct gaa agt ccc gac agc agt tct aaa agt ttc         385
Phe Ala Ser Lys Cys Ala Glu Ser Pro Asp Ser Ser Ser Lys Ser Phe
        115                 120                 125 aac att aag ctt gga gca gag atg gac agc ctc ggt ggc aaa tgt gat         433
Asn Ile Lys Leu Gly Ala Glu Met Asp Ser Leu Gly Gly Lys Cys Asp
    130                 135                 140 ccc agt cag cag aaa ttc tgt gat gga ccg ctg ttg cca cac acc gcc         481
Pro Ser Gln Gln Lys Phe Cys Asp Gly Pro Leu Leu Pro His Thr Ala
145                 150                 155                 160 tac aga atc agc atc cgg gct ttt aca cag cta ttt gac gag gac ttg         529
Tyr Arg Ile Ser Ile Arg Ala Phe Thr Gln Leu Phe Asp Glu Asp Leu
                165                 170                 175 aaa gag ttc acc aaa cct ctc tac tcg gat acg ttc tct atg ccc             577
Lys Glu Phe Thr Lys Pro Leu Tyr Ser Asp Thr Phe Phe Ser Met Pro
            180                 185                 190 atc acc aca gag tca gag ccc ttg ttt gga gtt att gaa ggt gtg agt         625
Ile Thr Thr Glu Ser Glu Pro Leu Phe Gly Val Ile Glu Gly Val Ser
        195                 200                 205 gct ggc ctg ttt cta att ggc atg ctg gtg gcc ctt gtt gcc ttc ttc         673
Ala Gly Leu Phe Leu Ile Gly Met Leu Val Ala Leu Val Ala Phe Phe
    210                 215                 220 atc tgc aga cag aaa gct agc cac agc agg gaa agg cca tct gcc cgg         721
Ile Cys Arg Gln Lys Ala Ser His Ser Arg Glu Arg Pro Ser Ala Arg
225                 230                 235                 240 ctc agc att cgt agg gac cgg cct ttg tct gtc cat ctg aat ctg ggc         769
Leu Ser Ile Arg Arg Asp Arg Pro Leu Ser Val His Leu Asn Leu Gly
                245                 250                 255 cag aaa ggc aac cgg aaa act tct tgc ccc ata aag atc aat cag ttt         817
Gln Lys Gly Asn Arg Lys Thr Ser Cys Pro Ile Lys Ile Asn Gln Phe
            260                 265                 270 gaa ggg cat ttc atg aag ctg cag gca gac tcc aac tac ctt cta tcc         865
Glu Gly His Phe Met Lys Leu Gln Ala Asp Ser Asn Tyr Leu Leu Ser
```

```
                      275                 280                 285
aag gaa tat gag gac tta aaa gac gtg ggt aga agc cag tca tgt gac     913
Lys Glu Tyr Glu Asp Leu Lys Asp Val Gly Arg Ser Gln Ser Cys Asp
        290                 295                 300 att gcc ctc ttg cct gag aat cga ggg aaa aat cga tac aac aac ata     961
Ile Ala Leu Leu Pro Glu Asn Arg Gly Lys Asn Arg Tyr Asn Asn Ile
305                 310                 315                 320 ttg cct tat gat gcc tca aga gtg aag ctc tcg aat gtc gat gac gac    1009
Leu Pro Tyr Asp Ala Ser Arg Val Lys Leu Ser Asn Val Asp Asp Asp
                325                 330                 335 cct tgc tct gac tac atc aac gcc agc tac atc ccc ggt aac aac ttc    1057
Pro Cys Ser Asp Tyr Ile Asn Ala Ser Tyr Ile Pro Gly Asn Asn Phe
            340                 345                 350 aga cga gaa tac atc gcc act cag gga ccg ctt cca ggc acc aag gat    1105
Arg Arg Glu Tyr Ile Ala Thr Gln Gly Pro Leu Pro Gly Thr Lys Asp
        355                 360                 365 gac ttc tgg aag atg gcg tgg gag cag aac gtt cac aac atc gtc atg    1153
Asp Phe Trp Lys Met Ala Trp Glu Gln Asn Val His Asn Ile Val Met
370                 375                 380 gtg acc cag tgt gtt gaa aag ggc cga gtg aag tgt gac cat tac tgg    1201
Val Thr Gln Cys Val Glu Lys Gly Arg Val Lys Cys Asp His Tyr Trp
                385                 390                 395                 400 cca gca gac cag gac ccc ctc tac tac ggt gat ctc atc cta cag atg    1249
Pro Ala Asp Gln Asp Pro Leu Tyr Tyr Gly Asp Leu Ile Leu Gln Met
                405                 410                 415 gtc tcg gag tcc gtg ctc ccc gag tgg acc atc agg gag ttt aag ata    1297
Val Ser Glu Ser Val Leu Pro Glu Trp Thr Ile Arg Glu Phe Lys Ile
            420                 425                 430 tgc agt gaa gaa cag ttg gat gca cac aga ctc atc cgt cac ttt cac    1345
Cys Ser Glu Glu Gln Leu Asp Ala His Arg Leu Ile Arg His Phe His
        435                 440                 445 tac acg gtg tgg cca gac cat ggg gtc cca gag acc acc cag tcc ctg    1393
Tyr Thr Val Trp Pro Asp His Gly Val Pro Glu Thr Thr Gln Ser Leu
450                 455                 460 atc caa ttt gtg agg aca gtc agg gac tac atc aac aga agc ccc ggg    1441
Ile Gln Phe Val Arg Thr Val Arg Asp Tyr Ile Asn Arg Ser Pro Gly
465                 470                 475                 480 gct ggg ccc tcc gta gtg cac tgc agc gct ggt gtg ggc aga aca ggg    1489
Ala Gly Pro Ser Val Val His Cys Ser Ala Gly Val Gly Arg Thr Gly
                485                 490                 495 acg ttc gtt gcc ctg gac cgg atc ctc cag cag ttg gac tct aag gac    1537
Thr Phe Val Ala Leu Asp Arg Ile Leu Gln Gln Leu Asp Ser Lys Asp
            500                 505                 510 tcc gtg gac att tat ggg gca gtg cat gac cta aga ctc cac agg gtt    1585
Ser Val Asp Ile Tyr Gly Ala Val His Asp Leu Arg Leu His Arg Val
        515                 520                 525 cac atg gtc cag acc gag tgt caa tat gtg tat ctg cat cag tgt gta    1633
His Met Val Gln Thr Glu Cys Gln Tyr Val Tyr Leu His Gln Cys Val
530                 535                 540 aga gac gtc tca gag caa aga aac tgc gga aac gag caa gag aaa ggg    1681
Arg Asp Val Ser Glu Gln Arg Asn Cys Gly Asn Glu Gln Glu Lys Gly
545                 550                 555                 560 ggt gtt tcg att tat gag aat gtg aat cag agt atc aca gag atg caa    1729
Gly Val Ser Ile Tyr Glu Asn Val Asn Gln Ser Ile Thr Glu Met Gln
                565                 570                 575 tct act cga gac att aag aat tc                                      1752
Ser Thr Arg Asp Ile Lys Asn
            580
```

```
<210> SEQ ID NO 4
<211> LENGTH: 583
<212> TYPE: PRT
<213> ORGANISM: Mus musculus

<400> SEQUENCE: 4

Ser Arg Lys Arg Tyr Leu Val Ser Ile Lys Val Gln Ser Ala Gly Met
1               5                   10                  15

Thr Ser Glu Val Val Glu Asp Ser Thr Ile Thr Met Ile Asp Arg Pro
            20                  25                  30

Pro Gln Pro Pro Pro His Ile Arg Val Asn Glu Lys Asp Val Leu Ile
        35                  40                  45

Ser Lys Ser Ser Ile Asn Phe Thr Val Asn Cys Ser Trp Phe Ser Asp
    50                  55                  60

Thr Asn Gly Ala Val Gly Tyr Phe Ala Val Val Arg Glu Ala Asp
65                  70                  75                  80

Ser Met Asp Glu Leu Lys Pro Glu Gln Gln His Pro Leu Pro Ser Tyr
                85                  90                  95

Leu Glu Tyr Arg His Asn Ala Ser Ile Arg Val Tyr Gln Thr Asn Tyr
            100                 105                 110

Phe Ala Ser Lys Cys Ala Glu Ser Pro Asp Ser Ser Lys Ser Phe
        115                 120                 125

Asn Ile Lys Leu Gly Ala Glu Met Asp Ser Leu Gly Gly Lys Cys Asp
130                 135                 140

Pro Ser Gln Gln Lys Phe Cys Asp Gly Pro Leu Leu Pro His Thr Ala
145                 150                 155                 160

Tyr Arg Ile Ser Ile Arg Ala Phe Thr Gln Leu Phe Asp Glu Asp Leu
                165                 170                 175

Lys Glu Phe Thr Lys Pro Leu Tyr Ser Asp Thr Phe Phe Ser Met Pro
            180                 185                 190

Ile Thr Thr Glu Ser Glu Pro Leu Phe Gly Val Ile Glu Gly Val Ser
        195                 200                 205

Ala Gly Leu Phe Leu Ile Gly Met Leu Val Ala Leu Val Ala Phe Phe
210                 215                 220

Ile Cys Arg Gln Lys Ala Ser His Ser Arg Glu Arg Pro Ser Ala Arg
225                 230                 235                 240

Leu Ser Ile Arg Arg Asp Arg Pro Leu Ser Val His Leu Asn Leu Gly
                245                 250                 255

Gln Lys Gly Asn Arg Lys Thr Ser Cys Pro Ile Lys Ile Asn Gln Phe
            260                 265                 270

Glu Gly His Phe Met Lys Leu Gln Ala Asp Ser Asn Tyr Leu Leu Ser
        275                 280                 285

Lys Glu Tyr Glu Asp Leu Lys Asp Val Gly Arg Ser Gln Ser Cys Asp
290                 295                 300

Ile Ala Leu Leu Pro Glu Asn Arg Gly Lys Asn Arg Tyr Asn Asn Ile
305                 310                 315                 320

Leu Pro Tyr Asp Ala Ser Arg Val Lys Leu Ser Asn Val Asp Asp Asp
                325                 330                 335

Pro Cys Ser Asp Tyr Ile Asn Ala Ser Tyr Ile Pro Gly Asn Asn Phe
            340                 345                 350

Arg Arg Glu Tyr Ile Ala Thr Gln Gly Pro Leu Pro Gly Thr Lys Asp
        355                 360                 365

Asp Phe Trp Lys Met Ala Trp Glu Gln Asn Val His Asn Ile Val Met
370                 375                 380
```

```
Val Thr Gln Cys Val Glu Lys Gly Arg Val Lys Cys Asp His Tyr Trp
385                 390                 395                 400

Pro Ala Asp Gln Asp Pro Leu Tyr Tyr Gly Asp Leu Ile Leu Gln Met
            405                 410                 415

Val Ser Glu Ser Val Leu Pro Glu Trp Thr Ile Arg Glu Phe Lys Ile
        420                 425                 430

Cys Ser Glu Glu Gln Leu Asp Ala His Arg Leu Ile Arg His Phe His
    435                 440                 445

Tyr Thr Val Trp Pro Asp His Gly Val Pro Glu Thr Thr Gln Ser Leu
450                 455                 460

Ile Gln Phe Val Arg Thr Val Arg Asp Tyr Ile Asn Arg Ser Pro Gly
465                 470                 475                 480

Ala Gly Pro Ser Val His Cys Ser Ala Gly Val Gly Arg Thr Gly
            485                 490                 495

Thr Phe Val Ala Leu Asp Arg Ile Leu Gln Gln Leu Asp Ser Lys Asp
        500                 505                 510

Ser Val Asp Ile Tyr Gly Ala Val His Asp Leu Arg Leu His Arg Val
    515                 520                 525

His Met Val Gln Thr Glu Cys Gln Tyr Val Tyr Leu His Gln Cys Val
530                 535                 540

Arg Asp Val Ser Glu Gln Arg Asn Cys Gly Asn Glu Gln Lys Gly
545                 550                 555                 560

Gly Val Ser Ile Tyr Glu Asn Val Asn Gln Ser Ile Thr Glu Met Gln
            565                 570                 575

Ser Thr Arg Asp Ile Lys Asn
            580

<210> SEQ ID NO 5
<211> LENGTH: 4071
<212> TYPE: DNA
<213> ORGANISM: Homo sapiens
<220> FEATURE:
<221> NAME/KEY: CDS
<222> LOCATION: (1)..(4071)

<400> SEQUENCE: 5 atg gag agc aag gtg ctg ctg gcc gtc gcc ctg tgg ctc tgc gtg gag      48
Met Glu Ser Lys Val Leu Leu Ala Val Ala Leu Trp Leu Cys Val Glu
1               5                   10                  15 acc cgg gcc gcc tct gtg ggt ttg cct agt gtt tct ctt gat ctg ccc      96
Thr Arg Ala Ala Ser Val Gly Leu Pro Ser Val Ser Leu Asp Leu Pro
            20                  25                  30 agg ctc agc ata caa aaa gac ata ctt aca att aag gct aat aca act     144
Arg Leu Ser Ile Gln Lys Asp Ile Leu Thr Ile Lys Ala Asn Thr Thr
        35                  40                  45 ctt caa att act tgc agg gga cag agg gac ttg gac tgg ctt tgg ccc     192
Leu Gln Ile Thr Cys Arg Gly Gln Arg Asp Leu Asp Trp Leu Trp Pro
    50                  55                  60 aat aat cag agt ggc agt gag caa agg gtg gag gtg act gag tgc agc     240
Asn Asn Gln Ser Gly Ser Glu Gln Arg Val Glu Val Thr Glu Cys Ser
65                  70                  75                  80 gat ggc ctc ttc tgt aag aca ctc aca att cca aaa gtg atc gga aat     288
Asp Gly Leu Phe Cys Lys Thr Leu Thr Ile Pro Lys Val Ile Gly Asn
                85                  90                  95 gac act gga gcc tac aag tgc ttc tac cgg gaa act gac ttg gcc tcg     336
Asp Thr Gly Ala Tyr Lys Cys Phe Tyr Arg Glu Thr Asp Leu Ala Ser
            100                 105                 110 gtc att tat gtc tat gtt caa gat tac aga tct cca ttt att gct tct     384
```

```
Val Ile Tyr Val Tyr Val Gln Asp Tyr Arg Ser Pro Phe Ile Ala Ser
        115                 120                 125 gtt agt gac caa cat gga gtc gtg tac att act gag aac aaa aac aaa    432
Val Ser Asp Gln His Gly Val Val Tyr Ile Thr Glu Asn Lys Asn Lys
130                 135                 140 act gtg gtg att cca tgt ctc ggg tcc att tca aat ctc aac gtg tca    480
Thr Val Val Ile Pro Cys Leu Gly Ser Ile Ser Asn Leu Asn Val Ser
145                 150                 155                 160 ctt tgt gca aga tac cca gaa aag aga ttt gtt cct gat ggt aac aga    528
Leu Cys Ala Arg Tyr Pro Glu Lys Arg Phe Val Pro Asp Gly Asn Arg
                165                 170                 175 att tcc tgg gac agc aag aag ggc ttt act att ccc agc tac atg atc    576
Ile Ser Trp Asp Ser Lys Lys Gly Phe Thr Ile Pro Ser Tyr Met Ile
            180                 185                 190 agc tat gct ggc atg gtc ttc tgt gaa gca aaa att aat gat gaa agt    624
Ser Tyr Ala Gly Met Val Phe Cys Glu Ala Lys Ile Asn Asp Glu Ser
        195                 200                 205 tac cag tct att atg tac ata gtt gtc gtt gta ggg tat agg att tat    672
Tyr Gln Ser Ile Met Tyr Ile Val Val Val Val Gly Tyr Arg Ile Tyr
    210                 215                 220 gat gtg gtt ctg agt ccg tct cat gga att gaa cta tct gtt gga gaa    720
Asp Val Val Leu Ser Pro Ser His Gly Ile Glu Leu Ser Val Gly Glu
225                 230                 235                 240 aag ctt gtc tta aat tgt aca gca aga act gaa cta aat gtg ggg att    768
Lys Leu Val Leu Asn Cys Thr Ala Arg Thr Glu Leu Asn Val Gly Ile
                245                 250                 255 gac ttc aac tgg gaa tac cct tct tcg aag cat cag cat aag aaa ctt    816
Asp Phe Asn Trp Glu Tyr Pro Ser Ser Lys His Gln His Lys Lys Leu
            260                 265                 270 gta aac cga gac cta aaa acc cag tct ggg agt gag atg aag aaa ttt    864
Val Asn Arg Asp Leu Lys Thr Gln Ser Gly Ser Glu Met Lys Lys Phe
        275                 280                 285 ttg agc acc tta act ata gat ggt gta acc cgg agt gac caa gga ttg    912
Leu Ser Thr Leu Thr Ile Asp Gly Val Thr Arg Ser Asp Gln Gly Leu
    290                 295                 300 tac acc tgt gca gca tcc agt ggg ctg atg acc aag aag aac agc aca    960
Tyr Thr Cys Ala Ala Ser Ser Gly Leu Met Thr Lys Lys Asn Ser Thr
305                 310                 315                 320 ttt gtc agg gtc cat gaa aaa cct ttt gtt gct ttt gga agt ggc atg   1008
Phe Val Arg Val His Glu Lys Pro Phe Val Ala Phe Gly Ser Gly Met
                325                 330                 335 gaa tct ctg gtg gaa gcc acg gtg ggg gag cgt gtc aga atc cct gcg   1056
Glu Ser Leu Val Glu Ala Thr Val Gly Glu Arg Val Arg Ile Pro Ala
            340                 345                 350 aag tac ctt ggt tac cca ccc cca gaa ata aaa tgg tat aaa aat gga   1104
Lys Tyr Leu Gly Tyr Pro Pro Pro Glu Ile Lys Trp Tyr Lys Asn Gly
        355                 360                 365 ata ccc ctt gag tcc aat cac aca att aaa gcg ggg cat gta ctg acg   1152
Ile Pro Leu Glu Ser Asn His Thr Ile Lys Ala Gly His Val Leu Thr
    370                 375                 380 att atg gaa gta agt gaa aga gac aca gga aat tac act gtc atc ctt   1200
Ile Met Glu Val Ser Glu Arg Asp Thr Gly Asn Tyr Thr Val Ile Leu
385                 390                 395                 400 acc aat ccc att tca aag gag aag cag agc cat gtg gtc tct ctg gtt   1248
Thr Asn Pro Ile Ser Lys Glu Lys Gln Ser His Val Val Ser Leu Val
                405                 410                 415 gtg tat gtc cca ccc cag att ggt gag aaa tct cta atc tct cct gtg   1296
Val Tyr Val Pro Pro Gln Ile Gly Glu Lys Ser Leu Ile Ser Pro Val
            420                 425                 430
```

-continued

```
gat tcc tac cag tac ggc acc act caa acg ctg aca tgt acg gtc tat      1344
Asp Ser Tyr Gln Tyr Gly Thr Thr Gln Thr Leu Thr Cys Thr Val Tyr
        435                 440                 445 gcc att cct ccc ccg cat cac atc cac tgg tat tgg cag ttg gag gaa      1392
Ala Ile Pro Pro Pro His His Ile His Trp Tyr Trp Gln Leu Glu Glu
450                 455                 460 gag tgc gcc aac gag ccc agc caa gct gtc tca gtc aca aac cca tac      1440
Glu Cys Ala Asn Glu Pro Ser Gln Ala Val Ser Val Thr Asn Pro Tyr
465                 470                 475                 480 cct tgt gaa gaa tgg aga agt gtg gag gac ttc cag gga gga aat aaa      1488
Pro Cys Glu Glu Trp Arg Ser Val Glu Asp Phe Gln Gly Gly Asn Lys
                485                 490                 495 att gaa gtt aat aaa aat caa ttt gct cta att gaa gga aaa aac aaa      1536
Ile Glu Val Asn Lys Asn Gln Phe Ala Leu Ile Glu Gly Lys Asn Lys
            500                 505                 510 act gta agt acc ctt gtt atc caa gcg gca aat gtg tca gct ttg tac      1584
Thr Val Ser Thr Leu Val Ile Gln Ala Ala Asn Val Ser Ala Leu Tyr
        515                 520                 525 aaa tgt gaa gcg gtc aac aaa gtc ggg aga gga gag agg gtg atc tcc      1632
Lys Cys Glu Ala Val Asn Lys Val Gly Arg Gly Glu Arg Val Ile Ser
530                 535                 540 ttc cac gtg acc agg ggt cct gaa att act ttg caa cct gac atg cag      1680
Phe His Val Thr Arg Gly Pro Glu Ile Thr Leu Gln Pro Asp Met Gln
545                 550                 555                 560 ccc act gag cag gag agc gtg tct ttg tgg tgc act gca gac aga tct      1728
Pro Thr Glu Gln Glu Ser Val Ser Leu Trp Cys Thr Ala Asp Arg Ser
                565                 570                 575 acg ttt gag aac ctc aca tgg tac aag ctt ggc cca cag cct ctg cca      1776
Thr Phe Glu Asn Leu Thr Trp Tyr Lys Leu Gly Pro Gln Pro Leu Pro
            580                 585                 590 atc cat gtg gga gag ttg ccc aca cct gtt tgc aag aac ttg gat act      1824
Ile His Val Gly Glu Leu Pro Thr Pro Val Cys Lys Asn Leu Asp Thr
        595                 600                 605 ctt tgg aaa ttg aat gcc acc atg ttc tct aat agc aca aat gac att      1872
Leu Trp Lys Leu Asn Ala Thr Met Phe Ser Asn Ser Thr Asn Asp Ile
610                 615                 620 ttg atc atg gag ctt aag aat gca tcc ttg cag gac caa gga gac tat      1920
Leu Ile Met Glu Leu Lys Asn Ala Ser Leu Gln Asp Gln Gly Asp Tyr
625                 630                 635                 640 gtc tgc ctt gct caa gac agg aag acc aag aaa aga cat tgc gtg gtc      1968
Val Cys Leu Ala Gln Asp Arg Lys Thr Lys Lys Arg His Cys Val Val
                645                 650                 655 agg cag ctc aca gtc cta gag cgt gtg gca ccc acg atc aca gga aac      2016
Arg Gln Leu Thr Val Leu Glu Arg Val Ala Pro Thr Ile Thr Gly Asn
            660                 665                 670 ctg gag aat cag acg aca agt att ggg gaa agc atc gaa gtc tca tgc      2064
Leu Glu Asn Gln Thr Thr Ser Ile Gly Glu Ser Ile Glu Val Ser Cys
        675                 680                 685 acg gca tct ggg aat ccc cct cca cag atc atg tgg ttt aaa gat aat      2112
Thr Ala Ser Gly Asn Pro Pro Pro Gln Ile Met Trp Phe Lys Asp Asn
690                 695                 700 gag acc ctt gta gaa gac tca ggc att gta ttg aag gat ggg aac cgg      2160
Glu Thr Leu Val Glu Asp Ser Gly Ile Val Leu Lys Asp Gly Asn Arg
705                 710                 715                 720 aac ctc act atc cgc aga gtg agg aag gag gac gaa ggc ctc tac acc      2208
Asn Leu Thr Ile Arg Arg Val Arg Lys Glu Asp Glu Gly Leu Tyr Thr
                725                 730                 735 tgc cag gca tgc agt gtt ctt ggc tgt gca aaa gtg gag gca ttt ttc      2256
Cys Gln Ala Cys Ser Val Leu Gly Cys Ala Lys Val Glu Ala Phe Phe
            740                 745                 750
```

```
ata ata gaa ggt gcc cag gaa aag acg aac ttg gaa atc att att cta    2304
Ile Ile Glu Gly Ala Gln Glu Lys Thr Asn Leu Glu Ile Ile Ile Leu
        755                 760                 765 gta ggc acg gcg gtg att gcc atg ttc ttc tgg cta ctt ctt gtc atc    2352
Val Gly Thr Ala Val Ile Ala Met Phe Phe Trp Leu Leu Leu Val Ile
770                 775                 780 atc cta cgg acc gtt aag cgg gcc aat gga ggg gaa ctg aag aca ggc    2400
Ile Leu Arg Thr Val Lys Arg Ala Asn Gly Gly Glu Leu Lys Thr Gly
785                 790                 795                 800 tac ttg tcc atc gtc atg gat cca gat gaa ctc cca ttg gat gaa cat    2448
Tyr Leu Ser Ile Val Met Asp Pro Asp Glu Leu Pro Leu Asp Glu His
            805                 810                 815 tgt gaa cga ctg cct tat gat gcc agc aaa tgg gaa ttc ccc aga gac    2496
Cys Glu Arg Leu Pro Tyr Asp Ala Ser Lys Trp Glu Phe Pro Arg Asp
        820                 825                 830 cgg ctg aag cta ggt aag cct ctt ggc cgt ggt gcc ttt ggc caa gtg    2544
Arg Leu Lys Leu Gly Lys Pro Leu Gly Arg Gly Ala Phe Gly Gln Val
    835                 840                 845 att gaa gca gat gcc ttt gga att gac aag aca gca act tgc agg aca    2592
Ile Glu Ala Asp Ala Phe Gly Ile Asp Lys Thr Ala Thr Cys Arg Thr
850                 855                 860 gta gca gtc aaa atg ttg aaa gaa gga gca aca cac agt gag cat cga    2640
Val Ala Val Lys Met Leu Lys Glu Gly Ala Thr His Ser Glu His Arg
865                 870                 875                 880 gct ctc atg tct gaa ctc aag atc ctc att cat att ggt cac cat ctc    2688
Ala Leu Met Ser Glu Leu Lys Ile Leu Ile His Ile Gly His His Leu
            885                 890                 895 aat gtg gtc aac ctt cta ggt gcc tgt acc aag cca gga ggg cca ctc    2736
Asn Val Val Asn Leu Leu Gly Ala Cys Thr Lys Pro Gly Gly Pro Leu
        900                 905                 910 atg gtg att gtg gaa ttc tgc aaa ttt gga aac ctg tcc act tac ctg    2784
Met Val Ile Val Glu Phe Cys Lys Phe Gly Asn Leu Ser Thr Tyr Leu
    915                 920                 925 agg agc aag aga aat gaa ttt gtc ccc tac aag acc aaa ggg gca cga    2832
Arg Ser Lys Arg Asn Glu Phe Val Pro Tyr Lys Thr Lys Gly Ala Arg
930                 935                 940 ttc cgt caa ggg aaa gac tac gtt gga gca atc cct gtg gat ctg aaa    2880
Phe Arg Gln Gly Lys Asp Tyr Val Gly Ala Ile Pro Val Asp Leu Lys
945                 950                 955                 960 cgg cgc ttg gac agc atc acc agt agc cag agc tca gcc agc tct gga    2928
Arg Arg Leu Asp Ser Ile Thr Ser Ser Gln Ser Ser Ala Ser Ser Gly
            965                 970                 975 ttt gtg gag gag aag tcc ctc agt gat gta gaa gaa gag gaa gct cct    2976
Phe Val Glu Glu Lys Ser Leu Ser Asp Val Glu Glu Glu Glu Ala Pro
        980                 985                 990 gaa gat ctg tat aag gac ttc ctg acc ttg gag cat ctc atc tgt tac    3024
Glu Asp Leu Tyr Lys Asp Phe Leu Thr Leu Glu His Leu Ile Cys Tyr
    995                 1000                1005 agc ttc caa gtg gct aag ggc atg gag ttc ttg gca tcg cga aag        3069
Ser Phe Gln Val Ala Lys Gly Met Glu Phe Leu Ala Ser Arg Lys
    1010                1015                1020 tgt atc cac agg gac ctg gcg gca cga aat atc ctc tta tcg gag        3114
Cys Ile His Arg Asp Leu Ala Ala Arg Asn Ile Leu Leu Ser Glu
    1025                1030                1035 aag aac gtg gtt aaa atc tgt gac ttt ggc ttg gcc cgg gat att        3159
Lys Asn Val Val Lys Ile Cys Asp Phe Gly Leu Ala Arg Asp Ile
    1040                1045                1050 tat aaa gat cca gat tat gtc aga aaa gga gat gct cgc ctc cct        3204
Tyr Lys Asp Pro Asp Tyr Val Arg Lys Gly Asp Ala Arg Leu Pro
```

```
                                                                -continued
        1055                1060                1065
ttg  aaa  tgg  atg  gcc  cca  gaa  aca  att  ttt  gac  aga  gtg  tac  aca     3249
Leu  Lys  Trp  Met  Ala  Pro  Glu  Thr  Ile  Phe  Asp  Arg  Val  Tyr  Thr
     1070                1075                1080 atc  cag  agt  gac  gtc  tgg  tct  ttt  ggt  gtt  ttg  ctg  tgg  gaa  ata     3294
Ile  Gln  Ser  Asp  Val  Trp  Ser  Phe  Gly  Val  Leu  Leu  Trp  Glu  Ile
1085                1090                1095 ttt  tcc  tta  ggt  gct  tct  cca  tat  cct  ggg  gta  aag  att  gat  gaa     3339
Phe  Ser  Leu  Gly  Ala  Ser  Pro  Tyr  Pro  Gly  Val  Lys  Ile  Asp  Glu
     1100                1105                1110 gaa  ttt  tgt  agg  cga  ttg  aaa  gaa  gga  act  aga  atg  agg  gcc  cct     3384
Glu  Phe  Cys  Arg  Arg  Leu  Lys  Glu  Gly  Thr  Arg  Met  Arg  Ala  Pro
1115                1120                1125 gat  tat  act  aca  cca  gaa  atg  tac  cag  acc  atg  ctg  gac  tgc  tgg     3429
Asp  Tyr  Thr  Thr  Pro  Glu  Met  Tyr  Gln  Thr  Met  Leu  Asp  Cys  Trp
     1130                1135                1140 cac  ggg  gag  ccc  agt  cag  aga  ccc  acg  ttt  tca  gag  ttg  gtg  gaa     3474
His  Gly  Glu  Pro  Ser  Gln  Arg  Pro  Thr  Phe  Ser  Glu  Leu  Val  Glu
1145                1150                1155 cat  ttg  gga  aat  ctc  ttg  caa  gct  aat  gct  cag  cag  gat  ggc  aaa     3519
His  Leu  Gly  Asn  Leu  Leu  Gln  Ala  Asn  Ala  Gln  Gln  Asp  Gly  Lys
     1160                1165                1170 gac  tac  att  gtt  ctt  ccg  ata  tca  gag  act  ttg  agc  atg  gaa  gag     3564
Asp  Tyr  Ile  Val  Leu  Pro  Ile  Ser  Glu  Thr  Leu  Ser  Met  Glu  Glu
1175                1180                1185 gat  tct  gga  ctc  tct  ctg  cct  acc  tca  cct  gtt  tcc  tgt  atg  gag     3609
Asp  Ser  Gly  Leu  Ser  Leu  Pro  Thr  Ser  Pro  Val  Ser  Cys  Met  Glu
     1190                1195                1200 gag  gag  gaa  gta  tgt  gac  ccc  aaa  ttc  cat  tat  gac  aac  aca  gca     3654
Glu  Glu  Glu  Val  Cys  Asp  Pro  Lys  Phe  His  Tyr  Asp  Asn  Thr  Ala
1205                1210                1215 gga  atc  agt  cag  tat  ctg  cag  aac  agt  aag  cga  aag  agc  cgg  cct     3699
Gly  Ile  Ser  Gln  Tyr  Leu  Gln  Asn  Ser  Lys  Arg  Lys  Ser  Arg  Pro
     1220                1225                1230 gtg  agt  gta  aaa  aca  ttt  gaa  gat  atc  ccg  tta  gaa  gaa  cca  gaa     3744
Val  Ser  Val  Lys  Thr  Phe  Glu  Asp  Ile  Pro  Leu  Glu  Glu  Pro  Glu
1235                1240                1245 gta  aaa  gta  atc  cca  gat  gac  aac  cag  acg  gac  agt  ggt  atg  gtt     3789
Val  Lys  Val  Ile  Pro  Asp  Asp  Asn  Gln  Thr  Asp  Ser  Gly  Met  Val
     1250                1255                1260 ctt  gcc  tca  gaa  gag  ctg  aaa  act  ttg  gaa  gac  aga  acc  aaa  tta     3834
Leu  Ala  Ser  Glu  Glu  Leu  Lys  Thr  Leu  Glu  Asp  Arg  Thr  Lys  Leu
1265                1270                1275 tct  cca  tct  ttt  ggt  gga  atg  gtg  ccc  agc  aaa  agc  agg  gag  tct     3879
Ser  Pro  Ser  Phe  Gly  Gly  Met  Val  Pro  Ser  Lys  Ser  Arg  Glu  Ser
     1280                1285                1290 gtg  gca  tct  gaa  ggc  tca  aac  cag  aca  agc  ggc  tac  cag  tcc  gga     3924
Val  Ala  Ser  Glu  Gly  Ser  Asn  Gln  Thr  Ser  Gly  Tyr  Gln  Ser  Gly
1295                1300                1305 tat  cac  tcc  gat  gac  aca  gac  acc  acc  gtg  tac  tcc  agt  gag  gaa     3969
Tyr  His  Ser  Asp  Asp  Thr  Asp  Thr  Thr  Val  Tyr  Ser  Ser  Glu  Glu
     1310                1315                1320 gca  gaa  ctt  tta  aag  ctg  ata  gag  att  gga  gtg  caa  acc  ggt  agc     4014
Ala  Glu  Leu  Leu  Lys  Leu  Ile  Glu  Ile  Gly  Val  Gln  Thr  Gly  Ser
1325                1330                1335 aca  gcc  cag  att  ctc  cag  cct  gac  tcg  ggg  acc  aca  ctg  agc  tct     4059
Thr  Ala  Gln  Ile  Leu  Gln  Pro  Asp  Ser  Gly  Thr  Thr  Leu  Ser  Ser
     1340                1345                1350 cct  cct  gtt  taa                                                            4071
```

Pro Pro Val
    1355

<210> SEQ ID NO 6
<211> LENGTH: 1356
<212> TYPE: PRT
<213> ORGANISM: Homo sapiens

<400> SEQUENCE: 6

Met Glu Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
            20                  25                  30

Arg Leu Ser Ile Gln Lys Asp Ile Leu Thr Ile Lys Ala Asn Thr Thr
        35                  40                  45

Leu Gln Ile Thr Cys Arg Gly Gln Arg Asp Leu Asp Trp Leu Trp Pro
    50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Gly Tyr Arg Ile Tyr
    210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
            260                 265                 270

Val Asn Arg Asp Leu Lys Thr Gln Ser Gly Ser Glu Met Lys Lys Phe
        275                 280                 285

Leu Ser Thr Leu Thr Ile Asp Gly Val Thr Arg Ser Asp Gln Gly Leu
    290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
            340                 345                 350

Lys Tyr Leu Gly Tyr Pro Pro Pro Glu Ile Lys Trp Tyr Lys Asn Gly
        355                 360                 365

```
Ile Pro Leu Glu Ser Asn His Thr Ile Lys Ala Gly His Val Leu Thr
    370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
                405                 410                 415

Val Tyr Val Pro Pro Gln Ile Gly Glu Lys Ser Leu Ile Ser Pro Val
                420                 425                 430

Asp Ser Tyr Gln Tyr Gly Thr Thr Gln Thr Leu Thr Cys Thr Val Tyr
                435                 440                 445

Ala Ile Pro Pro His His Ile His Trp Tyr Trp Gln Leu Glu Glu
    450                 455                 460

Glu Cys Ala Asn Glu Pro Ser Gln Ala Val Ser Val Thr Asn Pro Tyr
465                 470                 475                 480

Pro Cys Glu Glu Trp Arg Ser Val Glu Asp Phe Gln Gly Gly Asn Lys
                485                 490                 495

Ile Glu Val Asn Lys Asn Gln Phe Ala Leu Ile Glu Gly Lys Asn Lys
                500                 505                 510

Thr Val Ser Thr Leu Val Ile Gln Ala Ala Asn Val Ser Ala Leu Tyr
                515                 520                 525

Lys Cys Glu Ala Val Asn Lys Val Gly Arg Gly Glu Arg Val Ile Ser
    530                 535                 540

Phe His Val Thr Arg Gly Pro Glu Ile Thr Leu Gln Pro Asp Met Gln
545                 550                 555                 560

Pro Thr Glu Gln Glu Ser Val Ser Leu Trp Cys Thr Ala Asp Arg Ser
                565                 570                 575

Thr Phe Glu Asn Leu Thr Trp Tyr Lys Leu Gly Pro Gln Pro Leu Pro
                580                 585                 590

Ile His Val Gly Glu Leu Pro Thr Pro Val Cys Lys Asn Leu Asp Thr
                595                 600                 605

Leu Trp Lys Leu Asn Ala Thr Met Phe Ser Asn Ser Thr Asn Asp Ile
    610                 615                 620

Leu Ile Met Glu Leu Lys Asn Ala Ser Leu Gln Asp Gln Gly Asp Tyr
625                 630                 635                 640

Val Cys Leu Ala Gln Asp Arg Lys Thr Lys Lys Arg His Cys Val Val
                645                 650                 655

Arg Gln Leu Thr Val Leu Glu Arg Val Ala Pro Thr Ile Thr Gly Asn
                660                 665                 670

Leu Glu Asn Gln Thr Thr Ser Ile Gly Glu Ser Ile Glu Val Ser Cys
                675                 680                 685

Thr Ala Ser Gly Asn Pro Pro Pro Gln Ile Met Trp Phe Lys Asp Asn
    690                 695                 700

Glu Thr Leu Val Glu Asp Ser Gly Ile Val Leu Lys Asp Gly Asn Arg
705                 710                 715                 720

Asn Leu Thr Ile Arg Arg Val Arg Lys Glu Asp Glu Gly Leu Tyr Thr
                725                 730                 735

Cys Gln Ala Cys Ser Val Leu Gly Cys Ala Lys Val Glu Ala Phe Phe
                740                 745                 750

Ile Ile Glu Gly Ala Gln Glu Lys Thr Asn Leu Glu Ile Ile Ile Leu
                755                 760                 765

Val Gly Thr Ala Val Ile Ala Met Phe Phe Trp Leu Leu Leu Val Ile
    770                 775                 780
```

```
Ile Leu Arg Thr Val Lys Arg Ala Asn Gly Gly Glu Leu Lys Thr Gly
785                 790                 795                 800

Tyr Leu Ser Ile Val Met Asp Pro Asp Glu Leu Pro Leu Asp Glu His
                805                 810                 815

Cys Glu Arg Leu Pro Tyr Asp Ala Ser Lys Trp Glu Phe Pro Arg Asp
            820                 825                 830

Arg Leu Lys Leu Gly Lys Pro Leu Gly Arg Gly Ala Phe Gly Gln Val
        835                 840                 845

Ile Glu Ala Asp Ala Phe Gly Ile Asp Lys Thr Ala Thr Cys Arg Thr
850                 855                 860

Val Ala Val Lys Met Leu Lys Glu Gly Ala Thr His Ser Glu His Arg
865                 870                 875                 880

Ala Leu Met Ser Glu Leu Lys Ile Leu Ile His Ile Gly His His Leu
                885                 890                 895

Asn Val Val Asn Leu Leu Gly Ala Cys Thr Lys Pro Gly Gly Pro Leu
            900                 905                 910

Met Val Ile Val Glu Phe Cys Lys Phe Gly Asn Leu Ser Thr Tyr Leu
        915                 920                 925

Arg Ser Lys Arg Asn Glu Phe Val Pro Tyr Lys Thr Lys Gly Ala Arg
930                 935                 940

Phe Arg Gln Gly Lys Asp Tyr Val Gly Ala Ile Pro Val Asp Leu Lys
945                 950                 955                 960

Arg Arg Leu Asp Ser Ile Thr Ser Ser Gln Ser Ser Ala Ser Ser Gly
            965                 970                 975

Phe Val Glu Glu Lys Ser Leu Ser Asp Val Glu Glu Glu Glu Ala Pro
        980                 985                 990

Glu Asp Leu Tyr Lys Asp Phe Leu Thr Leu Glu His Leu Ile Cys Tyr
        995                 1000                1005

Ser Phe Gln Val Ala Lys Gly Met Glu Phe Leu Ala Ser Arg Lys
    1010                1015                1020

Cys Ile His Arg Asp Leu Ala Ala Arg Asn Ile Leu Leu Ser Glu
    1025                1030                1035

Lys Asn Val Val Lys Ile Cys Asp Phe Gly Leu Ala Arg Asp Ile
    1040                1045                1050

Tyr Lys Asp Pro Asp Tyr Val Arg Lys Gly Asp Ala Arg Leu Pro
    1055                1060                1065

Leu Lys Trp Met Ala Pro Glu Thr Ile Phe Asp Arg Val Tyr Thr
    1070                1075                1080

Ile Gln Ser Asp Val Trp Ser Phe Gly Val Leu Leu Trp Glu Ile
    1085                1090                1095

Phe Ser Leu Gly Ala Ser Pro Tyr Pro Gly Val Lys Ile Asp Glu
    1100                1105                1110

Glu Phe Cys Arg Arg Leu Lys Glu Gly Thr Arg Met Arg Ala Pro
    1115                1120                1125

Asp Tyr Thr Thr Pro Glu Met Tyr Gln Thr Met Leu Asp Cys Trp
    1130                1135                1140

His Gly Glu Pro Ser Gln Arg Pro Thr Phe Ser Glu Leu Val Glu
    1145                1150                1155

His Leu Gly Asn Leu Leu Gln Ala Asn Ala Gln Gln Asp Gly Lys
    1160                1165                1170

Asp Tyr Ile Val Leu Pro Ile Ser Glu Thr Leu Ser Met Glu Glu
    1175                1180                1185

Asp Ser Gly Leu Ser Leu Pro Thr Ser Pro Val Ser Cys Met Glu
```

-continued

```
                1190                1195                 1200

Glu  Glu  Glu  Val  Cys  Asp  Pro  Lys  Phe  His  Tyr  Asp  Asn  Thr  Ala
     1205                1210                 1215

Gly  Ile  Ser  Gln  Tyr  Leu  Gln  Asn  Ser  Lys  Arg  Lys  Ser  Arg  Pro
     1220                1225                 1230

Val  Ser  Val  Lys  Thr  Phe  Glu  Asp  Ile  Pro  Leu  Glu  Glu  Pro  Glu
     1235                1240                 1245

Val  Lys  Val  Ile  Pro  Asp  Asp  Asn  Gln  Thr  Asp  Ser  Gly  Met  Val
     1250                1255                 1260

Leu  Ala  Ser  Glu  Glu  Leu  Lys  Thr  Leu  Glu  Asp  Arg  Thr  Lys  Leu
     1265                1270                 1275

Ser  Pro  Ser  Phe  Gly  Gly  Met  Val  Pro  Ser  Lys  Ser  Arg  Glu  Ser
     1280                1285                 1290

Val  Ala  Ser  Glu  Gly  Ser  Asn  Gln  Thr  Ser  Gly  Tyr  Gln  Ser  Gly
     1295                1300                 1305

Tyr  His  Ser  Asp  Asp  Thr  Asp  Thr  Thr  Val  Tyr  Ser  Ser  Glu  Glu
     1310                1315                 1320

Ala  Glu  Leu  Leu  Lys  Leu  Ile  Glu  Ile  Gly  Val  Gln  Thr  Gly  Ser
     1325                1330                 1335

Thr  Ala  Gln  Ile  Leu  Gln  Pro  Asp  Ser  Gly  Thr  Thr  Leu  Ser  Ser
     1340                1345                 1350

Pro  Pro  Val
     1355

<210> SEQ ID NO 7
<211> LENGTH: 4138
<212> TYPE: DNA
<213> ORGANISM: Homo sapiens
<220> FEATURE:
<221> NAME/KEY: CDS
<222> LOCATION: (149)..(3523)

<400> SEQUENCE: 7
cttctgtgct gttccttctt gcctctaact tgtaaacaag acgtactagg acgatgctaa      60
tggaaagtca caaccgctgg gttttttgaa aggatccttg ggacctcatg cacatttgtg     120
gaaactggat ggagagattt ggggaagc atg gac tct tta gcc agc tta gtt         172
                                Met Asp Ser Leu Ala Ser Leu Val
                                  1               5 ctc tgt gga gtc agc ttg ctc ctt tct gga act gtg gaa ggt gcc atg        220
Leu Cys Gly Val Ser Leu Leu Leu Ser Gly Thr Val Glu Gly Ala Met
 10               15                  20 gac ttg atc ttg atc aat tcc cta cct ctt gta tct gat gct gaa aca        268
Asp Leu Ile Leu Ile Asn Ser Leu Pro Leu Val Ser Asp Ala Glu Thr
25               30                  35                  40 tct ctc acc tgc att gcc tct ggg tgg cgc ccc cat gag ccc atc acc        316
Ser Leu Thr Cys Ile Ala Ser Gly Trp Arg Pro His Glu Pro Ile Thr
                     45                  50                  55 ata gga agg gac ttt gaa gcc tta atg aac cag cac cag gat ccg ctg        364
Ile Gly Arg Asp Phe Glu Ala Leu Met Asn Gln His Gln Asp Pro Leu
                 60                  65                  70 gaa gtt act caa gat gtg acc aga gaa tgg gct aaa aaa gtt gtt tgg        412
Glu Val Thr Gln Asp Val Thr Arg Glu Trp Ala Lys Lys Val Val Trp
             75                  80                  85 aag aga gaa aag gct agt aag atc aat ggt gct tat ttc tgt gaa ggg        460
Lys Arg Glu Lys Ala Ser Lys Ile Asn Gly Ala Tyr Phe Cys Glu Gly
         90                  95                  100 cga gtt cga gga gag gca atc agg ata cga acc atg aag atg cgt caa        508
```

```
                    -continued

Arg Val Arg Gly Glu Ala Ile Arg Ile Arg Thr Met Lys Met Arg Gln
105                 110                 115                 120 caa gct tcc ttc cta cca gct act tta act atg act gtg gac aag gga       556
Gln Ala Ser Phe Leu Pro Ala Thr Leu Thr Met Thr Val Asp Lys Gly
                125                 130                 135 gat aac gtg aac ata tct ttc aaa aag gta ttg att aaa gaa gaa gat       604
Asp Asn Val Asn Ile Ser Phe Lys Lys Val Leu Ile Lys Glu Glu Asp
        140                 145                 150 gca gtg att tac aaa aat ggt tcc ttc atc cat tca gtg ccc cgg cat       652
Ala Val Ile Tyr Lys Asn Gly Ser Phe Ile His Ser Val Pro Arg His
    155                 160                 165 gaa gta cct gat att cta gaa gta cac ctg cct cat gct cag ccc cag       700
Glu Val Pro Asp Ile Leu Glu Val His Leu Pro His Ala Gln Pro Gln
170                 175                 180 gat gct gga gtg tac tcg gcc agg tat ata gga gga aac ctc ttc acc       748
Asp Ala Gly Val Tyr Ser Ala Arg Tyr Ile Gly Gly Asn Leu Phe Thr
185                 190                 195                 200 tcg gcc ttc acc agg ctg ata gtc cgg aga tgt gaa gcc cag aag tgg       796
Ser Ala Phe Thr Arg Leu Ile Val Arg Arg Cys Glu Ala Gln Lys Trp
                205                 210                 215 gga cct gaa tgc aac cat ctc tgt act gct tgt atg aac aat ggt gtc       844
Gly Pro Glu Cys Asn His Leu Cys Thr Ala Cys Met Asn Asn Gly Val
        220                 225                 230 tgc cat gaa gat act gga gaa tgc att tgc cct cct ggg ttt atg gga       892
Cys His Glu Asp Thr Gly Glu Cys Ile Cys Pro Pro Gly Phe Met Gly
    235                 240                 245 agg acg tgt gag aag gct tgt gaa ctg cac acg ttt ggc aga act tgt       940
Arg Thr Cys Glu Lys Ala Cys Glu Leu His Thr Phe Gly Arg Thr Cys
250                 255                 260 aaa gaa agg tgc agt gga caa gag gga tgc aag tct tat gtg ttc tgt       988
Lys Glu Arg Cys Ser Gly Gln Glu Gly Cys Lys Ser Tyr Val Phe Cys
265                 270                 275                 280 ctc cct gac ccc tat ggg tgt tcc tgt gcc aca ggc tgg aag ggt ctg      1036
Leu Pro Asp Pro Tyr Gly Cys Ser Cys Ala Thr Gly Trp Lys Gly Leu
                285                 290                 295 cag tgc aat gaa gca tgc cac cct ggt ttt tac ggg cca gat tgt aag      1084
Gln Cys Asn Glu Ala Cys His Pro Gly Phe Tyr Gly Pro Asp Cys Lys
        300                 305                 310 ctt agg tgc agc tgc aac aat ggg gag atg tgt gat cgc ttc caa gga      1132
Leu Arg Cys Ser Cys Asn Asn Gly Glu Met Cys Asp Arg Phe Gln Gly
    315                 320                 325 tgt ctc tgc tct cca gga tgg cag ggg ctc cag tgt gag aga gaa ggc      1180
Cys Leu Cys Ser Pro Gly Trp Gln Gly Leu Gln Cys Glu Arg Glu Gly
330                 335                 340 ata ccg agg atg acc cca aag ata gtg gat ttg cca gat cat ata gaa      1228
Ile Pro Arg Met Thr Pro Lys Ile Val Asp Leu Pro Asp His Ile Glu
345                 350                 355                 360 gta aac agt ggt aaa ttt aat ccc att tgc aaa gct tct ggc tgg ccg      1276
Val Asn Ser Gly Lys Phe Asn Pro Ile Cys Lys Ala Ser Gly Trp Pro
                365                 370                 375 cta cct act aat gaa gaa atg acc ctg gtg aag ccg gat ggg aca gtg      1324
Leu Pro Thr Asn Glu Glu Met Thr Leu Val Lys Pro Asp Gly Thr Val
        380                 385                 390 ctc cat cca aaa gac ttt aac cat acg gat cat ttc tca gta gcc ata      1372
Leu His Pro Lys Asp Phe Asn His Thr Asp His Phe Ser Val Ala Ile
    395                 400                 405 ttc acc atc cac cgg atc ctc ccc cct gac tca gga gtt tgg gtc tgc      1420
Phe Thr Ile His Arg Ile Leu Pro Pro Asp Ser Gly Val Trp Val Cys
410                 415                 420
```

```
agt gtg aac aca gtg gct ggg atg gtg gaa aag ccc ttc aac att tct    1468
Ser Val Asn Thr Val Ala Gly Met Val Glu Lys Pro Phe Asn Ile Ser
425             430                 435                 440 gtt aaa gtt ctt cca aag ccc ctg aat gcc cca aac gtg att gac act    1516
Val Lys Val Leu Pro Lys Pro Leu Asn Ala Pro Asn Val Ile Asp Thr
        445                 450                 455 gga cat aac ttt gct gtc atc aac atc agc tct gag cct tac ttt ggg    1564
Gly His Asn Phe Ala Val Ile Asn Ile Ser Ser Glu Pro Tyr Phe Gly
                460                 465                 470 gat gga cca atc aaa tcc aag aag ctt cta tac aaa ccc gtt aat cac    1612
Asp Gly Pro Ile Lys Ser Lys Lys Leu Leu Tyr Lys Pro Val Asn His
            475                 480                 485 tat gag gct tgg caa cat att caa gtg aca aat gag att gtt aca ctc    1660
Tyr Glu Ala Trp Gln His Ile Gln Val Thr Asn Glu Ile Val Thr Leu
490                 495                 500 aac tat ttg gaa cct cgg aca gaa tat gaa ctc tgt gtg caa ctg gtc    1708
Asn Tyr Leu Glu Pro Arg Thr Glu Tyr Glu Leu Cys Val Gln Leu Val
505                 510                 515                 520 cgt cgt gga gag ggt ggg gaa ggg cat cct gga cct gtg aga cgc ttc    1756
Arg Arg Gly Glu Gly Gly Glu Gly His Pro Gly Pro Val Arg Arg Phe
                525                 530                 535 aca aca gct tct atc gga ctc cct cct cca aga ggt cta aat ctc ctg    1804
Thr Thr Ala Ser Ile Gly Leu Pro Pro Pro Arg Gly Leu Asn Leu Leu
            540                 545                 550 cct aaa agt cag acc act cta aat ttg acc tgg caa cca ata ttt cca    1852
Pro Lys Ser Gln Thr Thr Leu Asn Leu Thr Trp Gln Pro Ile Phe Pro
        555                 560                 565 agc tcg gaa gat gac ttt tat gtt gaa gtg gag aga agg tct gtg caa    1900
Ser Ser Glu Asp Asp Phe Tyr Val Glu Val Glu Arg Arg Ser Val Gln
    570                 575                 580 aaa agt gat cag cag aat att aaa gtt cca ggc aac ttg act tcg gtg    1948
Lys Ser Asp Gln Gln Asn Ile Lys Val Pro Gly Asn Leu Thr Ser Val
585                 590                 595                 600 cta ctt aac aac tta cat ccc agg gag cag tac gtg gtc cga gct aga    1996
Leu Leu Asn Asn Leu His Pro Arg Glu Gln Tyr Val Val Arg Ala Arg
                605                 610                 615 gtc aac acc aag gcc cag ggg gaa tgg agt gaa gat ctc act gct tgg    2044
Val Asn Thr Lys Ala Gln Gly Glu Trp Ser Glu Asp Leu Thr Ala Trp
            620                 625                 630 acc ctt agt gac att ctt cct cct caa cca gaa aac atc aag att tcc    2092
Thr Leu Ser Asp Ile Leu Pro Pro Gln Pro Glu Asn Ile Lys Ile Ser
        635                 640                 645 aac att aca cac tcc tcg gct gtg att tct tgg aca ata ttg gat ggc    2140
Asn Ile Thr His Ser Ser Ala Val Ile Ser Trp Thr Ile Leu Asp Gly
    650                 655                 660 tat tct att tct tct att act atc cgt tac aag gtt caa ggc aag aat    2188
Tyr Ser Ile Ser Ser Ile Thr Ile Arg Tyr Lys Val Gln Gly Lys Asn
665                 670                 675                 680 gaa gac cag cac gtt gat gtg aag ata aag aat gcc acc atc att cag    2236
Glu Asp Gln His Val Asp Val Lys Ile Lys Asn Ala Thr Ile Ile Gln
                685                 690                 695 tat cag ctc aag ggc cta gag cct gaa aca gca tac cag gtg gac att    2284
Tyr Gln Leu Lys Gly Leu Glu Pro Glu Thr Ala Tyr Gln Val Asp Ile
            700                 705                 710 ttt gca gag aac aac ata ggg tca agc aac cca gcc ttt tct cat gaa    2332
Phe Ala Glu Asn Asn Ile Gly Ser Ser Asn Pro Ala Phe Ser His Glu
        715                 720                 725 ctg gtg acc ctc cca gaa tct caa gca cca gcg gac ctc gga ggg ggg    2380
Leu Val Thr Leu Pro Glu Ser Gln Ala Pro Ala Asp Leu Gly Gly Gly
730                 735                 740
```

```
aag atg ctg ctt ata gcc atc ctt ggc tct gct gga atg acc tgc ctg    2428
Lys Met Leu Leu Ile Ala Ile Leu Gly Ser Ala Gly Met Thr Cys Leu
745                 750                 755                 760 act gtg ctg ttg gcc ttt ctg atc ata ttg caa ttg aag agg gca aat    2476
Thr Val Leu Leu Ala Phe Leu Ile Ile Leu Gln Leu Lys Arg Ala Asn
                765                 770                 775 gtg caa agg aga atg gcc caa gcc ttc caa aac gtg agg gaa gaa cca    2524
Val Gln Arg Arg Met Ala Gln Ala Phe Gln Asn Val Arg Glu Glu Pro
            780                 785                 790 gct gtg cag ttc aac tca ggg act ctg gcc cta aac agg aag gtc aaa    2572
Ala Val Gln Phe Asn Ser Gly Thr Leu Ala Leu Asn Arg Lys Val Lys
        795                 800                 805 aac aac cca gat cct aca att tat cca gtg ctt gac tgg aat gac atc    2620
Asn Asn Pro Asp Pro Thr Ile Tyr Pro Val Leu Asp Trp Asn Asp Ile
810                 815                 820 aaa ttt caa gat gtg att ggg gag ggc aat ttt ggc caa gtt ctt aag    2668
Lys Phe Gln Asp Val Ile Gly Glu Gly Asn Phe Gly Gln Val Leu Lys
825                 830                 835                 840 gcg cgc atc aag aag gat ggg tta cgg atg gat gct gcc atc aaa aga    2716
Ala Arg Ile Lys Lys Asp Gly Leu Arg Met Asp Ala Ala Ile Lys Arg
                845                 850                 855 atg aaa gaa tat gcc tcc aaa gat gat cac agg gac ttt gca gga gaa    2764
Met Lys Glu Tyr Ala Ser Lys Asp Asp His Arg Asp Phe Ala Gly Glu
            860                 865                 870 ctg gaa gtt ctt tgt aaa ctt gga cac cat cca aac atc atc aat ctc    2812
Leu Glu Val Leu Cys Lys Leu Gly His His Pro Asn Ile Ile Asn Leu
        875                 880                 885 tta gga gca tgt gaa cat cga ggc tac ttg tac ctg gcc att gag tac    2860
Leu Gly Ala Cys Glu His Arg Gly Tyr Leu Tyr Leu Ala Ile Glu Tyr
890                 895                 900 gcg ccc cat gga aac ctt ctg gac ttc ctt cgc aag agc cgt gtg ctg    2908
Ala Pro His Gly Asn Leu Leu Asp Phe Leu Arg Lys Ser Arg Val Leu
905                 910                 915                 920 gag acg gac cca gca ttt gcc att gcc aat agc acc gcg tcc aca ctg    2956
Glu Thr Asp Pro Ala Phe Ala Ile Ala Asn Ser Thr Ala Ser Thr Leu
                925                 930                 935 tcc tcc cag cag ctc ctt cac ttc gct gcc gac gtg gcc cgg ggc atg    3004
Ser Ser Gln Gln Leu Leu His Phe Ala Ala Asp Val Ala Arg Gly Met
            940                 945                 950 gac tac ttg agc caa aaa cag ttt atc cac agg gat ctg gct gcc aga    3052
Asp Tyr Leu Ser Gln Lys Gln Phe Ile His Arg Asp Leu Ala Ala Arg
        955                 960                 965 aac att tta gtt ggt gaa aac tat gtg gca aaa ata gca gat ttt gga    3100
Asn Ile Leu Val Gly Glu Asn Tyr Val Ala Lys Ile Ala Asp Phe Gly
970                 975                 980 ttg tcc cga ggt caa gag gtg tac gtg aaa aag aca atg gga agg ctc    3148
Leu Ser Arg Gly Gln Glu Val Tyr Val Lys Lys Thr Met Gly Arg Leu
985                 990                 995                 1000 cca gtg cgc tgg atg gcc atc gag tca ctg  aat tac agt gtg tac       3193
Pro Val Arg Trp Met Ala Ile Glu Ser Leu Asn Tyr Ser Val Tyr
                1005                1010                1015 aca acc aac agt gat gta tgg tcc tat ggt  gtg tta cta tgg gag       3238
Thr Thr Asn Ser Asp Val Trp Ser Tyr Gly Val Leu Leu Trp Glu
            1020                1025                1030 att gtt agc tta gga ggc aca ccc tac tgc  ggg atg act tgt gca       3283
Ile Val Ser Leu Gly Gly Thr Pro Tyr Cys Gly Met Thr Cys Ala
        1035                1040                1045 gaa ctc tac gag aag  ctg ccc cag ggc tac  aga ctg gag aag ccc      3328
Glu Leu Tyr Glu Lys Leu Pro Gln Gly Tyr Arg Leu Glu Lys Pro
```

-continued

```
                    1050              1055              1060
ctg aac tgt gat gat  gag gtg tat gat  cta atg aga caa tgc tgg      3373
Leu Asn Cys Asp Asp  Glu Val Tyr Asp  Leu Met Arg Gln Cys Trp
            1065              1070              1075 cgg gag aag cct tat  gag agg cca tca  ttt gcc cag ata ttg gtg      3418
Arg Glu Lys Pro Tyr  Glu Arg Pro Ser  Phe Ala Gln Ile Leu Val
            1080              1085              1090 tcc tta aac aga atg  tta gag gag cga  aag acc tac gtg aat acc      3463
Ser Leu Asn Arg Met  Leu Glu Glu Arg  Lys Thr Tyr Val Asn Thr
            1095              1100              1105 acg ctt tat gag aag  ttt act tat gca  gga att gac tgt tct gct      3508
Thr Leu Tyr Glu Lys  Phe Thr Tyr Ala  Gly Ile Asp Cys Ser Ala
            1110              1115              1120 gaa gaa gcg gcc tag acagaacat ctgtataccc tctgtttccc tttcactggc     3563
Glu Glu Ala Ala atgggagacc cttgacaact gctgagaaaa catgcctctg ccaaaggatg tgatatataa   3623
gtgtacatat gtgctggaat ctaacaagt cataggttaa tatttaagac actgaaaaat   3683
ctaagtgata taaatcagat tcttctctct cattttatcc ctcacctgta gcatgccagt  3743
cccgtttcat ttagtcatgt gaccactctg tcttgtgttt ccacagcctg caagttcagt  3803
ccaggatgct aacatctaaa aatagactta aatctcattg cttacaagcc taagaatctt  3863
tagagaagta tacataagtt taggataaaa taatgggatt ttcttttctt ttctctggta  3923
atattgactt gtatatttta agaaataaca gaaagcctgg gtgacatttg ggagacatgt  3983
gacatttata tattgaatta atatccctac atgtattgca cattgtaaaa agttttagtt  4043
ttgatgagtt gtgagtttac cttgtatact gtaggcacac tttgcactga tatatcatga  4103
gtgaataaat gtcttgccta ctcaaaaaaa aaaaa                             4138
```

<210> SEQ ID NO 8
<211> LENGTH: 1124
<212> TYPE: PRT
<213> ORGANISM: Homo sapiens

<400> SEQUENCE: 8

```
Met Asp Ser Leu Ala Ser Leu Val Leu Cys Gly Val Ser Leu Leu Leu
1               5                   10                  15

Ser Gly Thr Val Glu Gly Ala Met Asp Leu Ile Leu Ile Asn Ser Leu
            20                  25                  30

Pro Leu Val Ser Asp Ala Glu Thr Ser Leu Thr Cys Ile Ala Ser Gly
        35                  40                  45

Trp Arg Pro His Glu Pro Ile Thr Ile Gly Arg Asp Phe Glu Ala Leu
    50                  55                  60

Met Asn Gln His Gln Asp Pro Leu Glu Val Thr Gln Asp Val Thr Arg
65                  70                  75                  80

Glu Trp Ala Lys Lys Val Val Trp Lys Arg Glu Lys Ala Ser Lys Ile
                85                  90                  95

Asn Gly Ala Tyr Phe Cys Glu Gly Arg Val Arg Gly Glu Ala Ile Arg
            100                 105                 110

Ile Arg Thr Met Lys Met Arg Gln Gln Ala Ser Phe Leu Pro Ala Thr
        115                 120                 125

Leu Thr Met Thr Val Asp Lys Gly Asp Asn Val Asn Ile Ser Phe Lys
    130                 135                 140

Lys Val Leu Ile Lys Glu Glu Asp Ala Val Ile Tyr Lys Asn Gly Ser
145                 150                 155                 160
```

```
Phe Ile His Ser Val Pro Arg His Glu Val Pro Asp Ile Leu Glu Val
                165                 170                 175

His Leu Pro His Ala Gln Pro Gln Asp Ala Gly Val Tyr Ser Ala Arg
            180                 185                 190

Tyr Ile Gly Gly Asn Leu Phe Thr Ser Ala Phe Thr Arg Leu Ile Val
        195                 200                 205

Arg Arg Cys Glu Ala Gln Lys Trp Gly Pro Glu Cys Asn His Leu Cys
    210                 215                 220

Thr Ala Cys Met Asn Asn Gly Val Cys His Glu Asp Thr Gly Glu Cys
225                 230                 235                 240

Ile Cys Pro Pro Gly Phe Met Gly Arg Thr Cys Glu Lys Ala Cys Glu
                245                 250                 255

Leu His Thr Phe Gly Arg Thr Cys Lys Glu Arg Cys Ser Gly Gln Glu
            260                 265                 270

Gly Cys Lys Ser Tyr Val Phe Cys Leu Pro Asp Pro Tyr Gly Cys Ser
        275                 280                 285

Cys Ala Thr Gly Trp Lys Gly Leu Gln Cys Asn Glu Ala Cys His Pro
    290                 295                 300

Gly Phe Tyr Gly Pro Asp Cys Lys Leu Arg Cys Ser Cys Asn Asn Gly
305                 310                 315                 320

Glu Met Cys Asp Arg Phe Gln Gly Cys Leu Cys Ser Pro Gly Trp Gln
                325                 330                 335

Gly Leu Gln Cys Glu Arg Glu Gly Ile Pro Arg Met Thr Pro Lys Ile
            340                 345                 350

Val Asp Leu Pro Asp His Ile Glu Val Asn Ser Gly Lys Phe Asn Pro
        355                 360                 365

Ile Cys Lys Ala Ser Gly Trp Pro Leu Pro Thr Asn Glu Glu Met Thr
    370                 375                 380

Leu Val Lys Pro Asp Gly Thr Val Leu His Pro Lys Asp Phe Asn His
385                 390                 395                 400

Thr Asp His Phe Ser Val Ala Ile Phe Thr Ile His Arg Ile Leu Pro
                405                 410                 415

Pro Asp Ser Gly Val Trp Val Cys Ser Val Asn Thr Val Ala Gly Met
            420                 425                 430

Val Glu Lys Pro Phe Asn Ile Ser Val Lys Val Leu Pro Lys Pro Leu
        435                 440                 445

Asn Ala Pro Asn Val Ile Asp Thr Gly His Asn Phe Ala Val Ile Asn
    450                 455                 460

Ile Ser Ser Glu Pro Tyr Phe Gly Asp Gly Pro Ile Lys Ser Lys Lys
465                 470                 475                 480

Leu Leu Tyr Lys Pro Val Asn His Tyr Glu Ala Trp Gln His Ile Gln
                485                 490                 495

Val Thr Asn Glu Ile Val Thr Leu Asn Tyr Leu Glu Pro Arg Thr Glu
            500                 505                 510

Tyr Glu Leu Cys Val Gln Leu Val Arg Arg Gly Glu Gly Gly Glu Gly
        515                 520                 525

His Pro Gly Pro Val Arg Arg Phe Thr Thr Ala Ser Ile Gly Leu Pro
    530                 535                 540

Pro Pro Arg Gly Leu Asn Leu Leu Pro Lys Ser Gln Thr Thr Leu Asn
545                 550                 555                 560

Leu Thr Trp Gln Pro Ile Phe Pro Ser Ser Glu Asp Asp Phe Tyr Val
                565                 570                 575

Glu Val Glu Arg Arg Ser Val Gln Lys Ser Asp Gln Gln Asn Ile Lys
```

-continued

```
            580                 585                 590
Val Pro Gly Asn Leu Thr Ser Val Leu Asn Asn Leu His Pro Arg
        595                 600                 605
Glu Gln Tyr Val Val Arg Ala Arg Val Asn Thr Lys Ala Gln Gly Glu
        610                 615                 620
Trp Ser Glu Asp Leu Thr Ala Trp Thr Leu Ser Asp Ile Leu Pro Pro
625                 630                 635                 640
Gln Pro Glu Asn Ile Lys Ile Ser Asn Ile Thr His Ser Ser Ala Val
                    645                 650                 655
Ile Ser Trp Thr Ile Leu Asp Gly Tyr Ser Ile Ser Ser Ile Thr Ile
                660                 665                 670
Arg Tyr Lys Val Gln Gly Lys Asn Glu Asp Gln His Val Asp Val Lys
            675                 680                 685
Ile Lys Asn Ala Thr Ile Ile Gln Tyr Gln Leu Lys Gly Leu Glu Pro
        690                 695                 700
Glu Thr Ala Tyr Gln Val Asp Ile Phe Ala Glu Asn Ile Gly Ser
705                 710                 715                 720
Ser Asn Pro Ala Phe Ser His Glu Leu Val Thr Leu Pro Glu Ser Gln
                    725                 730                 735
Ala Pro Ala Asp Leu Gly Gly Gly Lys Met Leu Leu Ile Ala Ile Leu
                740                 745                 750
Gly Ser Ala Gly Met Thr Cys Leu Thr Val Leu Leu Ala Phe Leu Ile
            755                 760                 765
Ile Leu Gln Leu Lys Arg Ala Asn Val Gln Arg Arg Met Ala Gln Ala
        770                 775                 780
Phe Gln Asn Val Arg Glu Glu Pro Ala Val Gln Phe Asn Ser Gly Thr
785                 790                 795                 800
Leu Ala Leu Asn Arg Lys Val Lys Asn Asn Pro Asp Pro Thr Ile Tyr
                    805                 810                 815
Pro Val Leu Asp Trp Asn Asp Ile Lys Phe Gln Asp Val Ile Gly Glu
                820                 825                 830
Gly Asn Phe Gly Gln Val Leu Lys Ala Arg Ile Lys Lys Asp Gly Leu
            835                 840                 845
Arg Met Asp Ala Ala Ile Lys Arg Met Lys Glu Tyr Ala Ser Lys Asp
        850                 855                 860
Asp His Arg Asp Phe Ala Gly Glu Leu Glu Val Leu Cys Lys Leu Gly
865                 870                 875                 880
His His Pro Asn Ile Ile Asn Leu Leu Gly Ala Cys Glu His Arg Gly
                    885                 890                 895
Tyr Leu Tyr Leu Ala Ile Glu Tyr Ala Pro His Gly Asn Leu Leu Asp
                900                 905                 910
Phe Leu Arg Lys Ser Arg Val Leu Glu Thr Asp Pro Ala Phe Ala Ile
            915                 920                 925
Ala Asn Ser Thr Ala Ser Thr Leu Ser Ser Gln Gln Leu Leu His Phe
        930                 935                 940
Ala Ala Asp Val Ala Arg Gly Met Asp Tyr Leu Ser Gln Lys Gln Phe
945                 950                 955                 960
Ile His Arg Asp Leu Ala Ala Arg Asn Ile Leu Val Gly Glu Asn Tyr
                    965                 970                 975
Val Ala Lys Ile Ala Asp Phe Gly Leu Ser Arg Gly Gln Glu Val Tyr
                980                 985                 990
Val Lys Lys Thr Met Gly Arg Leu  Pro Val Arg Trp Met  Ala Ile Glu
            995                 1000                1005
```

```
Ser Leu Asn Tyr Ser Val Tyr Thr Thr Asn Ser Asp Val Trp Ser
    1010                1015                1020

Tyr Gly Val Leu Leu Trp Glu Ile Val Ser Leu Gly Gly Thr Pro
    1025                1030                1035

Tyr Cys Gly Met Thr Cys Ala Glu Leu Tyr Glu Lys Leu Pro Gln
    1040                1045                1050

Gly Tyr Arg Leu Glu Lys Pro Leu Asn Cys Asp Asp Glu Val Tyr
    1055                1060                1065

Asp Leu Met Arg Gln Cys Trp Arg Glu Lys Pro Tyr Glu Arg Pro
    1070                1075                1080

Ser Phe Ala Gln Ile Leu Val Ser Leu Asn Arg Met Leu Glu Glu
    1085                1090                1095

Arg Lys Thr Tyr Val Asn Thr Thr Leu Tyr Glu Lys Phe Thr Tyr
    1100                1105                1110

Ala Gly Ile Asp Cys Ser Ala Glu Glu Ala Ala
    1115                1120
```

<210> SEQ ID NO 9
<211> LENGTH: 355
<212> TYPE: PRT
<213> ORGANISM: Homo sapiens

<400> SEQUENCE: 9

```
Arg Gln Lys Val Ser His Gly Arg Glu Arg Pro Ser Ala Arg Leu Ser
1               5                   10                  15

Ile Arg Arg Asp Arg Pro Leu Ser Val His Leu Asn Leu Gly Gln Lys
            20                  25                  30

Gly Asn Arg Lys Thr Ser Cys Pro Ile Lys Ile Asn Gln Phe Glu Gly
        35                  40                  45

His Phe Met Lys Leu Gln Ala Asp Ser Asn Tyr Leu Leu Ser Lys Glu
    50                  55                  60

Tyr Glu Glu Leu Lys Asp Val Gly Arg Asn Gln Ser Cys Asp Ile Ala
65                  70                  75                  80

Leu Leu Pro Glu Asn Arg Gly Lys Asn Arg Tyr Asn Asn Ile Leu Pro
                85                  90                  95

Tyr Asp Ala Thr Arg Val Lys Leu Ser Asn Val Asp Asp Asp Pro Cys
            100                 105                 110

Ser Asp Tyr Ile Asn Ala Ser Tyr Ile Pro Gly Asn Asn Phe Arg Arg
        115                 120                 125

Glu Tyr Ile Val Thr Gln Gly Pro Leu Pro Gly Thr Lys Asp Asp Phe
    130                 135                 140

Trp Lys Met Val Trp Glu Gln Asn Val His Asn Ile Val Met Val Thr
145                 150                 155                 160

Gln Cys Val Glu Lys Gly Arg Val Lys Cys Asp His Tyr Trp Pro Ala
                165                 170                 175

Asp Gln Asp Ser Leu Tyr Tyr Gly Asp Leu Ile Leu Gln Met Leu Ser
            180                 185                 190

Glu Ser Val Leu Pro Glu Trp Thr Ile Arg Glu Phe Lys Ile Cys Gly
        195                 200                 205

Glu Glu Gln Leu Asp Ala His Arg Leu Ile Arg His Phe His Tyr Thr
    210                 215                 220

Val Trp Pro Asp His Gly Val Pro Glu Thr Thr Gln Ser Leu Ile Gln
225                 230                 235                 240

Phe Val Arg Thr Val Arg Asp Tyr Ile Asn Arg Ser Pro Gly Ala Gly
```

```
                      245                 250                 255
Pro Thr Val Val His Cys Ser Ala Gly Val Gly Arg Thr Gly Thr Phe
            260                 265                 270
Ile Ala Leu Asp Arg Ile Leu Gln Gln Leu Asp Ser Lys Asp Ser Val
            275                 280                 285
Asp Ile Tyr Gly Ala Val His Asp Leu Arg Leu His Arg Val His Met
            290                 295                 300
Val Gln Thr Glu Cys Gln Tyr Val Tyr Leu His Gln Cys Val Arg Asp
305                 310                 315                 320
Val Leu Arg Ala Arg Lys Leu Arg Ser Glu Gln Glu Asn Pro Leu Phe
                325                 330                 335
Pro Ile Tyr Glu Asn Val Asn Pro Glu Tyr His Arg Asp Pro Val Tyr
            340                 345                 350
Ser Arg His
        355

<210> SEQ ID NO 10
<211> LENGTH: 1704
<212> TYPE: DNA
<213> ORGANISM: Homo sapiens
<220> FEATURE:
<221> NAME/KEY: CDS
<222> LOCATION: (1)..(1704)

<400> SEQUENCE: 10 aag cgg gcc aat gga ggg gaa ctg aag aca ggc tac ttg tcc atc gtc      48
Lys Arg Ala Asn Gly Gly Glu Leu Lys Thr Gly Tyr Leu Ser Ile Val
1               5                   10                  15 atg gat cca gat gaa ctc cca ttg gat gaa cat tgt gaa cga ctg cct      96
Met Asp Pro Asp Glu Leu Pro Leu Asp Glu His Cys Glu Arg Leu Pro
                20                  25                  30 tat gat gcc agc aaa tgg gaa ttc ccc aga gac cgg ctg aag cta ggt      144
Tyr Asp Ala Ser Lys Trp Glu Phe Pro Arg Asp Arg Leu Lys Leu Gly
            35                  40                  45 aag cct ctt ggc cgt ggt gcc ttt ggc caa gtg att gaa gca gat gcc      192
Lys Pro Leu Gly Arg Gly Ala Phe Gly Gln Val Ile Glu Ala Asp Ala
        50                  55                  60 ttt gga att gac aag aca gca act tgc agg aca gta gca gtc aaa atg      240
Phe Gly Ile Asp Lys Thr Ala Thr Cys Arg Thr Val Ala Val Lys Met
65                  70                  75                  80 ttg aaa gaa gga gca aca cac agt gag cat cga gct ctc atg tct gaa      288
Leu Lys Glu Gly Ala Thr His Ser Glu His Arg Ala Leu Met Ser Glu
                85                  90                  95 ctc aag atc ctc att cat att ggt cac cat ctc aat gtg gtc aac ctt      336
Leu Lys Ile Leu Ile His Ile Gly His His Leu Asn Val Val Asn Leu
            100                 105                 110 cta ggt gcc tgt acc aag cca gga ggg cca ctc atg gtg att gtg gaa      384
Leu Gly Ala Cys Thr Lys Pro Gly Gly Pro Leu Met Val Ile Val Glu
        115                 120                 125 ttc tgc aaa ttt gga aac ctg tcc act tac ctg agg agc aag aga aat      432
Phe Cys Lys Phe Gly Asn Leu Ser Thr Tyr Leu Arg Ser Lys Arg Asn
    130                 135                 140 gaa ttt gtc ccc tac aag acc aaa ggg gca cga ttc cgt caa ggg aaa      480
Glu Phe Val Pro Tyr Lys Thr Lys Gly Ala Arg Phe Arg Gln Gly Lys
145                 150                 155                 160 gac tac gtt gga gca atc cct gtg gat ctg aaa cgg cgc ttg gac agc      528
Asp Tyr Val Gly Ala Ile Pro Val Asp Leu Lys Arg Arg Leu Asp Ser
                165                 170                 175 atc acc agt agc cag agc tca gcc agc tct gga ttt gtg gag gag aag      576
```

```
Ile Thr Ser Ser Gln Ser Ser Ala Ser Ser Gly Phe Val Glu Glu Lys
            180                 185                 190 tcc ctc agt gat gta gaa gaa gag gaa gct cct gaa gat ctg tat aag       624
Ser Leu Ser Asp Val Glu Glu Glu Glu Ala Pro Glu Asp Leu Tyr Lys
            195                 200                 205 gac ttc ctg acc ttg gag cat ctc atc tgt tac agc ttc caa gtg gct       672
Asp Phe Leu Thr Leu Glu His Leu Ile Cys Tyr Ser Phe Gln Val Ala
            210                 215                 220 aag ggc atg gag ttc ttg gca tcg cga aag tgt atc cac agg gac ctg       720
Lys Gly Met Glu Phe Leu Ala Ser Arg Lys Cys Ile His Arg Asp Leu
225                 230                 235                 240 gcg gca cga aat atc ctc tta tcg gag aag aac gtg gtt aaa atc tgt       768
Ala Ala Arg Asn Ile Leu Leu Ser Glu Lys Asn Val Val Lys Ile Cys
                245                 250                 255 gac ttt ggc ttg gcc cgg gat att tat aaa gat cca gat tat gtc aga       816
Asp Phe Gly Leu Ala Arg Asp Ile Tyr Lys Asp Pro Asp Tyr Val Arg
            260                 265                 270 aaa gga gat gct cgc ctc cct ttg aaa tgg atg gcc cca gaa aca att       864
Lys Gly Asp Ala Arg Leu Pro Leu Lys Trp Met Ala Pro Glu Thr Ile
            275                 280                 285 ttt gac aga gtg tac aca atc cag agt gac gtc tgg tct ttt ggt gtt       912
Phe Asp Arg Val Tyr Thr Ile Gln Ser Asp Val Trp Ser Phe Gly Val
290                 295                 300 ttg ctg tgg gaa ata ttt tcc tta ggt gct tct cca tat cct ggg gta       960
Leu Leu Trp Glu Ile Phe Ser Leu Gly Ala Ser Pro Tyr Pro Gly Val
305                 310                 315                 320 aag att gat gaa gaa ttt tgt agg cga ttg aaa gaa gga act aga atg      1008
Lys Ile Asp Glu Glu Phe Cys Arg Arg Leu Lys Glu Gly Thr Arg Met
                325                 330                 335 agg gcc cct gat tat act aca cca gaa atg tac cag acc atg ctg gac      1056
Arg Ala Pro Asp Tyr Thr Thr Pro Glu Met Tyr Gln Thr Met Leu Asp
            340                 345                 350 tgc tgg cac ggg gag ccc agt cag aga ccc acg ttt tca gag ttg gtg      1104
Cys Trp His Gly Glu Pro Ser Gln Arg Pro Thr Phe Ser Glu Leu Val
            355                 360                 365 gaa cat ttg gga aat ctc ttg caa gct aat gct cag cag gat ggc aaa      1152
Glu His Leu Gly Asn Leu Leu Gln Ala Asn Ala Gln Gln Asp Gly Lys
            370                 375                 380 gac tac att gtt ctt ccg ata tca gag act ttg agc atg gaa gag gat      1200
Asp Tyr Ile Val Leu Pro Ile Ser Glu Thr Leu Ser Met Glu Glu Asp
385                 390                 395                 400 tct gga ctc tct ctg cct acc tca cct gtt tcc tgt atg gag gag gag      1248
Ser Gly Leu Ser Leu Pro Thr Ser Pro Val Ser Cys Met Glu Glu Glu
            405                 410                 415 gaa gta tgt gac ccc aaa ttc cat tat gac aac aca gca gga atc agt      1296
Glu Val Cys Asp Pro Lys Phe His Tyr Asp Asn Thr Ala Gly Ile Ser
            420                 425                 430 cag tat ctg cag aac agt aag cga aag agc cgg cct gtg agt gta aaa      1344
Gln Tyr Leu Gln Asn Ser Lys Arg Lys Ser Arg Pro Val Ser Val Lys
            435                 440                 445 aca ttt gaa gat atc ccg tta gaa gaa cca gaa gta aaa gta atc cca      1392
Thr Phe Glu Asp Ile Pro Leu Glu Glu Pro Glu Val Lys Val Ile Pro
450                 455                 460 gat gac aac cag acg gac agt ggt atg gtt ctt gcc tca gaa gag ctg      1440
Asp Asp Asn Gln Thr Asp Ser Gly Met Val Leu Ala Ser Glu Glu Leu
465                 470                 475                 480 aaa act ttg gaa gac aga acc aaa tta tct cca tct ttt ggt gga atg      1488
Lys Thr Leu Glu Asp Arg Thr Lys Leu Ser Pro Ser Phe Gly Gly Met
            485                 490                 495
```

```
gtg ccc agc aaa agc agg gag tct gtg gca tct gaa ggc tca aac cag    1536
Val Pro Ser Lys Ser Arg Glu Ser Val Ala Ser Glu Gly Ser Asn Gln
        500                 505                 510 aca agc ggc tac cag tcc gga tat cac tcc gat gac aca gac acc acc    1584
Thr Ser Gly Tyr Gln Ser Gly Tyr His Ser Asp Asp Thr Asp Thr Thr
        515                 520                 525 gtg tac tcc agt gag gaa gca gaa ctt tta aag ctg ata gag att gga    1632
Val Tyr Ser Ser Glu Glu Ala Glu Leu Leu Lys Leu Ile Glu Ile Gly
        530                 535                 540 gtg caa acc ggt agc aca gcc cag att ctc cag cct gac tcg ggg acc    1680
Val Gln Thr Gly Ser Thr Ala Gln Ile Leu Gln Pro Asp Ser Gly Thr
545                 550                 555                 560 aca ctg agc tct cct cct gtt taa                                    1704
Thr Leu Ser Ser Pro Pro Val
                565
```

<210> SEQ ID NO 11
<211> LENGTH: 567
<212> TYPE: PRT
<213> ORGANISM: Homo sapiens

<400> SEQUENCE: 11

```
Lys Arg Ala Asn Gly Gly Glu Leu Lys Thr Gly Tyr Leu Ser Ile Val
1               5                   10                  15

Met Asp Pro Asp Glu Leu Pro Leu Asp Glu His Cys Glu Arg Leu Pro
            20                  25                  30

Tyr Asp Ala Ser Lys Trp Glu Phe Pro Arg Asp Arg Leu Lys Leu Gly
        35                  40                  45

Lys Pro Leu Gly Arg Gly Ala Phe Gly Gln Val Ile Glu Ala Asp Ala
    50                  55                  60

Phe Gly Ile Asp Lys Thr Ala Thr Cys Arg Thr Val Ala Val Lys Met
65                  70                  75                  80

Leu Lys Glu Gly Ala Thr His Ser Glu His Arg Ala Leu Met Ser Glu
                85                  90                  95

Leu Lys Ile Leu Ile His Ile Gly His His Leu Asn Val Val Asn Leu
            100                 105                 110

Leu Gly Ala Cys Thr Lys Pro Gly Gly Pro Leu Met Val Ile Val Glu
        115                 120                 125

Phe Cys Lys Phe Gly Asn Leu Ser Thr Tyr Leu Arg Ser Lys Arg Asn
    130                 135                 140

Glu Phe Val Pro Tyr Lys Thr Lys Gly Ala Arg Phe Arg Gln Gly Lys
145                 150                 155                 160

Asp Tyr Val Gly Ala Ile Pro Val Asp Leu Lys Arg Arg Leu Asp Ser
                165                 170                 175

Ile Thr Ser Ser Gln Ser Ser Ala Ser Ser Gly Phe Val Glu Glu Lys
            180                 185                 190

Ser Leu Ser Asp Val Glu Glu Glu Ala Pro Glu Asp Leu Tyr Lys
        195                 200                 205

Asp Phe Leu Thr Leu Glu His Leu Ile Cys Tyr Ser Phe Gln Val Ala
    210                 215                 220

Lys Gly Met Glu Phe Leu Ala Ser Arg Lys Cys Ile His Arg Asp Leu
225                 230                 235                 240

Ala Ala Arg Asn Ile Leu Leu Ser Glu Lys Asn Val Val Lys Ile Cys
                245                 250                 255

Asp Phe Gly Leu Ala Arg Asp Ile Tyr Lys Asp Pro Asp Tyr Val Arg
            260                 265                 270
```

```
Lys Gly Asp Ala Arg Leu Pro Leu Lys Trp Met Ala Pro Glu Thr Ile
            275                 280                 285

Phe Asp Arg Val Tyr Thr Ile Gln Ser Asp Val Trp Ser Phe Gly Val
        290                 295                 300

Leu Leu Trp Glu Ile Phe Ser Leu Gly Ala Ser Pro Tyr Pro Gly Val
305                 310                 315                 320

Lys Ile Asp Glu Glu Phe Cys Arg Arg Leu Lys Glu Gly Thr Arg Met
                325                 330                 335

Arg Ala Pro Asp Tyr Thr Thr Pro Glu Met Tyr Gln Thr Met Leu Asp
            340                 345                 350

Cys Trp His Gly Glu Pro Ser Gln Arg Pro Thr Phe Ser Glu Leu Val
        355                 360                 365

Glu His Leu Gly Asn Leu Leu Gln Ala Asn Ala Gln Gln Asp Gly Lys
    370                 375                 380

Asp Tyr Ile Val Leu Pro Ile Ser Glu Thr Leu Ser Met Glu Glu Asp
385                 390                 395                 400

Ser Gly Leu Ser Leu Pro Thr Ser Pro Val Ser Cys Met Glu Glu Glu
                405                 410                 415

Glu Val Cys Asp Pro Lys Phe His Tyr Asp Asn Thr Ala Gly Ile Ser
            420                 425                 430

Gln Tyr Leu Gln Asn Ser Lys Arg Lys Ser Arg Pro Val Ser Val Lys
        435                 440                 445

Thr Phe Glu Asp Ile Pro Leu Glu Glu Pro Glu Val Lys Val Ile Pro
    450                 455                 460

Asp Asp Asn Gln Thr Asp Ser Gly Met Val Leu Ala Ser Glu Glu Leu
465                 470                 475                 480

Lys Thr Leu Glu Asp Arg Thr Lys Leu Ser Pro Ser Phe Gly Gly Met
                485                 490                 495

Val Pro Ser Lys Ser Arg Glu Ser Val Ala Ser Glu Gly Ser Asn Gln
            500                 505                 510

Thr Ser Gly Tyr Gln Ser Gly Tyr His Ser Asp Asp Thr Asp Thr Thr
        515                 520                 525

Val Tyr Ser Ser Glu Glu Ala Glu Leu Leu Lys Leu Ile Glu Ile Gly
    530                 535                 540

Val Gln Thr Gly Ser Thr Ala Gln Ile Leu Gln Pro Asp Ser Gly Thr
545                 550                 555                 560

Thr Leu Ser Ser Pro Pro Val
                565

<210> SEQ ID NO 12
<211> LENGTH: 1067
<212> TYPE: DNA
<213> ORGANISM: Homo sapiens
<220> FEATURE:
<221> NAME/KEY: CDS
<222> LOCATION: (1)..(1059)

<400> SEQUENCE: 12 aag agg gca aat gtg caa agg aga atg gcc caa gcc ttc caa aac gtg      48
Lys Arg Ala Asn Val Gln Arg Arg Met Ala Gln Ala Phe Gln Asn Val
1               5                   10                  15 agg gaa gaa cca gct gtg cag ttc aac tca ggg act ctg gcc cta aac      96
Arg Glu Glu Pro Ala Val Gln Phe Asn Ser Gly Thr Leu Ala Leu Asn
            20                  25                  30 agg aag gtc aaa aac aac cca gat cct aca att tat cca gtg ctt gac     144
Arg Lys Val Lys Asn Asn Pro Asp Pro Thr Ile Tyr Pro Val Leu Asp
        35                  40                  45
```

```
tgg aat gac atc aaa ttt caa gat gtg att ggg gag ggc aat ttt ggc    192
Trp Asn Asp Ile Lys Phe Gln Asp Val Ile Gly Glu Gly Asn Phe Gly
 50                  55                  60 caa gtt ctt aag gcg cgc atc aag aag gat ggg tta cgg atg gat gct    240
Gln Val Leu Lys Ala Arg Ile Lys Lys Asp Gly Leu Arg Met Asp Ala
 65                  70                  75                  80 gcc atc aaa aga atg aaa gaa tat gcc tcc aaa gat gat cac agg gac    288
Ala Ile Lys Arg Met Lys Glu Tyr Ala Ser Lys Asp Asp His Arg Asp
                 85                  90                  95 ttt gca gga gaa ctg gaa gtt ctt tgt aaa ctt gga cac cat cca aac    336
Phe Ala Gly Glu Leu Glu Val Leu Cys Lys Leu Gly His His Pro Asn
            100                 105                 110 atc atc aat ctc tta gga gca tgt gaa cat cga ggc tac ttg tac ctg    384
Ile Ile Asn Leu Leu Gly Ala Cys Glu His Arg Gly Tyr Leu Tyr Leu
        115                 120                 125 gcc att gag tac gcg ccc cat gga aac ctt ctg gac ttc ctt cgc aag    432
Ala Ile Glu Tyr Ala Pro His Gly Asn Leu Leu Asp Phe Leu Arg Lys
    130                 135                 140 agc cgt gtg ctg gag acg gac cca gca ttt gcc att gcc aat agc acc    480
Ser Arg Val Leu Glu Thr Asp Pro Ala Phe Ala Ile Ala Asn Ser Thr
145                 150                 155                 160 gcg tcc aca ctg tcc tcc cag cag ctc ctt cac ttc gct gcc gac gtg    528
Ala Ser Thr Leu Ser Ser Gln Gln Leu Leu His Phe Ala Ala Asp Val
                165                 170                 175 gcc cgg ggc atg gac tac ttg agc caa aaa cag ttt atc cac agg gat    576
Ala Arg Gly Met Asp Tyr Leu Ser Gln Lys Gln Phe Ile His Arg Asp
            180                 185                 190 ctg gct gcc aga aac att tta gtt ggt gaa aac tat gtg gca aaa ata    624
Leu Ala Ala Arg Asn Ile Leu Val Gly Glu Asn Tyr Val Ala Lys Ile
        195                 200                 205 gca gat ttt gga ttg tcc cga ggt caa gag gtg tac gtg aaa aag aca    672
Ala Asp Phe Gly Leu Ser Arg Gly Gln Glu Val Tyr Val Lys Lys Thr
    210                 215                 220 atg gga agg ctc cca gtg cgc tgg atg gcc atc gag tca ctg aat tac    720
Met Gly Arg Leu Pro Val Arg Trp Met Ala Ile Glu Ser Leu Asn Tyr
225                 230                 235                 240 agt gtg tac aca acc aac agt gat gta tgg tcc tat ggt gtg tta cta    768
Ser Val Tyr Thr Thr Asn Ser Asp Val Trp Ser Tyr Gly Val Leu Leu
                245                 250                 255 tgg gag att gtt agc tta gga ggc aca ccc tac tgc ggg atg act tgt    816
Trp Glu Ile Val Ser Leu Gly Gly Thr Pro Tyr Cys Gly Met Thr Cys
            260                 265                 270 gca gaa ctc tac gag aag ctg ccc cag ggc tac aga ctg gag aag ccc    864
Ala Glu Leu Tyr Glu Lys Leu Pro Gln Gly Tyr Arg Leu Glu Lys Pro
        275                 280                 285 ctg aac tgt gat gat gag gtg tat gat cta atg aga caa tgc tgg cgg    912
Leu Asn Cys Asp Asp Glu Val Tyr Asp Leu Met Arg Gln Cys Trp Arg
    290                 295                 300 gag aag cct tat gag agg cca tca ttt gcc cag ata ttg gtg tcc tta    960
Glu Lys Pro Tyr Glu Arg Pro Ser Phe Ala Gln Ile Leu Val Ser Leu
305                 310                 315                 320 aac aga atg tta gag gag cga aag acc tac gtg aat acc acg ctt tat   1008
Asn Arg Met Leu Glu Glu Arg Lys Thr Tyr Val Asn Thr Thr Leu Tyr
                325                 330                 335 gag aag ttt act tat gca gga att gac tgt tct gct gaa gaa gcg gcc   1056
Glu Lys Phe Thr Tyr Ala Gly Ile Asp Cys Ser Ala Glu Glu Ala Ala
            340                 345                 350 tag gacagaac                                                       1067
```

<210> SEQ ID NO 13
<211> LENGTH: 352
<212> TYPE: PRT
<213> ORGANISM: Homo sapiens

<400> SEQUENCE: 13

```
Lys Arg Ala Asn Val Gln Arg Arg Met Ala Gln Ala Phe Gln Asn Val
1               5                   10                  15

Arg Glu Glu Pro Ala Val Gln Phe Asn Ser Gly Thr Leu Ala Leu Asn
            20                  25                  30

Arg Lys Val Lys Asn Asn Pro Asp Pro Thr Ile Tyr Pro Val Leu Asp
        35                  40                  45

Trp Asn Asp Ile Lys Phe Gln Asp Val Ile Gly Glu Gly Asn Phe Gly
    50                  55                  60

Gln Val Leu Lys Ala Arg Ile Lys Lys Asp Gly Leu Arg Met Asp Ala
65              70                  75                  80

Ala Ile Lys Arg Met Lys Glu Tyr Ala Ser Lys Asp Asp His Arg Asp
                85                  90                  95

Phe Ala Gly Glu Leu Glu Val Leu Cys Lys Leu Gly His His Pro Asn
            100                 105                 110

Ile Ile Asn Leu Leu Gly Ala Cys Glu His Arg Gly Tyr Leu Tyr Leu
        115                 120                 125

Ala Ile Glu Tyr Ala Pro His Gly Asn Leu Leu Asp Phe Leu Arg Lys
    130                 135                 140

Ser Arg Val Leu Glu Thr Asp Pro Ala Phe Ala Ile Ala Asn Ser Thr
145                 150                 155                 160

Ala Ser Thr Leu Ser Ser Gln Gln Leu Leu His Phe Ala Ala Asp Val
                165                 170                 175

Ala Arg Gly Met Asp Tyr Leu Ser Gln Lys Gln Phe Ile His Arg Asp
            180                 185                 190

Leu Ala Ala Arg Asn Ile Leu Val Gly Glu Asn Tyr Val Ala Lys Ile
        195                 200                 205

Ala Asp Phe Gly Leu Ser Arg Gly Gln Glu Val Tyr Val Lys Lys Thr
    210                 215                 220

Met Gly Arg Leu Pro Val Arg Trp Met Ala Ile Glu Ser Leu Asn Tyr
225                 230                 235                 240

Ser Val Tyr Thr Thr Asn Ser Asp Val Trp Ser Tyr Gly Val Leu Leu
                245                 250                 255

Trp Glu Ile Val Ser Leu Gly Gly Thr Pro Tyr Cys Gly Met Thr Cys
            260                 265                 270

Ala Glu Leu Tyr Glu Lys Leu Pro Gln Gly Tyr Arg Leu Glu Lys Pro
        275                 280                 285

Leu Asn Cys Asp Asp Glu Val Tyr Asp Leu Met Arg Gln Cys Trp Arg
    290                 295                 300

Glu Lys Pro Tyr Glu Arg Pro Ser Phe Ala Gln Ile Leu Val Ser Leu
305                 310                 315                 320

Asn Arg Met Leu Glu Glu Arg Lys Thr Tyr Val Asn Thr Thr Leu Tyr
                325                 330                 335

Glu Lys Phe Thr Tyr Ala Gly Ile Asp Cys Ser Ala Glu Glu Ala Ala
            340                 345                 350
```

<210> SEQ ID NO 14
<211> LENGTH: 6033
<212> TYPE: DNA
<213> ORGANISM: Homo sapiens

```
<220> FEATURE:
<221> NAME/KEY: misc_feature
<222> LOCATION: (1)..(6033)
<223> OTHER INFORMATION: n = A, T, G, C
<220> FEATURE:
<221> NAME/KEY: CDS
<222> LOCATION: (31)..(5754)
<223> OTHER INFORMATION: n = A, T, G, C

<400> SEQUENCE: 14
gtctcctctg gatcttaact actgagcgca atg ctg agc cat gga gcc ggg ttg        54
                                Met Leu Ser His Gly Ala Gly Leu
                                 1               5 gcc ttg tgg atc aca ctg agc ctg ctg cag act gga ctg gcg gag cca        102
Ala Leu Trp Ile Thr Leu Ser Leu Leu Gln Thr Gly Leu Ala Glu Pro
 10              15                  20 gag aga tgt aac ttc acc ctg gcg gag tcc aag gcc tcc agc cat tct        150
Glu Arg Cys Asn Phe Thr Leu Ala Glu Ser Lys Ala Ser Ser His Ser
 25              30                  35                  40 gtg tct atc cag tgg aga att ttg ggc tca ccc tgt aac ttt agc ctc        198
Val Ser Ile Gln Trp Arg Ile Leu Gly Ser Pro Cys Asn Phe Ser Leu
                 45                  50                  55 atc tat agc agt gac acc ctg ggg gcc gcg ttg tgc cct acc ttt cgg        246
Ile Tyr Ser Ser Asp Thr Leu Gly Ala Ala Leu Cys Pro Thr Phe Arg
             60                  65                  70 ata gac aac acc aca tac gga tgt aac ctt caa gat tta caa gca gga        294
Ile Asp Asn Thr Thr Tyr Gly Cys Asn Leu Gln Asp Leu Gln Ala Gly
         75                  80                  85 acc atc tat aac ttc aag att att tct ctg gat gaa gag aga act gtg        342
Thr Ile Tyr Asn Phe Lys Ile Ile Ser Leu Asp Glu Glu Arg Thr Val
     90                  95                 100 gtc ttg caa aca gat cct tta cct cct gct agg ttt gga gtc agt aaa        390
Val Leu Gln Thr Asp Pro Leu Pro Pro Ala Arg Phe Gly Val Ser Lys
105                 110                 115                 120 gag aag acg act tca acc ggc ttg cat gtt tgg tgg act cct tct tcc        438
Glu Lys Thr Thr Ser Thr Gly Leu His Val Trp Trp Thr Pro Ser Ser
                125                 130                 135 gga aaa gtc acc tca tat gag gtg caa tta ttt gat gaa aat aac caa        486
Gly Lys Val Thr Ser Tyr Glu Val Gln Leu Phe Asp Glu Asn Asn Gln
            140                 145                 150 aag ata cag ggg gtt caa att caa gaa agt act tca tgg aat gaa tac        534
Lys Ile Gln Gly Val Gln Ile Gln Glu Ser Thr Ser Trp Asn Glu Tyr
        155                 160                 165 act ttt ttc aat ctc act gct ggt agt aaa tac aat att gcc atc aca        582
Thr Phe Phe Asn Leu Thr Ala Gly Ser Lys Tyr Asn Ile Ala Ile Thr
    170                 175                 180 gct gtt tct gga gga aaa cgt tct ttt tca gtt tat acc aat gga tca        630
Ala Val Ser Gly Gly Lys Arg Ser Phe Ser Val Tyr Thr Asn Gly Ser
185                 190                 195                 200 aca gtg cca tct cca gtg aaa gat att ggt att tcc aca aaa gcc aat        678
Thr Val Pro Ser Pro Val Lys Asp Ile Gly Ile Ser Thr Lys Ala Asn
                205                 210                 215 tct ctc ctg att tcc tgg tcc cat ggt tct ggg aat gtg aaa cga tac        726
Ser Leu Leu Ile Ser Trp Ser His Gly Ser Gly Asn Val Lys Arg Tyr
            220                 225                 230 cgg ctg atg cta atg gat aaa ggg atc cta gtt cat ggc ggt gtt gtg        774
Arg Leu Met Leu Met Asp Lys Gly Ile Leu Val His Gly Gly Val Val
        235                 240                 245 gac aaa cat gct act tcc tat gct ttt cac ggg ctg acc cct ggc tac        822
Asp Lys His Ala Thr Ser Tyr Ala Phe His Gly Leu Thr Pro Gly Tyr
    250                 255                 260
```

```
ctc tac aac ctc act gtt atg act gag gct gca ggg ctg caa aac tac      870
Leu Tyr Asn Leu Thr Val Met Thr Glu Ala Ala Gly Leu Gln Asn Tyr
265                 270                 275                 280 agg tgg aaa cta gtc agg aca gcc ccc atg gaa gtc tca aat ctg aag      918
Arg Trp Lys Leu Val Arg Thr Ala Pro Met Glu Val Ser Asn Leu Lys
                285                 290                 295 gtg aca aat gat ggc agt ttg acc tct cta aaa gtc aaa tgg caa aga      966
Val Thr Asn Asp Gly Ser Leu Thr Ser Leu Lys Val Lys Trp Gln Arg
            300                 305                 310 cct cct gga aat gtg gat tct tac aat atc acc ctg tct cac aaa ggg     1014
Pro Pro Gly Asn Val Asp Ser Tyr Asn Ile Thr Leu Ser His Lys Gly
        315                 320                 325 acc atc aag gaa tcc aga gta tta gca cct tgg att act gaa act cac     1062
Thr Ile Lys Glu Ser Arg Val Leu Ala Pro Trp Ile Thr Glu Thr His
330                 335                 340 ttt aaa gag tta gtc ccc ggt cga ctt tat caa gtt act gtc agc tgt     1110
Phe Lys Glu Leu Val Pro Gly Arg Leu Tyr Gln Val Thr Val Ser Cys
345                 350                 355                 360 gtc tct ggt gaa ctg tct gct cag aag atg gca gtg ggc aga aca ttc     1158
Val Ser Gly Glu Leu Ser Ala Gln Lys Met Ala Val Gly Arg Thr Phe
                365                 370                 375 ccc ctg gct gtc ctc cag ctt cgt gtc aaa cat gcc aat gaa acc tca     1206
Pro Leu Ala Val Leu Gln Leu Arg Val Lys His Ala Asn Glu Thr Ser
            380                 385                 390 ctg agt atc atg tgg cag acc cct gta gca gaa tgg gag aaa tac atc     1254
Leu Ser Ile Met Trp Gln Thr Pro Val Ala Glu Trp Glu Lys Tyr Ile
        395                 400                 405 att tcc cta gct gac aga gac ctc tta ctg atc cac aag tca ctc tcc     1302
Ile Ser Leu Ala Asp Arg Asp Leu Leu Leu Ile His Lys Ser Leu Ser
410                 415                 420 aaa gat gcc aaa gaa ttc act ttt act gac ctg gtg cct gga cga aaa     1350
Lys Asp Ala Lys Glu Phe Thr Phe Thr Asp Leu Val Pro Gly Arg Lys
425                 430                 435                 440 tac atg gct aca gtc acc agt att agt gga gac tta aaa aat tcc tct     1398
Tyr Met Ala Thr Val Thr Ser Ile Ser Gly Asp Leu Lys Asn Ser Ser
                445                 450                 455 tca gta aaa gga aga aca gtg cct gcc caa gtg act gac ttg cat gtg     1446
Ser Val Lys Gly Arg Thr Val Pro Ala Gln Val Thr Asp Leu His Val
            460                 465                 470 gcc aac caa gga atg acc agt agt ctg ttt act aac tgg acc cag gca     1494
Ala Asn Gln Gly Met Thr Ser Ser Leu Phe Thr Asn Trp Thr Gln Ala
        475                 480                 485 caa gga gac gta gaa ttt tac caa gtc tta ctg atc cat gaa aat gtg     1542
Gln Gly Asp Val Glu Phe Tyr Gln Val Leu Leu Ile His Glu Asn Val
490                 495                 500 gtc att aaa aat gaa agc atc tcc agt gag acc agc aga tac agc ttc     1590
Val Ile Lys Asn Glu Ser Ile Ser Ser Glu Thr Ser Arg Tyr Ser Phe
505                 510                 515                 520 cac tct ctc aag tcc ggc agc ctg tac tcc gtg gtg gta aca aca gtg     1638
His Ser Leu Lys Ser Gly Ser Leu Tyr Ser Val Val Val Thr Thr Val
                525                 530                 535 agt gga ggg atc tct tcc cga caa gtg gtt gtg gag gga aga aca gtc     1686
Ser Gly Gly Ile Ser Ser Arg Gln Val Val Val Glu Gly Arg Thr Val
            540                 545                 550 cct tcc agt gtg agt gga gta acg gtg aac aat tcc ggt cgt aat gac     1734
Pro Ser Ser Val Ser Gly Val Thr Val Asn Asn Ser Gly Arg Asn Asp
        555                 560                 565 tac ctc agc gtt tcc tgg ctg ctg gcg ccc gga gat gtg gat aac tat     1782
Tyr Leu Ser Val Ser Trp Leu Leu Ala Pro Gly Asp Val Asp Asn Tyr
570                 575                 580
```

-continued

| | | |
|---|---|---|
| gag gta aca ttg tct cat gac ggc aag gtg gtt cag tcc ctt gtc att<br>Glu Val Thr Leu Ser His Asp Gly Lys Val Val Gln Ser Leu Val Ile<br>585                       590                   595                   600 | 1830 |

| gcc aag tct gtc aga gaa tgt tcc ttc agc tcc ctc acc cca ggc cgc | 1878 |
| Ala Lys Ser Val Arg Glu Cys Ser Phe Ser Ser Leu Thr Pro Gly Arg | |
| 605 610 615 | |

| ctc tac acc gtg acc ata act aca agg agt ggc aag tat gaa aat cac | 1926 |
| Leu Tyr Thr Val Thr Ile Thr Thr Arg Ser Gly Lys Tyr Glu Asn His | |
| 620 625 630 | |

| tcc ttc agc caa gag cgg aca gtg cct gac aaa gtc cag gga gtc agt | 1974 |
| Ser Phe Ser Gln Glu Arg Thr Val Pro Asp Lys Val Gln Gly Val Ser | |
| 635 640 645 | |

| gtt agc aac tca gcc agg agt gac tat tta agg gta tcc tgg gtg cat | 2022 |
| Val Ser Asn Ser Ala Arg Ser Asp Tyr Leu Arg Val Ser Trp Val His | |
| 650 655 660 | |

| gcc act gga gac ttt gat cac tat gaa gtc acc att aaa aac aaa aac | 2070 |
| Ala Thr Gly Asp Phe Asp His Tyr Glu Val Thr Ile Lys Asn Lys Asn | |
| 665 670 675 680 | |

| aac ttc att caa act aaa agc att ccc aag tca gaa aac gaa tgt gta | 2118 |
| Asn Phe Ile Gln Thr Lys Ser Ile Pro Lys Ser Glu Asn Glu Cys Val | |
| 685 690 695 | |

| ttt gtt cag cta gtc cct gga cgg ttg tac agt gtc act gtt act aca | 2166 |
| Phe Val Gln Leu Val Pro Gly Arg Leu Tyr Ser Val Thr Val Thr Thr | |
| 700 705 710 | |

| aaa agt gga caa tat gaa gcc aat gaa caa ggg aat ggg aga aca att | 2214 |
| Lys Ser Gly Gln Tyr Glu Ala Asn Glu Gln Gly Asn Gly Arg Thr Ile | |
| 715 720 725 | |

| cca gag cct gtt aag gat cta aca ttg cgc aac agg agc act gag gac | 2262 |
| Pro Glu Pro Val Lys Asp Leu Thr Leu Arg Asn Arg Ser Thr Glu Asp | |
| 730 735 740 | |

| ttg cat gtg act tgg tca gga gct aat ggg gat gtc gac caa tat gag | 2310 |
| Leu His Val Thr Trp Ser Gly Ala Asn Gly Asp Val Asp Gln Tyr Glu | |
| 745 750 755 760 | |

| atc cag ctg ctc ttc aat gac atg aaa gta ttt cct cct ttt cac ctt | 2358 |
| Ile Gln Leu Leu Phe Asn Asp Met Lys Val Phe Pro Pro Phe His Leu | |
| 765 770 775 | |

| gta aat acc gca acc gag tat cga ttt act tcc cta aca cca ggc cgc | 2406 |
| Val Asn Thr Ala Thr Glu Tyr Arg Phe Thr Ser Leu Thr Pro Gly Arg | |
| 780 785 790 | |

| caa tac aaa att ctt gtc ttg acg att agc ggg gat gta cag cag tca | 2454 |
| Gln Tyr Lys Ile Leu Val Leu Thr Ile Ser Gly Asp Val Gln Gln Ser | |
| 795 800 805 | |

| gcc ttc att gag ggc ttc aca gtt cct agt gct gtc aaa aat att cac | 2502 |
| Ala Phe Ile Glu Gly Phe Thr Val Pro Ser Ala Val Lys Asn Ile His | |
| 810 815 820 | |

| att tct ccc aat gga gca aca gat agc ctg acg gtg aac tgg act cct | 2550 |
| Ile Ser Pro Asn Gly Ala Thr Asp Ser Leu Thr Val Asn Trp Thr Pro | |
| 825 830 835 840 | |

| ggt ggg gga gac gtt gat tcc tac acg gtg tcg gca ttc agg cac agt | 2598 |
| Gly Gly Gly Asp Val Asp Ser Tyr Thr Val Ser Ala Phe Arg His Ser | |
| 845 850 855 | |

| caa aag gtt gac tct cag act att ccc aag cac gtc ttt gag cac acg | 2646 |
| Gln Lys Val Asp Ser Gln Thr Ile Pro Lys His Val Phe Glu His Thr | |
| 860 865 870 | |

| ttc cac aga ctg gag gcc ggg gag cag tac cag atc atg att gcc tca | 2694 |
| Phe His Arg Leu Glu Ala Gly Glu Gln Tyr Gln Ile Met Ile Ala Ser | |
| 875 880 885 | |

| gtc agc ggg tcc ctg aag aat cag ata aat gtg gtt ggg cgg aca gtt | 2742 |
| Val Ser Gly Ser Leu Lys Asn Gln Ile Asn Val Val Gly Arg Thr Val | |

-continued

```
            890                 895                 900
cca gca tct gtc caa gga gta att gca gac aat gca tac agc agt tat       2790
Pro Ala Ser Val Gln Gly Val Ile Ala Asp Asn Ala Tyr Ser Ser Tyr
905                 910                 915                 920 tcc tta ata gta agt tgg caa aaa gct gct ggt gtg gca gaa aga tat       2838
Ser Leu Ile Val Ser Trp Gln Lys Ala Ala Gly Val Ala Glu Arg Tyr
                925                 930                 935 gat atc ctg ctt cta act gaa aat gga atc ctt ctg cgc aac aca tca       2886
Asp Ile Leu Leu Leu Thr Glu Asn Gly Ile Leu Leu Arg Asn Thr Ser
                    940                 945                 950 gag cca gcc acc act aag caa cac aaa ttt gaa gat cta aca cca ggc       2934
Glu Pro Ala Thr Thr Lys Gln His Lys Phe Glu Asp Leu Thr Pro Gly
                955                 960                 965 aag aaa tac aag ata cag atc cta act gtc agt gga ggc ctc ttt agc       2982
Lys Lys Tyr Lys Ile Gln Ile Leu Thr Val Ser Gly Gly Leu Phe Ser
970                 975                 980 aag gaa gcc cag act gaa ggc cga aca gtc cca gca gct gtc acc gac       3030
Lys Glu Ala Gln Thr Glu Gly Arg Thr Val Pro Ala Ala Val Thr Asp
985                 990                 995                 1000 ctg agg atc aca gag  aac tcc acc agg cac  ctg tcc ttc cgc tgg         3075
Leu Arg Ile Thr Glu  Asn Ser Thr Arg His  Leu Ser Phe Arg Trp
                1005                 1010                 1015 acc gcc tca gag ggg  gag ctc agc tgg tac  aac atc ttt ttg tac         3120
Thr Ala Ser Glu Gly  Glu Leu Ser Trp Tyr  Asn Ile Phe Leu Tyr
                1020                 1025                 1030 aac cca gat ggg aat  ctc cag gag aga gct  caa gtt gac cca cta         3165
Asn Pro Asp Gly Asn  Leu Gln Glu Arg Ala  Gln Val Asp Pro Leu
                1035                 1040                 1045 gtc cag agc ttc tct  ttc cag aac ttg cta  caa ggc aga atg tac         3210
Val Gln Ser Phe Ser  Phe Gln Asn Leu Leu  Gln Gly Arg Met Tyr
                1050                 1055                 1060 aag atg gtg att gta  act cac agt ggg gag  ctg tct aat gag tct         3255
Lys Met Val Ile Val  Thr His Ser Gly Glu  Leu Ser Asn Glu Ser
                1065                 1070                 1075 ttc ata ttt ggt aga  aca gtc cca gcc tct  gtg agt cat ctc agg         3300
Phe Ile Phe Gly Arg  Thr Val Pro Ala Ser  Val Ser His Leu Arg
                1080                 1085                 1090 ggg tcc aat cgg aac  acg aca gac agc ctt  tgg ttc aac tgg agt         3345
Gly Ser Asn Arg Asn  Thr Thr Asp Ser Leu  Trp Phe Asn Trp Ser
                1095                 1100                 1105 cca gcc tct ggg gac  ttt gac ttt tat gag  ctg att ctc tat aat         3390
Pro Ala Ser Gly Asp  Phe Asp Phe Tyr Glu  Leu Ile Leu Tyr Asn
                1110                 1115                 1120 ccc aat ggc aca aag  aag gaa aac tgg aaa  gac aag gac ctg acg         3435
Pro Asn Gly Thr Lys  Lys Glu Asn Trp Lys  Asp Lys Asp Leu Thr
                1125                 1130                 1135 gag tgg cgg ttt caa  ggc ctt gtt cct gga  agg aag tac gtg ctg         3480
Glu Trp Arg Phe Gln  Gly Leu Val Pro Gly  Arg Lys Tyr Val Leu
                1140                 1145                 1150 tgg gtg gta act cac  agt gga gat ctc agc  aat aaa gtc aca gcg         3525
Trp Val Val Thr His  Ser Gly Asp Leu Ser  Asn Lys Val Thr Ala
                1155                 1160                 1165 gag agc aga aca gct  cca agt cct ccc agt  ctt atg tca ttt gct         3570
Glu Ser Arg Thr Ala  Pro Ser Pro Pro Ser  Leu Met Ser Phe Ala
                1170                 1175                 1180 gac att gca aac aca  tcc ttg gcc atc acg  tgg aaa ggg ccc cca         3615
Asp Ile Ala Asn Thr  Ser Leu Ala Ile Thr  Trp Lys Gly Pro Pro
                1185                 1190                 1195 gac tgg aca gac tac  aac gac ttt gag ctg  cag tgg ttg ccc aga         3660
```

```
                Asp Trp Thr Asp Tyr  Asn Asp Phe Glu Leu  Gln Trp Leu Pro Arg
                                1200                1205               1210 gat gca ctt act gtc  ttc aac ccc tac aac  aac aga aaa tca gaa          3705
Asp Ala Leu Thr Val  Phe Asn Pro Tyr Asn  Asn Arg Lys Ser Glu
                1215                1220                1225 gga cgc att gtg tat  ggt ctt cgt cca ggg  aga tcc tat caa ttc          3750
Gly Arg Ile Val Tyr  Gly Leu Arg Pro Gly  Arg Ser Tyr Gln Phe
                1230                1235                1240 aac gtc aag act gtc  agt ggt gat tcc tgg  aaa act tac agc aaa          3795
Asn Val Lys Thr Val  Ser Gly Asp Ser Trp  Lys Thr Tyr Ser Lys
                1245                1250                1255 cca att ttt gga tct  gtg agg aca aag cct  gac aag ata caa aac          3840
Pro Ile Phe Gly Ser  Val Arg Thr Lys Pro  Asp Lys Ile Gln Asn
                1260                1265                1270 ctg cat tgc cgg cct  cag aac tcc acg gcc  att gcc tgt tct tgg          3885
Leu His Cys Arg Pro  Gln Asn Ser Thr Ala  Ile Ala Cys Ser Trp
                1275                1280                1285 atc cct cct gat tct  gac ttt gat ggt tat  agt att gaa tgc cgg          3930
Ile Pro Pro Asp Ser  Asp Phe Asp Gly Tyr  Ser Ile Glu Cys Arg
                1290                1295                1300 aaa atg gac acc caa  gaa gtt gag ttt tcc  aga aag ctg gag aaa          3975
Lys Met Asp Thr Gln  Glu Val Glu Phe Ser  Arg Lys Leu Glu Lys
                1305                1310                1315 gaa aaa tct ctg ctc  aac atc atg atg cta  gtg ccc cat aag agg          4020
Glu Lys Ser Leu Leu  Asn Ile Met Met Leu  Val Pro His Lys Arg
                1320                1325                1330 tac ctg gtg tcc atc  aaa gtg cag tcg gcc  ggc atg acc agc gag          4065
Tyr Leu Val Ser Ile  Lys Val Gln Ser Ala  Gly Met Thr Ser Glu
                1335                1340                1345 gtg gtt gaa gac agc  act atc aca atg ata  gac cgc ccc cct cct          4110
Val Val Glu Asp Ser  Thr Ile Thr Met Ile  Asp Arg Pro Pro Pro
                1350                1355                1360 cca ccc cca cac att  cgt gtg aat gaa aag  gat gtg cta att agc          4155
Pro Pro Pro His Ile  Arg Val Asn Glu Lys  Asp Val Leu Ile Ser
                1365                1370                1375 aag tct tcc atc aac  ttt act gtc aac tgc  agc tgg ttc agc gac          4200
Lys Ser Ser Ile Asn  Phe Thr Val Asn Cys  Ser Trp Phe Ser Asp
                1380                1385                1390 acc aat gga gct gtg  aaa tac ttc aca gtg  gtg gtg aga gag gct          4245
Thr Asn Gly Ala Val  Lys Tyr Phe Thr Val  Val Val Arg Glu Ala
                1395                1400                1405 gat ggc agt gat gag  ctg aag cca gaa cag  cag cac cct ctc cct          4290
Asp Gly Ser Asp Glu  Leu Lys Pro Glu Gln  Gln His Pro Leu Pro
                1410                1415                1420 tcc tac ctg gag tac  agg cac aat gcc tcc  att cgg gtg tat cag          4335
Ser Tyr Leu Glu Tyr  Arg His Asn Ala Ser  Ile Arg Val Tyr Gln
                1425                1430                1435 act aat tat ttt gcc  agc aaa tgt gcc gaa  aat cct aac agc aac          4380
Thr Asn Tyr Phe Ala  Ser Lys Cys Ala Glu  Asn Pro Asn Ser Asn
                1440                1445                1450 tcc aag agt ttt aac  att aag ctt gga gca  gag atg gag agc cta          4425
Ser Lys Ser Phe Asn  Ile Lys Leu Gly Ala  Glu Met Glu Ser Leu
                1455                1460                1465 ggt gga aaa tgc gat  ccc act cag caa aaa  ttc tgt gat gga cca          4470
Gly Gly Lys Cys Asp  Pro Thr Gln Gln Lys  Phe Cys Asp Gly Pro
                1470                1475                1480 ctg aag cca cac act  gcc tac aga atc agc  att cga gct ttt aca          4515
Leu Lys Pro His Thr  Ala Tyr Arg Ile Ser  Ile Arg Ala Phe Thr
                1485                1490                1495
```

-continued

```
cag ctc ttt gat gag gac ctg aag gaa ttc aca aag cca ctc tat          4560
Gln Leu Phe Asp Glu Asp Leu Lys Glu Phe Thr Lys Pro Leu Tyr
             1500                1505                1510 tca gac aca ttt ttt tct tta ccc atc act act gaa tca gag ccc          4605
Ser Asp Thr Phe Phe Ser Leu Pro Ile Thr Thr Glu Ser Glu Pro
         1515                1520                1525 ttg ttt gga gct att gaa ggt gtg agt gct ggt ctg ttt tta att          4650
Leu Phe Gly Ala Ile Glu Gly Val Ser Ala Gly Leu Phe Leu Ile
     1530                1535                1540 ggc atg cta gtg gct gtt gtt gcc tta ttg atc tgc aga cag aaa          4695
Gly Met Leu Val Ala Val Val Ala Leu Leu Ile Cys Arg Gln Lys
 1545                1550                1555 gtg agc cat ggt cga gaa aga ccc tct gcc cgt ctg agc att cgt          4740
Val Ser His Gly Arg Glu Arg Pro Ser Ala Arg Leu Ser Ile Arg
             1560                1565                1570 agg gat cga cca tta tct gtc cac tta aac ctg ggc cag aaa ggt          4785
Arg Asp Arg Pro Leu Ser Val His Leu Asn Leu Gly Gln Lys Gly
         1575                1580                1585 aac cgg aaa act tct tgt cca ata aaa ata aat cag ttt gaa ggg          4830
Asn Arg Lys Thr Ser Cys Pro Ile Lys Ile Asn Gln Phe Glu Gly
     1590                1595                1600 cat ttc atg aag cta cag gct gac tcc aac tac ctt cta tcc aag          4875
His Phe Met Lys Leu Gln Ala Asp Ser Asn Tyr Leu Leu Ser Lys
 1605                1610                1615 gaa tac gag gag tta aaa gac gtg ggc cga aac cag tca tgt gac          4920
Glu Tyr Glu Glu Leu Lys Asp Val Gly Arg Asn Gln Ser Cys Asp
             1620                1625                1630 att gca ctc ttg ccg gag aat aga ggg aaa aat cga tac aac aat          4965
Ile Ala Leu Leu Pro Glu Asn Arg Gly Lys Asn Arg Tyr Asn Asn
         1635                1640                1645 ata ttg ccc tat gat gcc acg cga gtg aag ctc tcc aat gta gat          5010
Ile Leu Pro Tyr Asp Ala Thr Arg Val Lys Leu Ser Asn Val Asp
     1650                1655                1660 gat gat cct tgc tct gac tac atc aat gcc agc tac atc cct ggc          5055
Asp Asp Pro Cys Ser Asp Tyr Ile Asn Ala Ser Tyr Ile Pro Gly
 1665                1670                1675 aac aac ttc aga aga gaa tac att gtc act cag gga ccg ctt cct          5100
Asn Asn Phe Arg Arg Glu Tyr Ile Val Thr Gln Gly Pro Leu Pro
             1680                1685                1690 ggc acc aag gat gac ttc tgg aaa atg gtg tgg gaa caa aac gtt          5145
Gly Thr Lys Asp Asp Phe Trp Lys Met Val Trp Glu Gln Asn Val
         1695                1700                1705 cac aac atc gtc atg gtg acc cag tgt gtt gag aag ggc cga gta          5190
His Asn Ile Val Met Val Thr Gln Cys Val Glu Lys Gly Arg Val
     1710                1715                1720 aag tgt gac cat tac tgg cca gcg gac cag gat tcc ctc tac tat          5235
Lys Cys Asp His Tyr Trp Pro Ala Asp Gln Asp Ser Leu Tyr Tyr
 1725                1730                1735 ggg gac ctc atc ctg cag atg ctc tca gag tcc gtc ctg cct gag          5280
Gly Asp Leu Ile Leu Gln Met Leu Ser Glu Ser Val Leu Pro Glu
             1740                1745                1750 tgg acc atc cgg gag ttt aag ata tgc ggt gag gaa cag ctt gat          5325
Trp Thr Ile Arg Glu Phe Lys Ile Cys Gly Glu Glu Gln Leu Asp
         1755                1760                1765 gca cac aga ctc atc cgc cac ttt cac tat acg gtg tgg cca gac          5370
Ala His Arg Leu Ile Arg His Phe His Tyr Thr Val Trp Pro Asp
     1770                1775                1780 cat gga gtc cca gaa acc acc cag tct ctg atc cag ttt gtg aga          5415
His Gly Val Pro Glu Thr Thr Gln Ser Leu Ile Gln Phe Val Arg
 1785                1790                1795
```

```
act gtc agg gac tac atc aac aga agc ccg ggt gct ggg ccc act      5460
Thr Val Arg Asp Tyr Ile Asn Arg Ser Pro Gly Ala Gly Pro Thr
            1800                1805                1810 gtg gtg cac tgc agt gct ggt gtg ggt agg act gga acc ttt att      5505
Val Val His Cys Ser Ala Gly Val Gly Arg Thr Gly Thr Phe Ile
            1815                1820                1825 gca ttg gac cga atc ctc cag cag tta gac tcc aaa gac tct gtg      5550
Ala Leu Asp Arg Ile Leu Gln Gln Leu Asp Ser Lys Asp Ser Val
            1830                1835                1840 gac att tat gga gca gtg cac gac cta aga ctt cac agg gtt cac      5595
Asp Ile Tyr Gly Ala Val His Asp Leu Arg Leu His Arg Val His
            1845                1850                1855 atg gtc cag act gag tgt cag tat gtc tac cta cat cag tgt gta      5640
Met Val Gln Thr Glu Cys Gln Tyr Val Tyr Leu His Gln Cys Val
            1860                1865                1870 aga gat gtc ctc aga gca aga aag cta cgg agt gaa caa gaa aac      5685
Arg Asp Val Leu Arg Ala Arg Lys Leu Arg Ser Glu Gln Glu Asn
            1875                1880                1885 ccc ttg ttt cca atc tat gaa aat gtg aat cca gag tat cac aga      5730
Pro Leu Phe Pro Ile Tyr Glu Asn Val Asn Pro Glu Tyr His Arg
            1890                1895                1900 gat cca gtc tat tca agg cat tga gaatgtacct gaagagctcc tggataaaaa  5784
Asp Pro Val Tyr Ser Arg His
            1905 ttattcactg tgtgatttgt ttttaaaaac ttgcttcatg ccctacagag gtgccagcta 5844 tttctgttga tactatgtat aatttattaa tctggagaat gtntaaaant ntatataatt 5904 taaaggtaac agatattatt gtacatagtt gtattttgta gtttcttctg taaatatgta 5964 tttttcata atgtttaata ttaagcttta tataatacta ttttcacac taaaaaaaaa  6024 aaaaaaaaa                                                         6033

<210> SEQ ID NO 15
<211> LENGTH: 1907
<212> TYPE: PRT
<213> ORGANISM: Homo sapiens

<400> SEQUENCE: 15

Met Leu Ser His Gly Ala Gly Leu Ala Leu Trp Ile Thr Leu Ser Leu
1               5                   10                  15

Leu Gln Thr Gly Leu Ala Glu Pro Glu Arg Cys Asn Phe Thr Leu Ala
                20                  25                  30

Glu Ser Lys Ala Ser Ser His Ser Val Ser Ile Gln Trp Arg Ile Leu
            35                  40                  45

Gly Ser Pro Cys Asn Phe Ser Leu Ile Tyr Ser Ser Asp Thr Leu Gly
        50                  55                  60

Ala Ala Leu Cys Pro Thr Phe Arg Ile Asp Asn Thr Thr Tyr Gly Cys
65                  70                  75                  80

Asn Leu Gln Asp Leu Gln Ala Gly Thr Ile Tyr Asn Phe Lys Ile Ile
                85                  90                  95

Ser Leu Asp Glu Glu Arg Thr Val Val Leu Gln Thr Asp Pro Leu Pro
            100                 105                 110

Pro Ala Arg Phe Gly Val Ser Lys Glu Lys Thr Thr Ser Thr Gly Leu
        115                 120                 125

His Val Trp Trp Thr Pro Ser Ser Gly Lys Val Thr Ser Tyr Glu Val
    130                 135                 140

Gln Leu Phe Asp Glu Asn Asn Gln Lys Ile Gln Gly Val Gln Ile Gln
```

-continued

```
            145                 150                 155                 160
        Glu Ser Thr Ser Trp Asn Glu Tyr Thr Phe Phe Asn Leu Thr Ala Gly
                        165                 170                 175
        Ser Lys Tyr Asn Ile Ala Ile Thr Ala Val Ser Gly Gly Lys Arg Ser
                        180                 185                 190
        Phe Ser Val Tyr Thr Asn Gly Ser Thr Val Pro Ser Pro Val Lys Asp
                        195                 200                 205
        Ile Gly Ile Ser Thr Lys Ala Asn Ser Leu Leu Ile Ser Trp Ser His
                210                 215                 220
        Gly Ser Gly Asn Val Glu Arg Tyr Arg Leu Met Leu Met Asp Lys Gly
        225                 230                 235                 240
        Ile Leu Val His Gly Val Val Asp Lys His Ala Thr Ser Tyr Ala
                        245                 250                 255
        Phe His Gly Leu Thr Pro Gly Tyr Leu Tyr Asn Leu Thr Val Met Thr
                        260                 265                 270
        Glu Ala Ala Gly Leu Gln Asn Tyr Arg Trp Lys Leu Val Arg Thr Ala
                        275                 280                 285
        Pro Met Glu Val Ser Asn Leu Lys Val Thr Asn Asp Gly Ser Leu Thr
                290                 295                 300
        Ser Leu Lys Val Lys Trp Gln Arg Pro Pro Gly Asn Val Asp Ser Tyr
        305                 310                 315                 320
        Asn Ile Thr Leu Ser His Lys Gly Thr Ile Lys Glu Ser Arg Val Leu
                        325                 330                 335
        Ala Pro Trp Ile Thr Glu Thr His Phe Lys Glu Leu Val Pro Gly Arg
                        340                 345                 350
        Leu Tyr Gln Val Thr Val Ser Cys Val Ser Gly Glu Leu Ser Ala Gln
                        355                 360                 365
        Lys Met Ala Val Gly Arg Thr Phe Pro Leu Ala Val Leu Gln Leu Arg
                370                 375                 380
        Val Lys His Ala Asn Glu Thr Ser Leu Ser Ile Met Trp Gln Thr Pro
        385                 390                 395                 400
        Val Ala Glu Trp Glu Lys Tyr Ile Ile Ser Leu Ala Asp Arg Asp Leu
                        405                 410                 415
        Leu Leu Ile His Lys Ser Leu Ser Lys Asp Ala Lys Glu Phe Thr Phe
                        420                 425                 430
        Thr Asp Leu Val Pro Gly Arg Lys Tyr Met Ala Thr Val Thr Ser Ile
                        435                 440                 445
        Ser Gly Asp Leu Lys Asn Ser Ser Val Lys Gly Arg Thr Val Pro
                450                 455                 460
        Ala Gln Val Thr Asp Leu His Val Ala Asn Gln Gly Met Thr Ser Ser
        465                 470                 475                 480
        Leu Phe Thr Asn Trp Thr Gln Ala Gln Gly Asp Val Glu Phe Tyr Gln
                        485                 490                 495
        Val Leu Leu Ile His Glu Asn Val Val Ile Lys Asn Glu Ser Ile Ser
                        500                 505                 510
        Ser Glu Thr Ser Arg Tyr Ser Phe His Ser Leu Lys Ser Gly Ser Leu
                        515                 520                 525
        Tyr Ser Val Val Thr Thr Val Ser Gly Gly Ile Ser Ser Arg Gln
                530                 535                 540
        Val Val Val Glu Gly Arg Thr Val Pro Ser Ser Val Ser Gly Val Thr
        545                 550                 555                 560
        Val Asn Asn Ser Gly Arg Asn Asp Tyr Leu Ser Val Ser Trp Leu Leu
                        565                 570                 575
```

-continued

```
Ala Pro Gly Asp Val Asp Asn Tyr Glu Val Thr Leu Ser His Asp Gly
            580                 585                 590

Lys Val Val Gln Ser Leu Val Ile Ala Lys Ser Val Arg Glu Cys Ser
        595                 600                 605

Phe Ser Ser Leu Thr Pro Gly Arg Leu Tyr Thr Val Thr Ile Thr Thr
        610                 615                 620

Arg Ser Gly Lys Tyr Glu Asn His Ser Phe Ser Gln Glu Arg Thr Val
625                 630                 635                 640

Pro Asp Lys Val Gln Gly Val Ser Val Ser Asn Ser Ala Arg Ser Asp
                645                 650                 655

Tyr Leu Arg Val Ser Trp Val His Ala Thr Gly Asp Phe Asp His Tyr
            660                 665                 670

Glu Val Thr Ile Lys Asn Lys Asn Phe Ile Gln Thr Lys Ser Ile
        675                 680                 685

Pro Lys Ser Glu Asn Glu Cys Val Phe Val Gln Leu Val Pro Gly Arg
        690                 695                 700

Leu Tyr Ser Val Thr Val Thr Thr Lys Ser Gly Gln Tyr Glu Ala Asn
705                 710                 715                 720

Glu Gln Gly Asn Gly Arg Thr Ile Pro Glu Pro Val Lys Asp Leu Thr
                725                 730                 735

Leu Arg Asn Arg Ser Thr Glu Asp Leu His Val Thr Trp Ser Gly Ala
            740                 745                 750

Asn Gly Asp Val Asp Gln Tyr Glu Ile Gln Leu Leu Phe Asn Asp Met
        755                 760                 765

Lys Val Phe Pro Pro Phe His Leu Val Asn Thr Ala Thr Glu Tyr Arg
770                 775                 780

Phe Thr Ser Leu Thr Pro Gly Arg Gln Tyr Lys Ile Leu Val Leu Thr
785                 790                 795                 800

Ile Ser Gly Asp Val Gln Gln Ser Ala Phe Ile Glu Gly Phe Thr Val
                805                 810                 815

Pro Ser Ala Val Lys Asn Ile His Ile Ser Pro Asn Gly Ala Thr Asp
            820                 825                 830

Ser Leu Thr Val Asn Trp Thr Pro Gly Gly Gly Asp Val Asp Ser Tyr
        835                 840                 845

Thr Val Ser Ala Phe Arg His Ser Gln Lys Val Asp Ser Gln Thr Ile
    850                 855                 860

Pro Lys His Val Phe Glu His Thr Phe His Arg Leu Glu Ala Gly Glu
865                 870                 875                 880

Gln Tyr Gln Ile Met Ile Ala Ser Val Ser Gly Ser Leu Lys Asn Gln
                885                 890                 895

Ile Asn Val Val Gly Arg Thr Val Pro Ala Ser Val Gln Gly Val Ile
            900                 905                 910

Ala Asp Asn Ala Tyr Ser Ser Tyr Ser Leu Ile Val Ser Trp Gln Lys
        915                 920                 925

Ala Ala Gly Val Ala Glu Arg Tyr Asp Ile Leu Leu Leu Thr Glu Asn
    930                 935                 940

Gly Ile Leu Leu Arg Asn Thr Ser Glu Pro Ala Thr Thr Lys Gln His
945                 950                 955                 960

Lys Phe Glu Asp Leu Thr Pro Gly Lys Lys Tyr Lys Ile Gln Ile Leu
                965                 970                 975

Thr Val Ser Gly Gly Leu Phe Ser Lys Glu Ala Gln Thr Glu Gly Arg
            980                 985                 990
```

-continued

```
Thr Val Pro Ala Ala Val Thr Asp  Leu Arg Ile Thr Glu  Asn Ser Thr
        995              1000              1005

Arg His Leu Ser Phe Arg Trp  Thr Ala Ser Glu Gly  Glu Leu Ser
    1010             1015              1020

Trp Tyr Asn Ile Phe Leu Tyr  Asn Pro Asp Gly Asn  Leu Gln Glu
    1025             1030              1035

Arg Ala Gln Val Asp Pro Leu  Val Gln Ser Phe Ser  Phe Gln Asn
    1040             1045              1050

Leu Leu Gln Gly Arg Met Tyr  Lys Met Val Ile Val  Thr His Ser
    1055             1060              1065

Gly Glu Leu Ser Asn Glu Ser  Phe Ile Phe Gly Arg  Thr Val Pro
    1070             1075              1080

Ala Ser Val Ser His Leu Arg  Gly Ser Asn Arg Asn  Thr Thr Asp
    1085             1090              1095

Ser Leu Trp Phe Asn Trp Ser  Pro Ala Ser Gly Asp  Phe Asp Phe
    1100             1105              1110

Tyr Glu Leu Ile Leu Tyr Asn  Pro Asn Gly Thr Lys  Lys Glu Asn
    1115             1120              1125

Trp Lys Asp Lys Asp Leu Thr  Glu Trp Arg Phe Gln  Gly Leu Val
    1130             1135              1140

Pro Gly Arg Lys Tyr Val Leu  Trp Val Val Thr His  Ser Gly Asp
    1145             1150              1155

Leu Ser Asn Lys Val Thr Ala  Glu Ser Arg Thr Ala  Pro Ser Pro
    1160             1165              1170

Pro Ser Leu Met Ser Phe Ala  Asp Ile Ala Asn Thr  Ser Leu Ala
    1175             1180              1185

Ile Thr Trp Lys Gly Pro Pro  Asp Trp Thr Asp Tyr  Asn Asp Phe
    1190             1195              1200

Glu Leu Gln Trp Leu Pro Arg  Asp Ala Leu Thr Val  Phe Asn Pro
    1205             1210              1215

Tyr Asn Asn Arg Lys Ser Glu  Gly Arg Ile Val Tyr  Gly Leu Arg
    1220             1225              1230

Pro Gly Arg Ser Tyr Gln Phe  Asn Val Lys Thr Val  Ser Gly Asp
    1235             1240              1245

Ser Trp Lys Thr Tyr Ser Lys  Pro Ile Phe Gly Ser  Val Arg Thr
    1250             1255              1260

Lys Pro Asp Lys Ile Gln Asn  Leu His Cys Arg Pro  Gln Asn Ser
    1265             1270              1275

Thr Ala Ile Ala Cys Ser Trp  Ile Pro Pro Asp Ser  Asp Phe Asp
    1280             1285              1290

Gly Tyr Ser Ile Glu Cys Arg  Lys Met Asp Thr Gln  Glu Val Glu
    1295             1300              1305

Phe Ser Arg Lys Leu Glu Lys  Glu Lys Ser Leu Leu  Asn Ile Met
    1310             1315              1320

Met Leu Val Pro His Lys Arg  Tyr Leu Val Ser Ile  Lys Val Gln
    1325             1330              1335

Ser Ala Gly Met Thr Ser Glu  Val Val Glu Asp Ser  Thr Ile Thr
    1340             1345              1350

Met Ile Asp Arg Pro Pro Pro  Pro Pro Pro His Ile  Arg Val Asn
    1355             1360              1365

Glu Lys Asp Val Leu Ile Ser  Lys Ser Ser Ile Asn  Phe Thr Val
    1370             1375              1380

Asn Cys Ser Trp Phe Ser Asp  Thr Asn Gly Ala Val  Lys Tyr Phe
```

-continued

```
        1385                1390                1395
Thr Val Val Val Arg Glu Ala Asp Gly Ser Asp Glu Leu Lys Pro
    1400                1405                1410
Glu Gln Gln His Pro Leu Pro Ser Tyr Leu Glu Tyr Arg His Asn
    1415                1420                1425
Ala Ser Ile Arg Val Tyr Gln Thr Asn Tyr Phe Ala Ser Lys Cys
    1430                1435                1440
Ala Glu Asn Pro Asn Ser Asn Ser Lys Ser Phe Asn Ile Lys Leu
    1445                1450                1455
Gly Ala Glu Met Glu Ser Leu Gly Gly Lys Cys Asp Pro Thr Gln
    1460                1465                1470
Gln Lys Phe Cys Asp Gly Pro Leu Lys Pro His Thr Ala Tyr Arg
    1475                1480                1485
Ile Ser Ile Arg Ala Phe Thr Gln Leu Phe Asp Glu Asp Leu Lys
    1490                1495                1500
Glu Phe Thr Lys Pro Leu Tyr Ser Asp Thr Phe Phe Ser Leu Pro
    1505                1510                1515
Ile Thr Thr Glu Ser Glu Pro Leu Phe Gly Ala Ile Glu Gly Val
    1520                1525                1530
Ser Ala Gly Leu Phe Leu Ile Gly Met Leu Val Ala Val Val Ala
    1535                1540                1545
Leu Leu Ile Cys Arg Gln Lys Val Ser His Gly Arg Glu Arg Pro
    1550                1555                1560
Ser Ala Arg Leu Ser Ile Arg Arg Asp Arg Pro Leu Ser Val His
    1565                1570                1575
Leu Asn Leu Gly Gln Lys Gly Asn Arg Lys Thr Ser Cys Pro Ile
    1580                1585                1590
Lys Ile Asn Gln Phe Glu Gly His Phe Met Lys Leu Gln Ala Asp
    1595                1600                1605
Ser Asn Tyr Leu Leu Ser Lys Glu Tyr Glu Glu Leu Lys Asp Val
    1610                1615                1620
Gly Arg Asn Gln Ser Cys Asp Ile Ala Leu Leu Pro Glu Asn Arg
    1625                1630                1635
Gly Lys Asn Arg Tyr Asn Asn Ile Leu Pro Tyr Asp Ala Thr Arg
    1640                1645                1650
Val Lys Leu Ser Asn Val Asp Asp Pro Cys Ser Asp Tyr Ile
    1655                1660                1665
Asn Ala Ser Tyr Ile Pro Gly Asn Asn Phe Arg Arg Glu Tyr Ile
    1670                1675                1680
Val Thr Gln Gly Pro Leu Pro Gly Thr Lys Asp Asp Phe Trp Lys
    1685                1690                1695
Met Val Trp Glu Gln Asn Val His Asn Ile Val Met Val Thr Gln
    1700                1705                1710
Cys Val Glu Lys Gly Arg Val Lys Cys Asp His Tyr Trp Pro Ala
    1715                1720                1725
Asp Gln Asp Ser Leu Tyr Tyr Gly Asp Leu Ile Leu Gln Met Leu
    1730                1735                1740
Ser Glu Ser Val Leu Pro Glu Trp Thr Ile Arg Glu Phe Lys Ile
    1745                1750                1755
Cys Gly Glu Glu Gln Leu Asp Ala His Arg Leu Ile Arg His Phe
    1760                1765                1770
His Tyr Thr Val Trp Pro Asp His Gly Val Pro Glu Thr Thr Gln
    1775                1780                1785
```

-continued

```
Ser Leu Ile Gln Phe Val Arg Thr Val Arg Asp Tyr Ile Asn Arg
    1790                1795                1800

Ser Pro Gly Ala Gly Pro Thr Val Val His Cys Ser Ala Gly Val
    1805                1810                1815

Gly Arg Thr Gly Thr Phe Ile Ala Leu Asp Arg Ile Leu Gln Gln
    1820                1825                1830

Leu Asp Ser Lys Asp Ser Val Asp Ile Tyr Gly Ala Val His Asp
    1835                1840                1845

Leu Arg Leu His Arg Val His Met Val Gln Thr Glu Cys Gln Tyr
    1850                1855                1860

Val Tyr Leu His Gln Cys Val Arg Asp Val Leu Arg Ala Arg Lys
    1865                1870                1875

Leu Arg Ser Glu Gln Glu Asn Pro Leu Phe Pro Ile Tyr Glu Asn
    1880                1885                1890

Val Asn Pro Glu Tyr His Arg Asp Pro Val Tyr Ser Arg His
    1895                1900                1905

<210> SEQ ID NO 16
<211> LENGTH: 319
<212> TYPE: PRT
<213> ORGANISM: Homo sapiens

<400> SEQUENCE: 16

Gly Asp Arg Pro Leu Ser Val His Leu Asn Leu Gly Gln Lys Gly Asn
1               5                   10                  15

Arg Lys Thr Ser Cys Pro Ile Lys Ile Asn Gln Phe Glu Gly His Phe
                20                  25                  30

Met Lys Leu Gln Ala Asp Ser Asn Tyr Leu Leu Ser Lys Glu Tyr Glu
            35                  40                  45

Glu Leu Lys Asp Val Gly Arg Asn Gln Ser Cys Asp Ile Ala Leu Leu
        50                  55                  60

Pro Glu Asn Arg Gly Lys Asn Arg Tyr Asn Asn Ile Leu Pro Tyr Asp
65                  70                  75                  80

Ala Thr Arg Val Lys Leu Ser Asn Val Asp Asp Pro Cys Ser Asp
                85                  90                  95

Tyr Ile Asn Ala Ser Tyr Ile Pro Gly Asn Asn Phe Arg Arg Glu Tyr
            100                 105                 110

Ile Val Thr Gln Gly Pro Leu Pro Gly Thr Lys Asp Asp Phe Trp Lys
        115                 120                 125

Met Val Trp Glu Gln Asn Val His Asn Ile Val Met Val Thr Gln Cys
130                 135                 140

Val Glu Lys Gly Arg Val Lys Cys Asp His Tyr Trp Pro Ala Asp Gln
145                 150                 155                 160

Asp Ser Leu Tyr Tyr Gly Asp Leu Ile Leu Gln Met Leu Ser Glu Ser
                165                 170                 175

Val Leu Pro Glu Trp Thr Ile Arg Glu Phe Lys Ile Cys Gly Glu Glu
            180                 185                 190

Gln Leu Asp Ala His Arg Leu Ile Arg His Phe His Tyr Thr Val Trp
        195                 200                 205

Pro Asp His Gly Val Pro Glu Thr Thr Gln Ser Leu Ile Gln Phe Val
    210                 215                 220

Arg Thr Val Arg Asp Tyr Ile Asn Arg Ser Pro Gly Ala Gly Pro Thr
225                 230                 235                 240

Val Val His Cys Ser Ala Gly Val Gly Arg Thr Gly Thr Phe Ile Ala
```

-continued

```
                 245                 250                 255
Leu Asp Arg Ile Leu Gln Gln Leu Asp Ser Lys Asp Ser Val Asp Ile
            260                 265                 270

Tyr Gly Ala Val His Asp Leu Arg Leu His Arg Val His Met Val Gln
        275                 280                 285

Thr Glu Cys Gln Tyr Val Tyr Leu His Gln Cys Val Arg Asp Val Leu
    290                 295                 300

Arg Ala Arg Lys Leu Arg Ser Glu Gln His His His His His His
305                 310                 315

<210> SEQ ID NO 17
<211> LENGTH: 25
<212> TYPE: DNA
<213> ORGANISM: Homo sapiens

<400> SEQUENCE: 17
gttagggaag taaatcgata ctggg                                       25
```

PHARMACEUTICAL COMPOSITIONS THAT MODULATE HPTPBETA ACTIVITY

CROSS REFERENCE TO RELATED APPLICATIONS

This application is a divisional of U.S. Ser. No. 10/633,742 (U.S. Pat. No. 7,226,755), filed 4 Aug. 2003, which in turn, claims priority, as does this application, under Title 35 U.S. Code 119(e) from Provisional Application Ser. No. 60/413,547 filed Sep. 25, 2002, which is herein incorporated by reference in its entirety.

FIELD OF INVENTION

This invention is directed to the use of HPTPbeta to screen agents useful in the treatment angiogenesis mediated disorders.

BACKGROUND OF THE INVENTION

Angiogenesis, the sprouting of new blood vessels from the pre-existing vasculature, plays a crucial role in a wide range of physiological and pathological processes (Nguyen, L. L. et al, Int. Rev. Cytol. 204, 1-48, (2001). It is a complex process that is mediated by communication between the endothelial cells that line blood vessels and their surrounding environment. In the early stages of angiogenesis, tissue or tumor cells produce and secrete pro-angiogenic growth factors in response to environmental stimuli. These factors diffuse to nearby endothelial cells and stimulate receptors that lead to the production and secretion of proteases that degrade the surrounding extracellular matrix (Stetler-Stevenson, W. G., Surg. Oncol. Clin. N. Am. 10, 383-392, (2001). These activated endothelial cells begin to migrate and proliferate into the surrounding tissue toward the source of these factors. Endothelial cells then stop proliferating and differentiate into tubular structures, which is the first step in the formation of stable, mature blood vessels. Subsequently, periendothelial cells, such as pericytes and smooth muscle cells, are recruited to the newly formed vessel in a further step toward vessel maturation.

There are many disease states driven by unregulated angiogenesis that can either cause a particular disease directly or exacerbate an existing pathological condition. For example, ocular neovascularization has been implicated as the most common cause of blindness and underlies the pathology of approximately 20 eye diseases. In certain previously existing conditions such as arthritis, newly formed capillary blood vessels invade the joints and destroy cartilage. In diabetes, new capillaries formed in the retina invade the vitreous humor, causing bleeding and blindness.

On the other hand, tissue growth and repair are biologic systems wherein cellular proliferation and angiogenesis occur. Thus an important aspect of wound repair is the revascularization of damaged tissue by angiogenesis. Atherosclerotic lesions in large vessels can cause tissue ischemia that could be ameliorated by modulating blood vessel growth to the affected tissue. For example, atherosclerotic lesions in the coronary arteries cause angina and myocardial infarction that could be prevented if one could restore blood flow by stimulating the growth of collateral arteries. Similarly, atherosclerotic lesions in the large arteries that supply the legs cause ischemia in the skeletal muscle that limits mobility that could also be prevented by improving blood flow with angiogenic therapy.

In view of the foregoing, there is a need to identify biochemical targets in the treatment of angiogenesis mediated disorders. However, angiogenesis involves the action of multiple growth factors and their cognate receptor tyrosine kinases (RTKs), Yancopoulos et al., Nature, 407,242-248, 2000). Vascular endothelial growth factor (VEGF), for example, is critical for the differentiation of endothelial cells into nascent blood vessels in the embryonic vasculature. Further, VEGF enhances blood vessel development in the adult vasculature. Administration of exogenous VEGF enhances the development of the collateral vasculature and improves blood flow to ischemic tissues.

To date, three VEGF RTKs have been identified, VEGFR1 (FLT-1), VEGFR2 (KDR), and VEGFR3 (FLT-4). Although these receptors are highly conserved, based on biochemical characterization and biological activity, each has specific and non-overlapping functions. Of the three receptors, VEGFR2 plays the predominant role in mediating VEGF actions in the developing vasculature and during angiogenesis in adults. However, both VEGFR1 and VEGFR3 are required for normal development of the embryonic vasculature and may also be important for angiogenesis in adult tissues. Upon VEGF binding and dimerization, a conformational change in the VEGFR2 kinase domain enhances its kinase activity resulting in "autophosphorylation" of the other member of the pair on specific tyrosine residues. These autophosphorylation events serve to further enhance the kinase activity and provide anchor points for the association of intracellular signaling molecules.

However, activation of a single angiogenic pathway may not be sufficient to produce persistent and functional vessels that provide adequate perfusion to ischemic tissue. These findings, together with fact that multiple RTKs are involved in the assembly of embryonic vasculature, indicate that biochemical targets that modulate multiple angiogenic pathways will have advantages over administration of a single growth factor.

Protein tyrosine phosphatases (PTPs) comprise a large family of closely related enzymes that dephosphorylate proteins that contain phosphotyrosine residues. Recent evidence suggests that one function of PTPs is to limit the phosphorylation and activation of RTKs. For example, HCPTPA, a low molecular weight protein tyrosine phosphatase, was shown to associate with VEGFR2 and negatively regulate its activation in cultured endothelial cells and its biological activity in angiogenesis assays, (Huang et al., Journal of Biological Chemistry, 274, 38183-38185, 1999). Whether or not other PTPs might regulate VEGFR2 activation is not known.

In addition to VEGFR2, signaling input from another RTK Tie-2, the receptor for the angiopoietins (Ang1 and Ang2), is also essential. Deletion of either Ang1 or Tie-2 gene in mice results in embryonic lethality secondary to abnormalities in the developing vasculature (Yancopoulos et al., Nature, 407, 242-248, 2000). In addition, overexpression of Ang1 in the skin increases skin vascularity and administration of exogenous Ang1 increases blood flow to ischemic skeletal muscle (Suri et al., Science, 282, 468-471, 1998). Moreover, inhibiting the activation of Tie-2 inhibits angiogenesis and limits tumor progression in animal models of cancer, (Lin et al., JCI, 100, 2072-2078, 1997). In addition to its angiogenic activities, activation of Tie-2 by exogenous administration of Ang1 blocks VEGF mediated vascular leak and pro-inflammatory effects, but enhances its angiogenic effects (Thurston et al., Nature Medicine, 6, 460-463, 2000). Therefore, biological targets that modulate both VEGFR2 and Tie-2 signaling may yield superior proangiogenic or antiangiogenic therapies.

SUMMARY OF THE INVENTION

The present invention is based, in part, on the discovery that modulation of HPTPbeta activity modulates the activation and the biological activity of both VEGFR2 and Tie-2. As such, the present invention identifies and provides HPTPbeta as a target to identify agents useful in the treatment of angiogenesis mediated disorders.

In one aspect, the invention provides for a method of identifying an agent useful for modulating angiogenesis comprising the steps of: (a) exposing HPTPbeta to an agent; (b) measuring activity of HPTPbeta, wherein modulation of HPTPbeta activity indicates the agent is useful for modulating angiogenesis.

In another aspect, the invention provides for a method of identifying an agent useful for modulating angiogenesis comprising the steps of: (a) exposing HPTPbeta to an agent to form HPTPbeta/agent complex; (b) exposing the HPTPbeta/agent complex to VEGFR2; and (c) measuring the activity of VEGFR2; wherein a modulation in VEGFR2 activity indicates the agent is useful for modulating angiogenesis.

In another aspect, the invention provides for a method of identifying an agent useful for modulating angiogenesis comprising the steps of: (a) exposing HPTPbeta to an agent; (b) exposing HPTPbeta/agent complex to VEGFR2 and Tie-2; and (c) measuring the activity of VEGFR2 and/or Tie-2; wherein a modulation in VEGFR2 and/or Tie-2 activity indicates the agent is useful for modulating angiogenesis.

The above-described embodiments may be performed in vitro, either in cell free or cell-based assays; or in vivo, or ex vivo using tissue implants.

SEQUENCE LISTING DESCRIPTION

Figure 1:
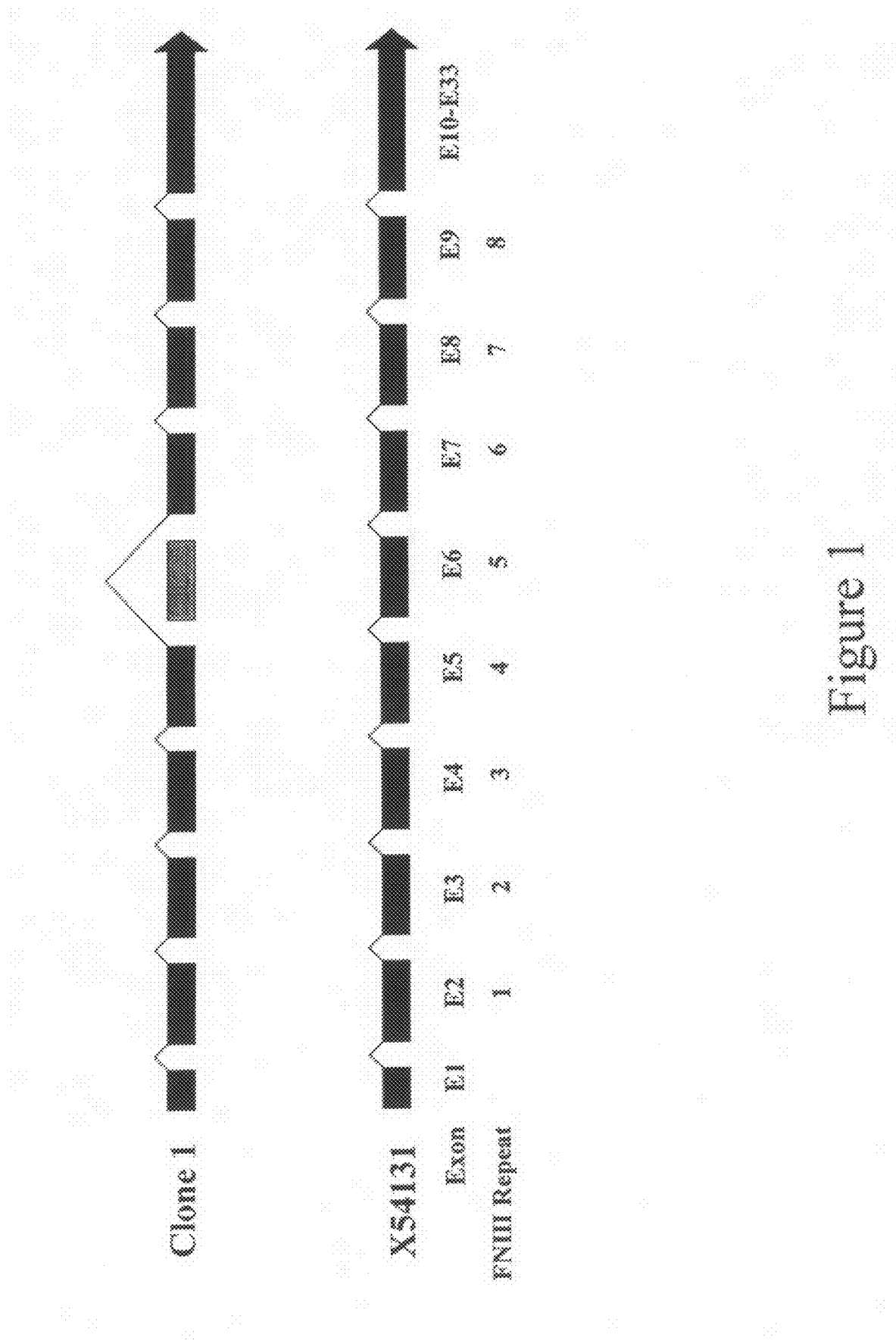
FIG. 1. Schematic representation of the 5' end of the HPT-Pbeta gene showing that the missing exon codes for FNIII repeat 5 compared to Genbank entry X54131.

Each of the nucleotide and protein sequences in the sequence listing, along with the corresponding Genbank or Derwent accession number(s) and animal species from which it is cloned, is shown in Table I.

tions are well known in the art. For example, variants can be prepared by mutations in the nucleotide sequence. Methods for mutagenesis and nucleotide sequence alterations are well known in the art. See, for example, Current Protocols in Molecular Biology (and updates) Ausubel et al. Eds. (1996), John Wiley and Sons, New York; Methods in Molecular Biology, vol 182, In vitro Mutagenesis Protocols, $2^{nd}$ Edition, Barman Ed. (2002), Humana Press), and the references cited therein. In one embodiment, the substitution of the amino acid is conservative in that it minimally alters the biochemical properties of the variant. In other embodiments, the variant may be an active or inactive fragment of a full-length protein, a post-translationally or chemically modified protein, a protein modified by addition of affinity or epitope tags, or fluorescent or other labeling, whether accomplished by in vivo or in vitro enzymatic treatment of the protein, by chemical modification, or by the synthesis of the protein using modified amino acids. Non-limiting examples of modifications to amino acids include phosphorylation of tyrosine, serine, and

TABLE I

| Sequence Description | SEQ ID NO: Nucleotide, Amino Acid | Species | Genbank (GB) or Derwent (D) Accession No. for Nucleotide Sequence | Related Genbank (GB) or Derwent (D) Accession Nos. |
|---|---|---|---|---|
| HPTPβ (HPTP-Beta, PTPRB, PTPβ, PTPB, R-PTP-Beta) | 1, 2 | Homo Sapiens | X54131 | NM_002837 |
| mRPTPB (VE-PTP, R-PTP-Beta, mPTP-Beta) | 3, 4 | Mus Musculus | X58289 | AF157628, XM_125813, Z23056 |
| KDR (VEGFR2, Flk1) | 5, 6 | Homo Sapiens | AF063658 | NM_002019 |
| Tie-2 (TEK) | 7, 8 | Homo Sapiens | L06139 | NM_000459, U53603 |
| HPTPbeta intracellular domain | 9 | Homo Sapiens | | |
| VEGFR2 Intracellular region containing kinase domain | 10, 11 | Homo sapiens | AF063658 | |
| Tie-2 Intracellular region containing kinase domain | 12, 13 | Homo sapiens | L06139 | |
| HPTPbeta variant | 14, 15 | Homo sapiens | | |
| HPTPbeta crystallized domain | 16 | Homo sapiens | | |
| HPTPbeta reverse primer | 17 | Homo sapiens | | |

DETAILED DESCRIPTION OF THE INVENTION

I. Definitions

Hereinafter, the use of the terms HPTPbeta, VEGFR2, and Tie-2 should be construed such that variants of these proteins are encompassed within the meaning of the term. For example, the term "HPTPbeta" should be construed as HPTPbeta and variants thereof. "Variants," as used herein, means variant sequences of those proteins, or nucleotide sequences encoding the same (all used herein interchangeably) that are substantially similar to those described for their wild type counterpart. A protein or nucleotide sequence may be altered in various ways to yield a variant encompassed by the present invention including substitutions, deletions, truncations, insertions, and modifications. Methods for such manipulathreonine residues; glycosylation of serine, threonine, or asparagine residues; and ubiquitination of lysine residues.

In yet another embodiment, peptide mimics of a nucleic acid of the invention are encompassed within the meaning of variant. As used herein, "mimic," means an amino acid or an amino acid analog that has the same or similar functional characteristics of an amino acid. Examples of organic molecules that can be suitable mimics are listed at Table I of U.S. Pat. No. 5,807,819. Generally, a peptide variant, or nucleic acid sequence encoding the same, of the present invention will have at least 70%, generally, 80%, preferably up to 90%, more preferably 95%, even more preferably 97%, still even more preferably, and most preferably 99% sequence identity to its respective native amino acid sequence. Fusion proteins, or N-terminal, C-terminal or internal extensions, deletions, or insertions into the peptide sequence shall not be construed as affecting homology.

"Sequence Identity" or "Homology" at the amino acid or nucleotide sequence level is determined by BLAST algorithms (Basic Local Alignment Search Tool) (Altschul et al., Nucleic Acids Res. 25, 3389-3402 (1997) which are tailored for sequence similarity searching. The default scoring matrix used by various BLAST algorithms is the BLOSUM62 matrix, Henikoff et al. Proc. Natl. Acad. Sci. USA 89, 10915-10919 (1992), recommended for query sequences over 85 nucleotides or amino acids in length.

"Isolated," as used herein, refers to nucleic acid or amino acid sequences that are removed from their natural environment and are isolated or separated, and are at least about 60% free, preferably about 75% free, and most preferably about 90% free from other components with which they are naturally associated.

The term "angiogenesis mediated disorder" is defined as a disorder that involves a modulation in angiogenic activity resulting in the biological manifestation of a disease, disorder, and/or condition; in the biological cascade leading to the disorder; or as a symptom of the disorder. The Applicants have shown that the process of angiogenesis is modulated by HPTPbeta. This "involvement" of HPTPbeta in an angiogenesis mediated disorder includes, but is not limited to, the following: (1) The modulation of HPTPbeta activity as a "cause" of the angiogenesis mediated disorder or biological manifestation, whether the HPTPbeta is modulated genetically, by infection, by autoimmunity, trauma, biomechanical causes, lifestyle, or by some other causes; (2) The modulated IPTPbeta activity is part of the observable manifestation of the disease or disorder. That is, the disease or disorder is measurable in terms of the modulated HPTPbeta activity. From a clinical standpoint, modulated HPTPbeta activity indicates the disease, however, HPTPbeta activity need not be the "hallmark" of the disease or disorder; (3) The modulated HPTPbeta activity is part of the biochemical or cellular cascade that results in the disease or disorder. In this respect, inhibiting or stimulating of HPTPbeta (per the respective therapeutic goal) interrupts the cascade, and thus controls the disease; (4) The angiogenesis mediated disease or disorder is not the direct result of modulation in HPTPbeta activity per se, but modulation of the HPTPbeta activity would result in amelioration of the disease. "Modulation in HPTPbeta activity," as used herein, encompasses both unwanted or elevated HPTPbeta activity and desired or reduced HPTPbeta activity. As used herein, "angiogenesis mediated disorders" include: (1) those disorders, diseases and/or unwanted conditions which are characterized by unwanted or elevated angiogenesis, or (2) those disorders, diseases and/or unwanted conditions which are characterized by wanted or reduced angiogenesis."

"Protein," is used herein interchangeably with peptide and polypeptide.

II. Methods of Identifying an Agent Useful for Modulating Angiogenesis

The present invention is based, in part, on the discovery that modulation of HPTPbeta activity will modulate the activity of VEGFR2 and Tie-2. Applicants' studies demonstrate that a truncated version of recombinant HPTPbeta phosphatase domain dephosphorylates both Tie-2 and VEGFR2. Applicants' studies also demonstrate that full-length HPTPbeta attenuates the ligand-mediated activation of both Tie-2 by Ang1, and of VEGFR2 by VEGF. Further studies demonstrate the transfection of human endothelial cells with HPTPbeta antisense oligonucleotides results in about a 60% reduction of HPTPbeta expression and an enhanced ligand-mediated activation of both Tie-2 and VEGFR2. Applicants' studies demonstrate that overexpression of HPTPbeta inhibits angiogenesis in a VEGF-dependent ex vivo model of blood vessel growth (rat aortic ring model). Conversely, Applicants show that "knocking down" endogenous HPTPbeta expression using antisense oligos in endothelial cells enhances VEGF-mediated capillary morphogenesis. In view of the foregoing, Applicants demonstrate that HPTPbeta is a useful target in identifying agents for the treatment of angiogenesis mediated disorders.

Without limitation, the assays of the present invention are useful for high throughput screening or cell based assay formats.

1. Nucleic Acids of The Invention

The present invention further provides recombinant DNA (rDNA) molecules that contain a coding sequence of or a variant form of the molecules of invention. Methods for generating recombinant DNA molecules are well known in the art; for example, see Ausubel et al. (1996) Current Protocols in Molecular Biology John Wiley & Sons; Sambrook et al. (1989) Molecular Cloning—A Laboratory Manual, Cold Spring Harbor Laboratory Press. In the preferred rDNA molecules, a coding DNA sequence is operably linked to expression control sequences and/or vector sequences.

Various commercially available vectors may be employed to clone the genes of the invention that may serve different purposes. Vectors of the present invention may be capable of directing the replication either in a prokaryotic or eukaryotic host, insertion into the host chromosome, or expression of the gene. Control elements include, but are not limited to, inducible promoters, constitutive promoters, secretion signals, enhancers, and other regulatory elements. Preferably, the inducible promoter is readily controlled, such as being responsive to a nutrient or antibiotic in the medium.

2. Host Cells Expressing Nucleic Acids

Cells that naturally express nucleic acids and proteins of the invention may be known in the art. Cell lines that comprise enhanced levels of nucleic acids and proteins of the invention may be either purchased commercially or constructed. The present invention further provides host cells transformed with a nucleic acid molecule that encode sequences listed in Table 1 or their variants. The host cell can be either a prokaryotic or a eukaryotic cell. Preferred eukaryotic host cells include yeast, insect, Chinese hamster ovary (CHO), Swiss or NIH 3T3, baby hamster kidney (BHK), and the like.

Transformation of appropriate cell hosts with a recombinant DNA molecule of the present invention is accomplished by well-known methods that typically depend on the type of vector used and host system employed. With regard to transformation of prokaryotic host cells, heat shock methods, electroporation and salt treatment methods can be employed. With regard to transfection of vertebrate cells electroporation, cationic lipids, calcium phosphate precipitation, gene gun, microinjection, or protoplast fusion methods can be employed (See Ausubel et al. (1996) supra).

Successfully transformed cells, i.e., cells that contain an rDNA molecule of the present invention, can be identified by well known techniques including the selection for a selectable marker. For example, cells resulting from the introduction of an rDNA of the present invention can be cloned to produce single colonies. Cells from those colonies can be harvested, lysed and their DNA content examined for the presence or expression of the rDNA using Southern, Northern, or Western blots, or the proteins produced from the cell may be assayed via an immunological method.

3. Proteins of the Invention

A protein of the invention may be obtained by methods well known in the art, for example, using standard direct peptide synthesizing techniques (e.g., as summarized in Bodanszky, Principles of Peptide Synthesis, Springer-Verlag, Heidelberg: (1984)), such as via solid-phase synthesis (see, e.g., Merrifield, J. Am. Chem. Soc., 85, 2149-54 (1963); Barany et al., Int. J. Peptide Protein Res., 30, 705-739 (1987); and U.S. Pat. No. 5,424,398). If the gene sequence is known or can be deduced from the polypeptide sequence then the protein may be produced by standard recombinant methods. The proteins may be isolated or purified in a variety of ways known to those skilled in the art. Standard purification methods include precipitation with salts, electrophoretic, and chromatographic techniques, including ion exchange, hydrophobic, affinity, and reverse-phase HPLC chromatography, chromatofocussing, and others (see, e.g., Scopes, Protein Purification: Principles and Practice (1982); U.S. Pat. No. 4,673,641; Ausubel et al. supra; and Sambrook et al, supra). Ultrafiltration and diafiltration techniques, in conjunction with protein concentration, are also useful.

Antibody probes to the proteins of the invention can be prepared by immunizing suitable mammalian hosts utilizing appropriate immunization protocols using the proteins of the invention or antigenic fragments thereof. While the polyclonal antisera produced in this way may be satisfactory for some applications, for pharmaceutical compositions, use of monoclonal preparations is preferred. Immortalized cell lines which secrete the desired monoclonal antibodies may be prepared using standard methods, (see e.g., Kohler & Milstein, Biotechnology, 24, 524-526 (1992) or modifications which effect immortalization of lymphocytes or spleen cells, as is generally known.

Fragments of the monoclonal antibodies or the polyclonal antisera that contain the immunologically significant portion can be used as agonist or antagonists, as well as the intact antibodies. Use of immunologically reactive fragments, such as Fab or Fab' fragments, is often preferable, especially in a therapeutic context, as these fragments are generally less immunogenic than the whole immunoglobulin.

The antibodies or fragments may also be produced, using current technology, by recombinant means. Antibody regions that bind specifically to the desired regions of the protein can also be produced in the context of chimeras with multiple species origin, for instance, humanized antibodies. The antibody can therefore be a humanized antibody or human antibody, as described in U.S. Pat. No. 5,585,089 or Riechmann et al., Nature 332, 323-327 (1988).

4. Selection of Test Agents

Agents that can be screened in accordance with the assays of the invention include but are not limited to, libraries of known agents, including natural products, such as plant or animal extracts, synthetic chemicals, biologically active materials including proteins, peptides including but not limited to members of random peptide libraries and combinatorial chemistry derived molecular library made of D- or L-configuration amino acids, phosphopeptides (including, but not limited to, members of random or partially degenerate, directed phosphopeptide libraries), antibodies (including, but not limited to, polyclonal, monoclonal, chimeric, human, anti-idiotypic or single chain antibodies, and Fab, F(ab')$_2$ and Fab expression library fragments, and epitope-binding fragments thereof), and organic and inorganic molecules.

In one embodiment an agent that may modulate expression of a gene of the invention is a polynucleotide. The polynucleotide may be an antisense, a small interference RNA (siRNA), a triplex agent, or a ribozyme. For example, an antisense may be directed to the structural gene region or to the promoter region of a gene of the invention.

In addition to the more traditional sources of test agents, computer modeling and searching technologies permit the rational selection of test agents by utilizing structural information from both the ligand binding sites of proteins of the present invention and their known ligands. Such rational selection of test agents can decrease the number of test agents that must be screened in order to identify a candidate therapeutic agent. Knowledge of the sequences of proteins of the present invention allows for the generation of models of their binding sites that can be used to screen for potential ligands. This may be accomplished using molecular modeling with either the known crystal- and NMR-based three-dimensional structures of the proteins of the present invention. General information regarding modeling can be found in Schoneberg, T. et. al., *Molecular and Cellular Endocrinology*, 151:181-193 (1999), Flower, D., *Biochimica et Biophysica Acta*, 1422: 207-234 (1999), and Sexton, P. M., *Current Opinion in Drug Discovery and Development*, 2(5):440-448 (1999).

Once the model is completed, it can be used in conjunction with one of several existing computer programs to narrow the number of agents to be screened by the screening methods of the present invention, like the DOCK program (UCSF Molecular Design Institute, 533 Parnassus Ave, U-64, Box 0446, San Francisco, Calif. 94143-0446). In several of its variants it can screen databases of commercial and/or proprietary agents for steric fit and rough electrostatic complementarity to the binding site. Another program that can be used is FLEXX (Tripos Inc., 1699 South Hanley Rd., St. Louis, Mo.).

5. In Vitro Screening Assays to Identify Candidate Agents

The finding that the genes of the present invention play a role in regulating angiogenesis enables various methods of screening one or more test agents to identify candidate agents that ultimately may be used for prophylactic or therapeutic treatment. The invention provides methods for screening test agents for their ability, inter alia, to bind to a protein of the present invention, activate a protein of the present invention, prolong or augment the agonist-induced activation of a protein of the present invention or of signal transduction pathways that regulate expression of a gene(s) of the present invention.

When selecting candidate agents, it is preferable that the candidate agents be selective for a protein(s) of the invention. "Selective" means that the agent has significantly greater activity toward a certain protein(s) compared with other proteins, not that it is completely inactive with regard to other receptors. A selective agent for a specific receptor may show 10-fold, preferably 100-fold, more preferably 1000-fold and most preferably greater than 1000-fold selectivity toward that protein of the present invention than other related or unrelated proteins. Therefore, the purpose here is to identify and select an agent that would show minimal cross-reactivity and therefore minimal side effects when administered to an animal, but it should be kept in mind that other homologous proteins may show limited cross-reactivity. For screening agents it is preferred that the initial in vitro screen be carried out using a protein of the invention with an amino acid sequence that is greater than 80% homologous to a sequence listed in the sequence listing. More preferably the test agents will be screened against a human, or mouse protein, with the most preferable being human. For screening agents in a non-human species it is preferable to use the protein from the species in which treatment is contemplated.

The methods of the present invention are amenable to high throughput applications; however, the use of as few as one test agent in the method is encompassed by the term "screening". Test agents which bind to a protein of the invention, activate a protein of the invention, prolong or augment the agonist-induced activation of a protein of the invention or its signal transduction pathway, or increase expression of a protein or a gene of the invention, as determined by a method of the present invention, are referred to herein as "candidate agents." Such candidate agents can be used to regulate angiogenesis mediated disorders. However, more typically, this first level of in vitro screen provides a means by which to select a narrower range of agents, i.e., the candidate agents, which merit further investigation at additional levels of screening. The skilled artisan will recognize that a utility of the present invention is to identify, from a group of one or more test agents, a subset of agents which merit further investigation. One of skill in the art will also recognize that the assays of the present invention are useful in ranking the probable usefulness of a particular candidate agent relative to other candidate agents. Using such information the skilled artisan may select a subset of the candidate agents, identified in the first level of screening, for further investigation. By the way of example only, agents which activate a protein of the invention at concentrations of less than 200 nM might be further tested in a different assay system that may involve use of organ culture or in vivo models of angiogenesis.

The assay systems described below may be formulated into kits comprising a protein of the invention or cells expressing a protein of the invention which can be packaged in a variety of containers, e.g., vials, tubes microtitre well plates, bottles and the like. Other reagents may be included in separate containers and provided with the kit, e.g., positive and negative control samples, buffers, etc.

In one embodiment, the invention provides a method for screening one or more test agents to identify candidate agents that bind to a protein of the invention. Methods to determine binding of an agent to a protein are well known in the art. Typically, the assays include the steps of incubating a source of a protein of the invention with a labeled agent, known to bind to the protein, in the presence or absence of a test agent and determining the amount of bound labeled agent. The source of a protein of the invention may either be cells expressing the protein or some form of isolated protein, as described herein. The labeled agent can be a known ligand or any ligand analog labeled such that it can be measured, preferably quantitatively (e.g., $^{125}$I-, europium-, fluorescein-, GFP-, or $^{35}$S-methionine labeled). Such methods of labeling are well known in the art. Test agents that bind to a protein of the invention cause a reduction in the amount of labeled ligand bound to the protein, thereby reducing the signal level compared to that from control samples (absence of test agent). Variations of this technique have been described in literature. See Keen, M., *Radioligand Binding Methods for Membrane Preparations and Intact cells* in *Receptor Signal Transduction Protocols*, R. A. J. Challis, (ed), Humana Press Inc., Totoway N.J. (1997).

In another embodiment, the invention provides methods for screening test agents to identify candidate agents that activate a protein of the invention. Typically, the assays are cell-based; however, cell-free assays are known which are able to differentiate agonist and antagonist binding. Cell-based assays include the steps of contacting cells which express a protein of the invention with a test agent or control and measuring activation of the protein by measuring the expression or activity of components of the affected signal transduction pathways. For example, after contact with the test agent, lysates of the cells can be prepared and assayed for induction of second messengers like free intracellular calcium concentration [$Ca^{2+}$], cAMP, or phosphorylation levels of a downstream signaling protein or of the protein itself if the protein is a kinase or phosphatase, or activity of the downstream signaling molecules.

For example, intracellular free calcium concentrations are measured using techniques well known in the art. Cells are loaded with a suitable fluorescent dye, like Fura-2 or FLUO-4 (Molecular Probes), and changes in [$Ca^{2+}$] in response to different stimuli are detected using either a fluorescent microscope or a fluorescent plate reader. Ionophores like, Ionomycin may be used to measure the total [$Ca^{2+}$] in a cell.

Similarly, cAMP induction is measured with the use of DNA constructs containing the cAMP responsive element linked to any of a variety of reporter genes can be introduced into cells expressing a protein of the invention. Such reporter genes include, but are not limited to, chloramphenicol acetyltransferase (CAT), luciferase, glucuronide synthetase, growth hormone, fluorescent proteins, or alkaline phosphatase. Following exposure of the cells to the test agent, the level of reporter gene expression can be quantified to determine the test agent's ability to increase cAMP levels and thus determine a test agent's ability to activate a protein of the invention.

The activity of a phosphatase can be measured by methods well known in the art (Wang Y, Journal of Biological Chemistry, 267, 16696, 1992; Harder Kwet al., Biochemistry Journal, 298, 395, 1994; Itoh et al., Journal of Biological Chemistry, 267, 12356, 1992). In one format, the phosphatase activity is measured using a fluorescent assay that generates a fluorescent signal when the substrate is acted upon by the enzyme. Other small molecule phosphatase substrates such as PNPP (para nitro phenyl phosphate) could also be used. These assay formats may be scaled-up for utilization in a high throughput screening assays using FRET (fluorescence resonance energy transfer) FP (Fluorescence polarization) or Malachite green assay. Another means of assaying for phosphatase activity is to measure the loss of phosphorylation of its known substrates or receptor tyrosine kinase domain fusion proteins or synthetic peptides carrying phosphotyrosine residues. A phosphotyrosine western blot may be used to determine the decrease in phosphotyrosine content of a target protein in a suitable assay format (Huang et al., J Biol Chem 274, 38183-38188, 1999).

In another embodiment, specific phospho-tyrosine or phospho-serine antibodies may be utilized to measure the level of phosphorylation of a signaling protein after the exposure to a test agent, whereby the significant deviation in phosphorylation levels compared to control samples would indicate activation of a protein of the invention. The activity of a substrate may be measured by methods well known in the art. In one embodiment, the substrate activity is measured by assaying with anti-phosphotyrosine Western blotting following immunoprecipitation of the substrate, or ELISA like KIRA (Kinase-Inhibitor Receptor Assay). If a biological assay is known for the substrate it may also be employed, like an angiogenesis assay.

In some instances, a protein's (for example receptor) responses subside, or become desensitized, after prolonged exposure to an agonist. Another embodiment of the invention provides methods for identifying agents that prolong or augment the agonist-induced activation of a protein of the invention, or the activation of signal transduction pathway, in response to an agonist of a protein of the invention. Such agents may be used, for example, in conjunction with an agonist. Typically the method uses a cell based assay comprising: i) contacting a test agent with a first cell population which expresses a functional protein of the invention; ii) treating a second cell population with an agonist for the protein of the invention for a sufficient time and at a sufficient concentration to cause desensitization of the protein; iii) further treating the second cell population with the test agent; iv) determining the level of activation of the protein in the first and second cell population; and v) identifying those test agents that prolong or augment the activation of the protein of the invention or its signal transduction pathway as candidate agents. One of skill in the art will recognize that several mechanisms contribute to protein desensitization including, but not limited to, protein phosphorylation, protein internalization or degradation and signal transduction pathway downmodulation. One of skill in the art can determine the appropriate time (i.e., before, during or after agonist treatment) for contacting the cells with the test agents depending upon which mechanism of desensitization is targeted. For example, contacting the cells with test agents following agonist treatment, can detect test agents which block protein desensitization which occurs as a result of phosphorylation of the protein.

In another embodiment, the invention provides a method of screening one or more test agent to identify candidate agents that regulate transcription of the gene or regulate expression of the protein of the invention. Candidate agents that regulate transcriptional activity of genes of the invention may be identified using a reporter gene operably associated with the regulatory region of the gene of the invention (reporter gene construct). Such methods are known in the art. In one such method, the reporter gene construct is contacted with a test agent in the presence of a source of cellular factors and the level of reporter gene expression is determined. A test agent that causes an increase in the level of expression, compared to a control sample, is indicative of a candidate agent that increases transcription of the gene. To provide the cellular factors required for in vitro or in vivo transcription, appropriate cells or cell extracts are prepared from any cell type that normally expresses the gene.

Candidate agents that regulate expression of a gene of the invention can also be identified by a method wherein a cell is contacted with a test agent and the expression of the gene is determined. The level of expression of the gene in the presence of the test agent is compared with the level of expression in the absence of the test agent. Test agents that increase the expression are identified as candidate agents. Such a method detects candidate agents which increase the transcription or translation of the gene or which increase the stability of the mRNA or protein.

Additional assay formats may be used to monitor the ability of an agent to modulate the expression of a gene. For instance, mRNA expression may be monitored directly by hybridization. Other means to evaluate expression levels is to use either quantitative or semi-quantitative PCR or RNAse Protection Assay (Ma et al., Methods 10, 273-238 (1996). An example of quantitative PCR is the use of TaqMan™ analysis developed and described by Applied Biosystems, (ABI).

6. Screening Assays using In Vitro and In Vivo Models of Angiogenesis

Candidate agents selected on the basis of modulating phosphatase activity directly against a phosphatase or indirectly in cell based assays described above may then be further screened in angiogenesis assays that are well known in the art. Such assays include in vitro assays that measure surrogates of blood vessel growth in cultured cells or formation of vascular structures from tissue explants and in vivo assays that measure blood vessel growth directly or indirectly (Auerbach, R., et al. (2003). Clin Chem 49, 3240, Vailhe, B., et al. (2001). Lab Invest 81, 439-452).

a. In Vitro Models of Angiogenesis

Most of these assays employ cultured endothelial cells or tissue explants and measure the effect of candidate agents on "angiogenic" cell responses or on the formation of blood capillary-like structures. Examples of in vitro angiogenesis assays include but are not limited to endothelial cell migration and proliferation, capillary tube formation, endothelial sprouting, the aortic ring explant assay and the chick aortic arch assay.

b. In Vivo Models of Angiogenesis

In these assays candidate agents are administered locally or systemically in the presence or absence of growth factors (i.e. VEGF or angiopoietin 1) and new blood vessel growth is measured by direct observation or by measuring a surrogate marker such as hemoglobin content or a fluorescent indicator. Examples of angiogenesis include but are not limited to chick chorioallantoic membrane assay, the corneal angiogenesis assay, and the matrigel plug assay.

III. Treatment of Angiogenesis Mediated Disorders

1. Treatment of Disorders Mediated by Elevated Angiogenesis

As previously described, an angiogenesis mediated disorder encompasses disorders resulting from either elevated or reduced angiogenesis. The agents screened by the present invention may be used in a method for the treatment of a disorder mediated by elevated angiogenesis. Such agents identified by the present invention may be used to treat diseases like diabetic retinopathy, macular degeneration, sickle cell anemia, sarcoid, syphilis, pseudoxanthoma elasticum, Paget's disease, vein or artery occlusion, carotid obstructive disease, chronic uveitis/vitritis, mycobacterial infections, Lyme's disease, systemic lupus erythematosis, retinopathy of prematurity, Eales' disease, Behcet's disease, infections causing retinitis or choroiditis, presumed ocular histoplasmosis, Best's disease, myopia, optic pits, Stargardt's disease, pars planitis, chronic retinal detachment, hyperviscosity syndromes, toxoplasmosis, trauma, post-laser complications, diseases associated with rubeosis (neovasculariation of the angle) and diseases caused by the abnormal proliferation of fibrovascular or fibrous tissue including all forms of proliferative vitreoretinopathy. Agents screened by of the present invention can also treat diseases associated with chronic inflammation such as Crohn's disease and ulcerative colitis, psoriasis, sarcoidosis and rheumatoid arthritis. Other diseases that can be treated according to the present invention are hemangiomas, Osler-Weber-Rendu disease, or hereditary hemorrhagic telangiectasia, solid or blood borne tumors and acquired immune deficiency syndrome.

2. Treatment of Disorders Mediated by Reduced or Limited Angiogenesis

In one aspect, an agent may be used in a method for the treatment of a disorder mediated by reduced angiogenesis. A disorder mediated by reduced angiogenesis is one characterized by a tissue that is suffering from or is at risk of suffering from ischemic damage, infection, and/or poor healing, which results when the tissue is deprived of an adequate supply of oxygenated blood due to inadequate circulation (ischemic tissue). Non-limiting examples of angiogenesis reduced disorders that may be treated by the present invention are herein described below.

a. Method of Vascularizing Ischemic Tissue

In one aspect, an agent that modulates HPTPbeta activity may be used in a method of vascularizing ischemic tissue. Examples of ischemic tissue include, but are not limited to, tissue that lack adequate blood supply resulting from myocardial and cerebral infarctions, mesenteric or limb ischemia, or the result of a vascular occlusion or stenosis. In one example, the interruption of the supply of oxygenated blood may be caused by a vascular occlusion. Such vascular occlusion can be caused by arteriosclerosis, trauma, surgical procedures, disease, and/or other indications. There are many ways to determine if a tissue is at risk of suffering ischemic damage from undesirable vascular occlusion. For example, in myocardial disease these methods include a variety of imaging techniques (e.g., radiotracer methodologies, x-ray, and MRI) and physiological tests. Therefore, induction of angiogenesis in tissue affected by or at risk of being affected by a vascular occlusion is an effective means of preventing and/or attenuating ischemia in such tissue. Thus, the treatment of skeletal muscle and myocardial ischemia, stroke, coronary artery disease, peripheral vascular disease are fully contemplated.

b. Method of Repairing Tissue by Enhancing Limited Angiogenesis

In another aspect, an agent that modulates HPTPbeta activity may be used in a method of repairing tissue. As used herein, "repairing tissue," means promoting tissue repair, regeneration, growth, and/or maintenance including, but not limited to, wound repair or tissue engineering. One skilled in the art readily appreciates that new blood vessel formation is required for tissue repair. Tissue may be damaged by traumatic injuries or conditions including arthritis, osteoporosis, and other skeletal disorders, from injuries due to surgical procedures, irradiation, laceration, toxic chemicals, viral infection, bacterial infection, non-healing wounds, or burns.

Agents that modulate HPTPbeta activity may also be used in a method to aid in tissue repair in the context of guided tissue regeneration (GTR) procedures, like tissue engineering. Thus, the present method can be used to augment the design and growth of human tissues outside the body for later implantation in the repair or replacement of diseased tissues. For example, an agent that modulates HPTPbeta activity may be useful in promoting the growth of skin graft replacements that are used as a therapy in the treatment of burns.

In another aspect of tissue engineering, an agent that modulates HPTPbeta activity may be included in cell-containing or cell-free devices that induce the regeneration of functional human tissues when implanted at a site that requires regeneration. As previously discussed, biomaterial-guided tissue regeneration can be used to promote bone regrowth in, for example, periodontal disease. Thus, an agent that modulates HPTPbeta activity may be used to promote the growth of reconstituted tissues assembled into three-dimensional configurations at the site of a wound or other tissue in need of such repair.

In another aspect of tissue engineering, an agent that modulates HPTPbeta activity can be included in external or internal devices containing human tissues designed to replace the function of diseased internal tissues. This approach involves isolating cells from the body, placing them on or within structural matrices, and implanting the new system inside the body or using the system outside the body. The method of the invention can be included in such matrices to promote the growth of tissues contained in the matrices. For example, an agent that modulates HPTPbeta activity can be included in a cell-lined vascular graft to promote the growth of the cells contained in the graft. It is envisioned that the method of the invention can be used to augment tissue repair, regeneration, and engineering in products such as cartilage and bone, central nervous system tissues, muscle, liver, gastrointestinal tract (includes IBD and ulcer diseases) and pancreatic islet (insulin-producing) cells.

IV. Diagnostic or Prognostic Methods

Expression of HPTPbeta or nucleic acids encoding the same may be used as a diagnostic marker for the prediction or identification of an angiogenesis mediated disorder. For example, a cell or tissue sample may be assayed for the expression levels of HPTPbeta by any of the methods described herein and compared to the expression level found in normal healthy tissue. Such methods may be used to diagnose or identify angiogenesis mediated disorders.

Expression of HPTPbeta or nucleic acids encoding the same may also be used as a marker for the monitoring of the progression of an angiogenesis mediated disorder. Expression or activity of HPTPbeta or nucleotides encoding the same may also used to track or predict the progress or efficacy of a treatment regime in a patient. For instance, a patient's progress or response to a given drug may be monitored by measuring gene expression of HPTPbeta of the invention in a cell or tissue sample after treatment or administration of the drug. The expression of HPTPbeta in the post-treatment sample may then be compared to gene expression from the same patient before treatment.

EXAMPLES

Example 1

Isolation of a Full Length HPTPbeta cDNA Clone

Methods: A full length clone of HPTPbeta is obtained by tiered screening of a human placenta arrayed cDNA library from Origene using the forward vector primer supplied and a reverse primer specific for HPTPbeta (SEQ ID NO:17) (5'-GTTAGGGAAGTAAATCGATACTGGG-3'). Polymerase chain reactions (PCR) are accomplished using Advantage Polymerase (Clontech) using the following temperature cycles: 1 cycle at 95° C. for 3 min, 30 cycles at 94° C. for 1 min and 62° C. for 2 min followed by 1 cycle at 62° C. for 3 min. According to the manufacturers instructions, bacterial sub-plates of positive cDNA pools are screened using the same primers and the subsequent positive bacterial colony containing a full length HPTPbeta cDNA (SEQ ID NO: 14) clone was isolated. Plasmid DNA are then isolated and sequenced.

Results: The isolated clone encoded a full length HPTPbeta protein (SEQ ID NO: 15), and has a stop codon at 3 prime end of the coding region. Sequence alignments showed that it was essentially identical to a previously published HPTPbeta clone (Genbank accession # X54131) except for the absence of 270 nucleotides corresponding to exon 6 suggesting that the clone encoded a novel splice variant. Confirming this impression, further review of the 5' end of the HPTPbeta gene revealed that the missing exon codes for FNIII (fibronectin like domain 3) repeat 5 (one of a total of 16 possible) (FIG. 1).

Example 2

Recombinant HPTPbeta dephosphorylates Recombinant VEGFR2 and Tie-2 Kinases In Vitro Methods: Expression and purification of recombinant HPTPbeta catalytic domain [SEQ ID NO: 16] is accomplished by subcloning the intracellular domain of HPTPbeta (cDNA clone starting at the codon for amino acid 1662 through the stop codon) into the pGEX4T1 vector (Pharmacia) and expressed as a GST-fusion protein in *E. coli* BL21-RIL cells (Stratagene). Induced cells are thawed on ice and resuspended in 20 mM Tris-HCl, pH=8.0, 1% Trition x-100, 2 mM DTT and EDTA-free protease inhibitor cocktail. 10 mg/ml lysozyme is added and cells are lysed by sonication. The cell debris is pelleted using the Beckman J2-MI at 17,000 rpm. The supernatant is added to prepared glutathione sepharose 4B resin batch method. After binding, the column is poured and packed with the resin/protein mixture and then washed. The column is unpacked for cleavage of GST using thrombin (50 units thrombin/1 mL resin). Mixture is rotated O/N at room temperature. The column is re-packed for washing cleaved material from resin. Cleaved material is collected and then loaded onto Q sepharose FF column. The column is washed and protein eluted with 0-1M NaCl gradient. A coomassie blue stained SDS-PAGE gel identified fractions containing recombinant material and pooled fractions and dialyzed against 20 mM Tris-HCl, pH 8.0, 10 mM BME, 2 mM DTT.

Measurements of recombinant phosphatase activity are performed using the substrate DiFMUP (6,8-difluoro-4-methylumbelliferyl phosphate) from Molecular Probes. 10 μM DiFMUP is incubated with increasing amounts of recombinant HPTPbeta in buffer containing 10 mM Sodium Acetate (pH 6), 150 mM NaCl, 0.1% BSA, 5 mM DTT. Measurements of increased substrate fluorescence, indicative of phosphatase activity, are observed at an excitation wavelength of 355 nm and an emission wavelength of 460 nm using a Victor V plate reader (Wallac).

To prepare recombinant GST fusion receptor tyrosine kinase domains for kinase domain dephosphorylation assays, intracellular kinase domain cDNAs of the VEGFR2 [SEQ ID NO: 11] and Tie-2 [SEQ ID NO: 13] receptors are generated by PCR starting at the codon for the $1^{st}$ amino acid inside the transmembrane domain, a lysine in both receptors, using forward primers having an "in-frame" Sal I site and reverse primer containing a Not I site for both receptors. The pLNCX2 plasmids below are used as templates. PCR fragments are subcloned into the GST fusion vector pACGHLT-A (Pharmingen/BD Biosciences) and sequenced through on both strands. Confirmed clones are transfected into sf9 insect cells using the BACULOGOLD™ system from Pharmingen. Resulting baculovirus stocks are amplified and final protein production is rendered in infected sf9 cells on 150 mm dishes. Infected sf9 cells were lysed in 2 mL of Triton Lysis Buffer (TLB, 20 mM Tris-HCl, pH 8.0, 137 mM NaCl, 10% glycerol, 1% Triton X-100, 2 mM EDTA, 1 mM Sodium Orthovanadate, 1 mM Sodium Fluoride, 1 mM PMSF, 1 ug/ml leupeptin, 1 ug/ml pepstatin), scraped, and frozen at −80° C. until used.

Purification of recombinant GST fusion kinase domains is accomplished using GST agarose beads (Pharmacia) prepared according the package insert. Briefly, 100 uL of the infected sf9 lysate is mixed with 50 uL of washed GST agarose beads in 1 mL TLB in batch form. After 4 hours, the beads are spun and washed twice in cold TLB. To ensure maximal phosphorylation of the recombinants, the beads are washed once and resuspended in 100 uL of kinase buffer (200 mM Tris-HCl, pH=8.0, 1M NaCl, 120 mM MgCl2, 10 mM DTT) including 1 mM ATP and incubated for 30 minutes at room temperature. The beads, bound with phosphorylated recombinant kinase domains, are washed twice in assay buffer (10 mM Tris HCl pH=7, 150 mM NaCl, 0.1% BSA, 5 mM DTT) and kinase domain dephosphorylation assays are performed by incubating the beads for 2 hours at 37° C. with increasing amounts of recombinant HPTPbeta. After incubation, beads are rinsed twice with TLB and eluted by boiling for 10' in 1×SDS sample buffer. Samples are loaded on a 10% SDS-PAGE and transferred to PVDF for anti-phosphotyrosine western blotting (see example 4).

Figure 2:
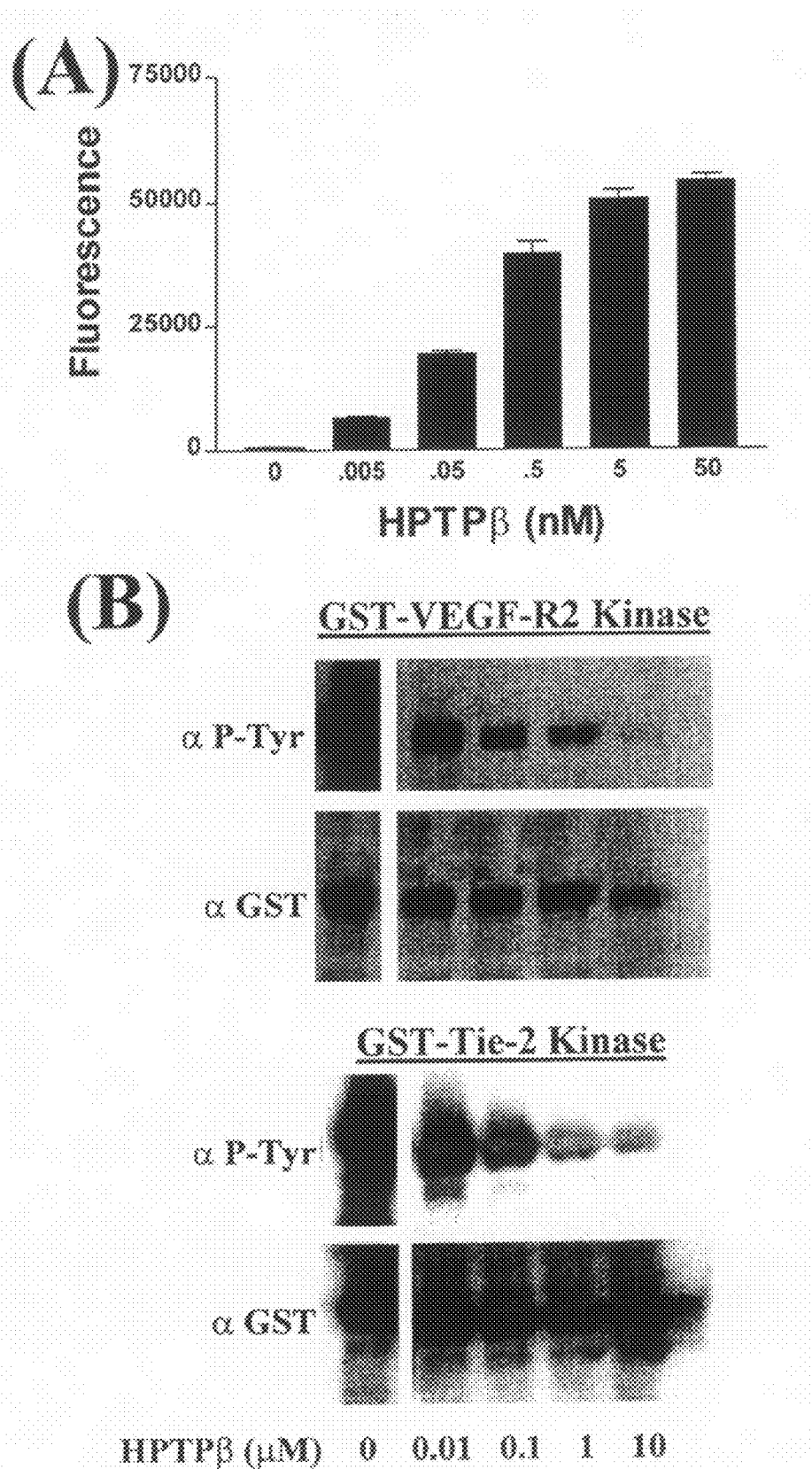
FIG. 2. Recombinant HPTPbeta dephosphorylates recombinant VEGFR2 and Tie-2 kinases in vitro. (A) Graph showing increased substrate fluorescence with increasing amounts of recombinant HPTPbeta intracellular domain using the DiFMUP substrate. (B) Anti-phosphotyrosine western blots of recombinant GST fusions of the tyrosine kinase domains of the VEGFR2 and Tie-2 receptors showing a dose dependant decrease in phosphorylation after incubation with increasing amounts of recombinant HPTPbeta.

Results: Increased substrate fluorescence indicative of phosphatase activity is seen with increasing amounts of recombinant HPTPbeta intracellular domain using the DiFMUP substrate (FIG. 2A). This recombinant HPTPbeta is able to dephosphorylate recombinant autophosphorylated kinase domains as seen by anti-phosphotyrosine western blotting which shows a dose dependant decrease in the phosphorylation of recombinant VEGFR2 and Tie-2 (FIG. 2B.). These results demonstrate a method that could be used to screen for agents that inhibit HPTPbeta activity.

Example 3

HPTPbeta Attenuates Ligand induced VEGFR2 and Tie-2 Receptor Phosphorylation in Cells Overexpressing HPTPbeta Methods: HEK293 cells are transfected with the cDNA construct isolated from the Origene library, already in the mammalian expression vector pCMV6-XL4, using LipofectAMINE-PLUS (Invitrogen).

For expression in human umbilical vein endothelial cells (HUVEC's) adenoviruses are prepared and purified containing no insert (empty), full length HPTPbeta and green fluorescent protein (GFP) by Galapagos Genomics NV as described in US Patents: U.S. Pat. No. 5,994,128 & U.S. Pat. No. 6,033,908.

In cell phosphatase assays are accomplished by infecting Human Umbilical Vein Endothelial Cells with HPTPbeta, GFP, or Empty adenovirus in 100 mm dishes for 24 hours. Infected cells were trypsinized and re-plated at 5,000 cells/well in a 96 well plate and allowed to attach for 2 hours in complete growth medium (EGM). Complete medium was replaced with Hanks Buffered Saline (HBSS, Gibco) and substrate fluorescence are measured 15 minutes after the addition of 100 uM DiFMUP substrate (Molecular Probes) using a Victor V plate reader as mentioned in Example 2.

For phosphatase activity in human embryonic kidney cells, HEK293H (Gibco) are grown in suspension in 293SFM media (Gibco) and transfected on 100 mm dishes using LIPOFECTAMINE™ 2000 (Invitrogen), a proprietary formulation for the transfection of nucleic acids (DNA and RNA) into eukaryotic cells. After 24 hours cells are resuspended transferred back to shaker flasks for an additional 24 hours. Phosphatase activity is measured using DiFMUP in 96 well plates as above with 100,000 cells/well. For inhibition of tyrosine phosphatases, the cells are pre-incubated with Bismaloalto-organovanadium (BMOV) for 15 minutes prior to the addition of DIFMUP. HPTPbeta protein expression is confirmed after each experiment in parallel plates by western blotting.

To establish stable cell lines expressing endothelial cell receptor tyrosine kinases, HEK293 cells are transfected with mammalian expression plasmids (pLNCX2, Clontech) containing either the full length human VEGF receptor type 2 (VEGFR2) [SEQ ID NO: 6] cDNA or full length human Tie-2 receptor [SEQ ID NO: 8] cDNA using LIPOFECTAMINE™ PLUS (Invitrogen), a reagent used in conjunction with transfection reagents to enhance transfection in adherent cell lines, on 100 mm dishes. Forty-eight hours post transfection the cells are selected in growth medium (DMEM, 10% fetal bovine serum) supplemented with 1.4 mg/mL GENETICIN™ (Gibco), an analog of neomycin sulfate which interferes with the function of 80S ribosomes and protein synthesis in eukaryotic cells (the concentration of GENETICIN™ was determined by kill curve analysis of wild type HEK293 cells). After selection, isolated colonies are chosen using cloning cyclinders and the clonal cell lines propagated in complete selection media. Clonal cell lines were screened for the presence of the receptors by western blot as well as by receptor activation assay. The Tie-2 stable cells are designated T2-3 and the VEGFR2 stable cells designated R2-6.

VEGFR2 and Tie-2 receptor phosphorylation is assayed by anti-phosphotyrosine western blotting following immunoprecipitation of the receptors from endothelial cells or receptor transfected 293 cells. Briefly, endothelial cells (HUVEC's) are plated on 100 mm dishes, stimulated with a dose range of either recombinant VEGF165 or recombinant Angiopoietin-1 (R&D Systems, resuspended in PBS containing 0.2% bovine serum albumin) for 5 or 7 minutes, respectively. After stimulation the cells were lysed in 1 mL of Triton Lysis Buffer (TLB, 20 mM Tris-HCl, pH 8.0, 137 mM NaCl, 10% glycerol, 1% Triton X-100, 2 mM EDTA, 1 mM Sodium Orthovanadate, 1 mM Sodium Fluoride, 1 mM PMSF, 1 ug/ml leupeptin, 1 ug/ml pepstatin) at 4 deg C. To immunoprecipitate VEGFR2, 1 ml of the lysate from cells stimulated with VEGF165 is incubated with 25 uL wheat germ agglutinin-agarose (Sigma, lectin from *triticum vulgaris*). Lysates stimulated with Ang-1 are immunoprecipitated using 2 ug of anti Tie-2 antibody (Ab33) and 25 uL of protein A/G Plus (Santa Cruz Biotechnology). Following overnight incubation, the complexes are centrifuged, washed once in TLB and eluted by boiling in 30 uL of 1× sample buffer (50 mM Tris-HCl pH=6.8, 10% glycerol, 2% SDS, 0.1 M DTT, 0.1% bromphenol blue). Twenty microliters of each sample is loaded onto a 6% SDS-PAGE gel, transferred to PVDF (Novex), blocked in 5% bovine serum albumin in TBS-0.1% Tween-20 (TTBS) and phosphotyrosine western blotting is performed using anti-phosphotyrosine antibody (PY99, Santa Cruz Biotechnology) diluted 1:1000 in 2.5% bovine serum albumin in TTBS. Signal is detected using HRP labeled secondary antibodies and ECL solution (Amersham). After exposure the blots are stipped and re-probed with anti-Tie-2 receptor (Ab33) or anti VEGFR2 (R2.2, Whitaker G B, *J Biol Chem* 2001 Jul. 6; 276(27):25520-31) at a 1:5000 dilution of each. Resulting films are scanned and quantitated using Quantity-One software (Bio-Rad) and results reported as the amount of phosphotyrosine signal over receptor signal (P-Tyr/Receptor).

In HEK293 stable cells receptor phosphorylation assays are performed in R2-6 and T2-3 cells that are plated, transfected and stimulated with ligand in 6 well dishes. Each well is lysed with 100 μL of TLB and 20 ug of the resulting protein is loaded onto a 6% SDS-PAGE gel, transferred to PVDF and serially western blotted with anti P-Tyr and anti-receptor antibodies as described above. No immunoprecipitation of the receptors was necessary.

Figure 3:
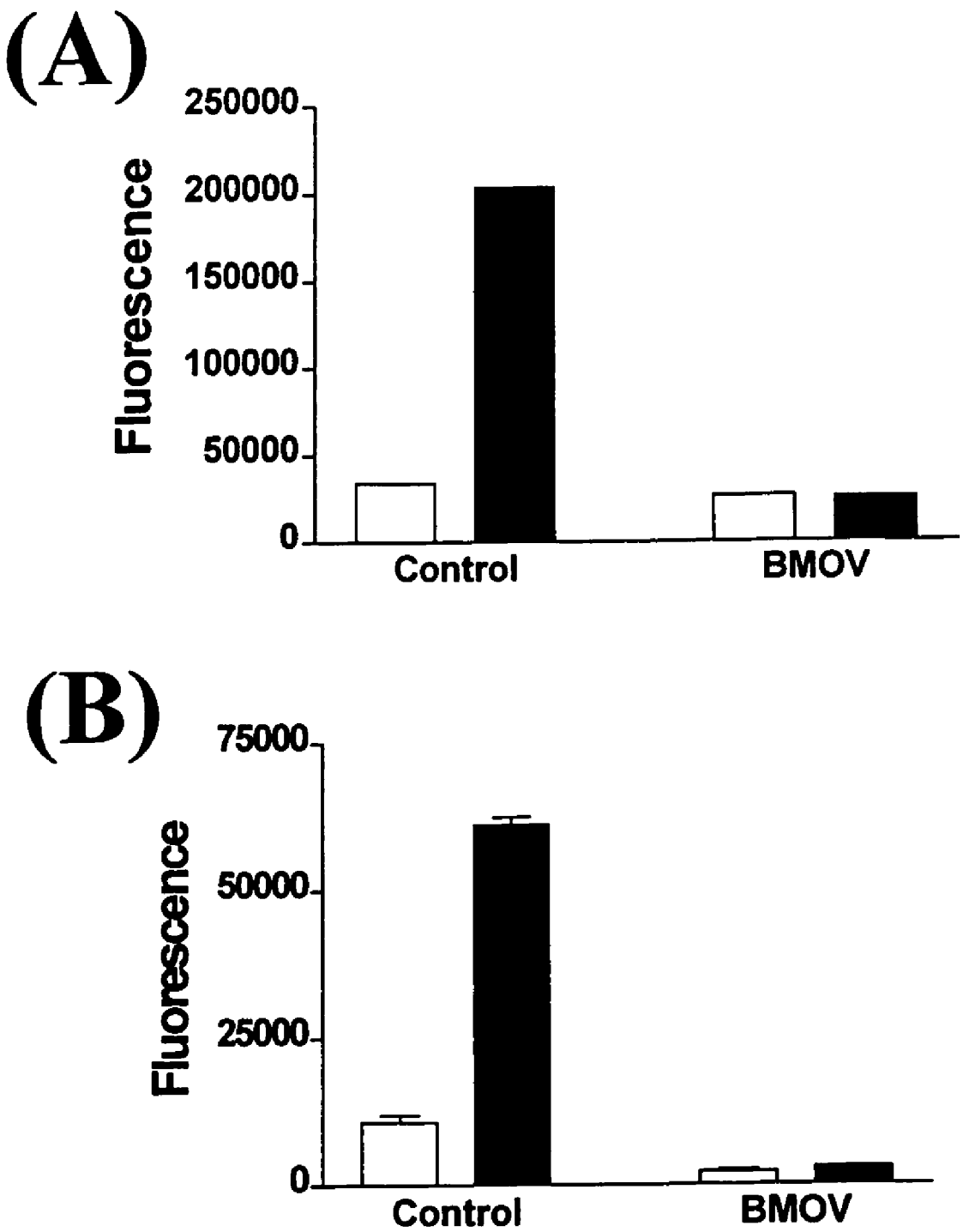
FIG. 3. Overexpression of HPTPbeta using either a plasmid or adenoviral vector increases phosphatase activity in HEK293H cells and HUVEC's, respectively. (A) pCMV6-XL4/HPTβ transfected (■) HEK293H cells have increased phosphatase activity over mock transfected (□) controls as measured with DiFMUP. (B) Increased phosphatase activity in HUVEC's infected with the HPTPbeta adenovirus (■) versus the green fluorescent protein (GFP) control adenovirus (□). The phosphatase activity in both cell types is inhibited with 500 µM of the nonselective tyrosine phosphatase inhibitor BMOV.

Results: pCMV6-XL4/HPTPbeta transfected HEK293H cells have increased phosphatase activity over mock-transfected controls as measured with DiFMUP (FIG. 3A). Increased phosphatase activity is also seen in HUVEC's infected with the HPTPbeta adenovirus versus the green fluorescent protein (GFP) control adenovirus (FIG. 3B). The activity in both cell types is inhibited with 500 uM of the generic tyrosine phosphatase inhibitor BMOV (bismatolatol oxovanadium) (FIG. 3).

Figure 4:
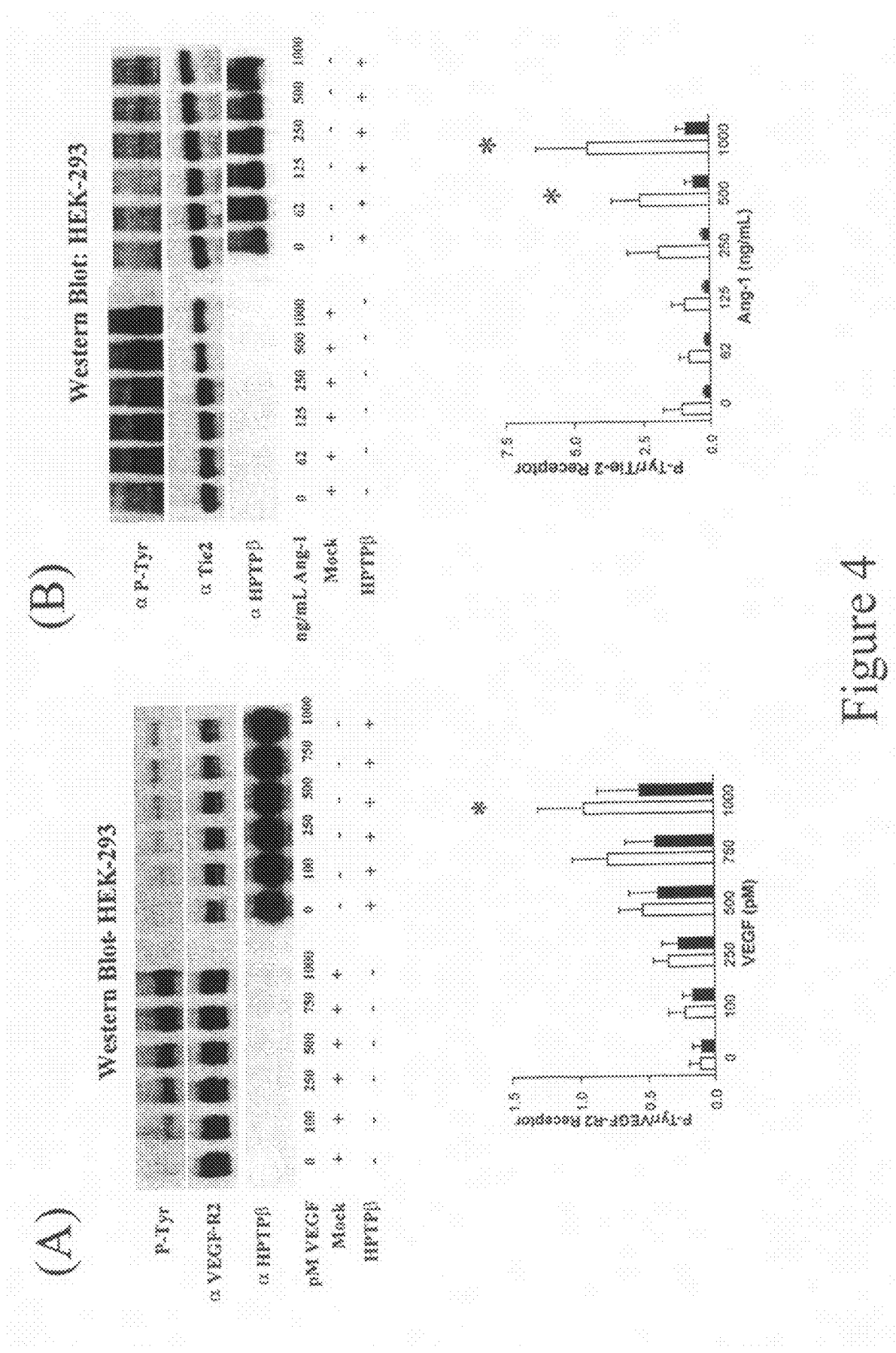
FIG. 4. Transient overexpression of HPTPbeta attenuates ligand-induced autophosphorylation of VEGFR2 and Tie2 stably expressed in HEK293 cells. Phosphotyrosine (P-Tyr), VEGFR2, Tie-2 and HPTPbeta western blots and graphs depicting a blunted ligand induced phosphorylation of the VEGFR2 receptor (A) and the Tie-2 receptor (B) in HEK293-receptor stable cells when transfected with the pCMV6-XL4/HPTPβ expression plasmid. (□=mock transfected, ■=HPTPbeta transfected, *=p<0.05)
Figure 5:
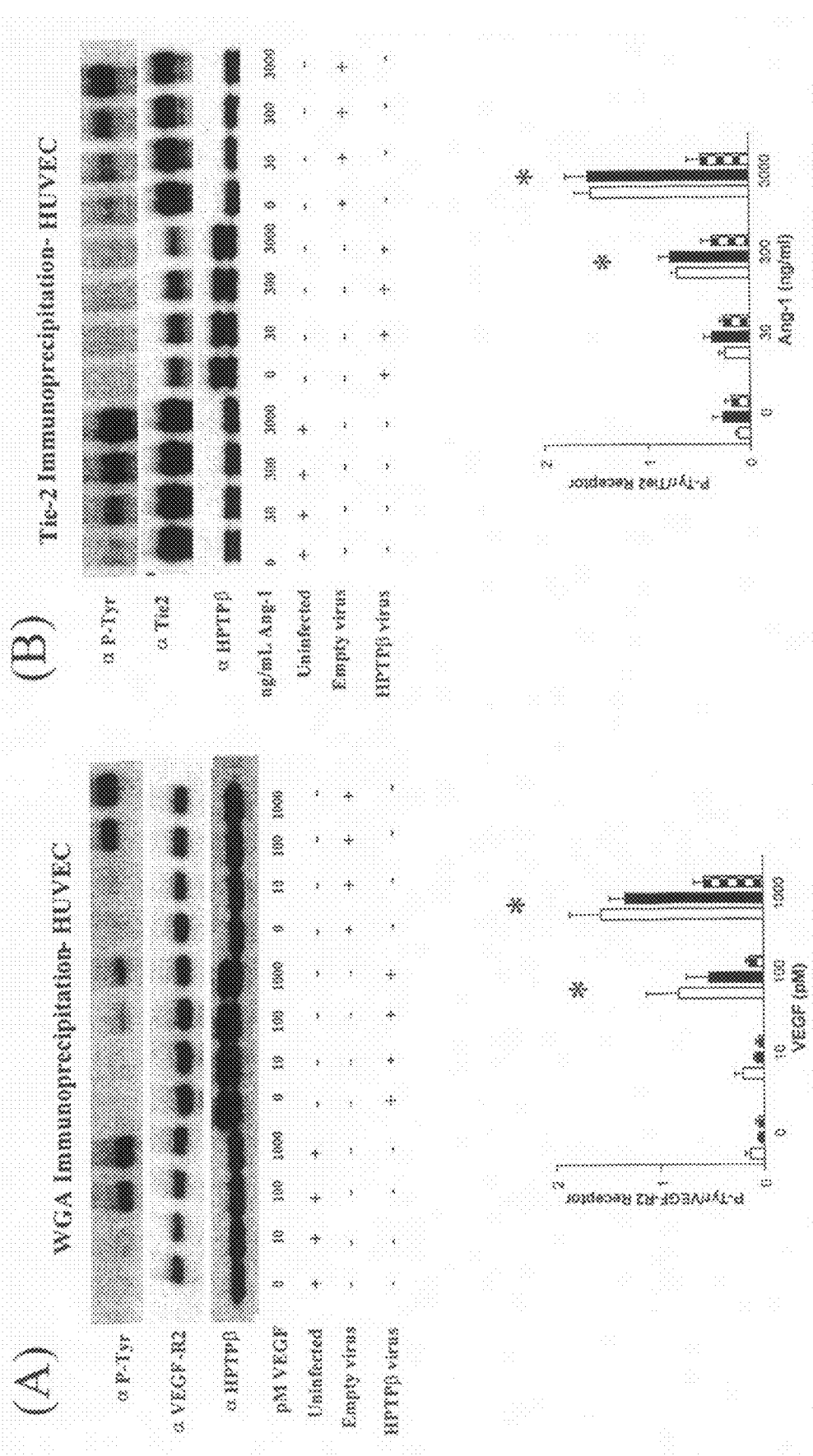
FIG. 5. Overexpression of HPTPbeta attenuates ligand-mediated autophosphorylation of endogenous VEGFR2 and Tie2 in human umbilical vein endothelial cells (HUVEC). (A) Anti-phosphotyrosine western blots of immunoprecipitated VEGFR2 from VEGF stimulated HUVEC's illustrating a decrease in the level of VEGFR2 phosphorylation when HPTPbeta is overexpressed and corresponding graph depicting cumulative VEGFR2 receptor activation data with and without HPTPbeta overexpression, n=3. (B) Anti-phosphotyrosine western blots of immunoprecipitated Tie-2 from Ang-1 stimulated HUVEC's showing a decrease in the level of Tie-2 receptor phosphorylation when HPTPbeta is overexpressed and a graph depicting cumulative data of Tie-2 receptor activation in empty and HPTPbeta adenovirus infected HUVEC's, n=3. (□=uninfected, ■=empty virus, ▣=HPTPbeta virus, *=p<0.05)

Transient overexpression of HPTPbeta using the pCMV6-XL4/HIPTPbeta expression plasmid decreased ligand-mediated phosphorylation of VEGFR2 and Tie-2 in HEK293-receptor stable cells as seen in the anti-phosphotyrosine western blots of immunoprecipitated receptors in from VEGFA or Ang1 stimulated cells (FIG. 4). Similarly, adenoviral overexpression of HPTPbeta in endothelial cells decreased the ligand-induced phosphorylation of the endogenous VEGFR2 and Tie-2 receptors as seen in the anti-phosphotyrosine western blots of immunoprecipitated receptors from VEGFA or Ang1 stimulated HUVEC's (FIG. 5). Taken together, these findings indicate that HPTPbeta can negatively regulate the activation of both Tie-2 and VEGFR2. These results also demonstrate a method for measuring the effects of modulating HPTPbeta activity on Tie-2 and VEGFR2 activation. Importantly, the activation of other RTKs could be negatively regulated by HPTPbeta and these effects could also be measured by this method.

Example 4

Active and Inactive Forms of HPTPbeta Modulate VEGF165 Induced Calcium Flux in Endothelial Cells Methods: Human endothelial cells (HUVEC) were seeded at 1×10⁶ cells per 100 mm dish in EGM one day prior to infection with adenovirus. Individual plates were infected with either active or inactive HPTPbeta adenoviruses in EGM for 24 hours at a multiplicity of infection of 50. Inactive HPTPbeta has the active site catalytic cysteine (Cys1904) mutated to a serine (HPTPbeta-C/S). Uninfected cells were left in EGM during the infection period. After incubation with the virus, infected and uninfected cells were re-plated in 96-well plates at 10,000 cells per well for an additional 24 hours before assaying for calcium flux in response to recombinant VEGF165 (R&D Systems). Plated cells were loaded with 4 μM of the calcium sensing dye FLUO-4 according to the manufacturers instructions (Molecular Probes). Intracellular calcium flux was measured using a FLIPR plate reader. All calcium responses to VEGF165 were normalized to the maximal signal stimulated by 10 μM of the calcium ionophore ionomycin (Sigma).

Figure 6:
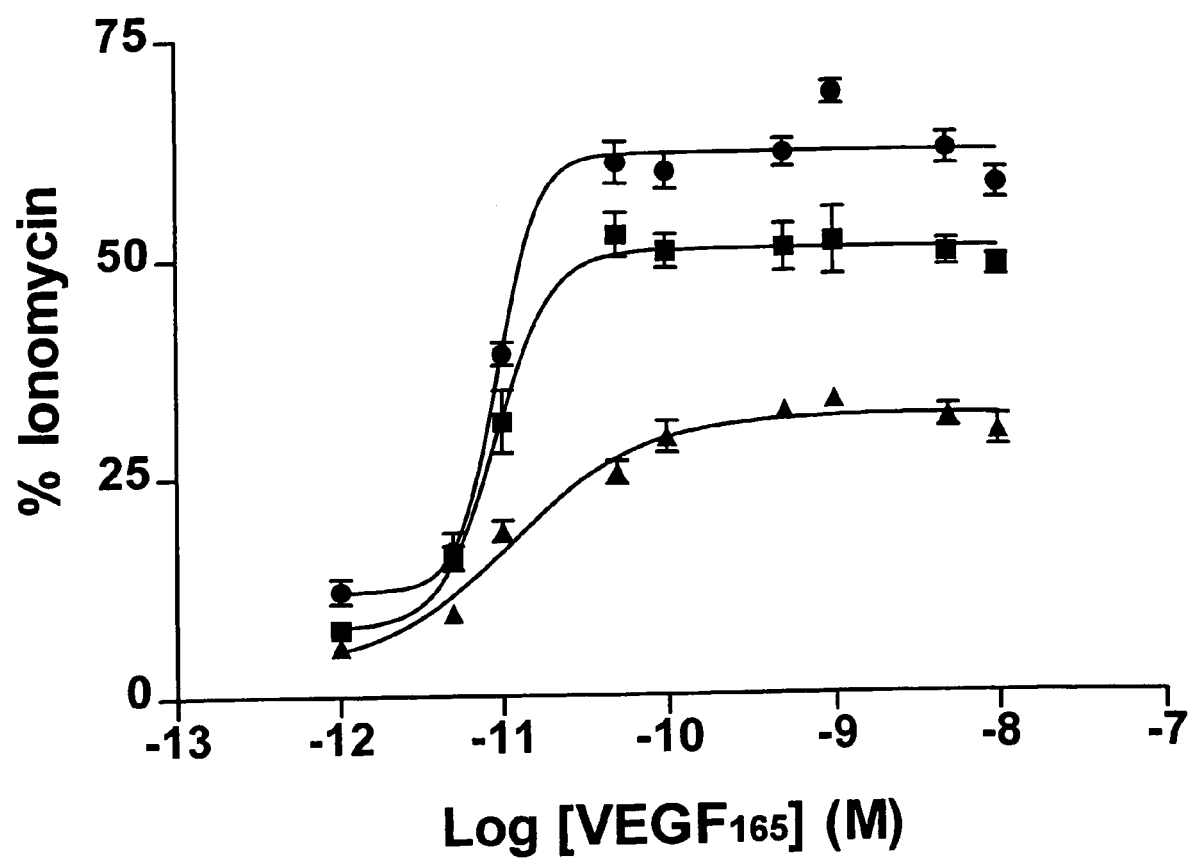
FIG. 6. Overexpression of HPTPbeta in HUVEC attenuates VEGF-mediated calcium mobilization. Endothelial cells infected with either wild type or inactive HPTPbeta adenoviruses were loaded with the calcium sensing dye Fluo-4 (Molecular Probes) and challenged with increasing concentrations of recombinant VEGF$_{165}$. Graph shows a decrease in the magnitude of the VEGF$_{165}$ stimulated calcium flux in wild type HPTPbeta infected cells (▲) compared to uninfected controls (■). Conversely, an increase in VEGF stimulated calcium flux was seen in the cells infected with a catalytically inactive form of HPTPbeta (●) (catalytic Cysteine mutated to a Serine). No change in the EC$_{50}$ values for VEGF$_{165}$ was observed within the treatment groups. Data represented as % of maximal calcium response to 10 µM ionomycin.

Results: The graph in FIG. 6 shows a decrease in the magnitude of the VEGF165 stimulated calcium flux in wild type HPTPbeta infected cells (▲) compared to uninfected controls (■). Conversely an increase in VEGF stimulated calcium flux was seen in the cells infected with a catalytically inactive form of HPTPbeta(●). No change in $EC_{50}$ for VEGF165 stimulated calcium flux was observed only changes in apparent maximal signal. These findings demonstrate that HPTPbeta can regulate signaling by VEGF receptors and that a downstream signaling assay such as calcium mobilization could be used to test the efficacy of HPTPbeta modulators in endothelial cells.

Example 5

Knockdown of HPTPbeta Protein with an Antisense Oligonucleotide Enhances Ligand-induced VEGFR2 and Tie-2 Receptor Phosphorylation Methods: Antisense (AS) oligonucleotides capable of selective inhibition of HPTPbeta expression are supplied by Sequitur, Inc. (Natick, Mass.). Design and screening of the HPTPbeta antisense oligonucleotides (AS) is accomplished as follows: ten phosphorothioate-containing DNA oligonucleotides with perfect 25 nucleotide complementarity to selected regions of the HPTPbeta coding sequence were synthesized by standard phosphoramidite chemistry and purified with trityl-on using reverse-phase columns followed by de-salting on a size exclusion matrix. Chemistry-matched control oligomers, lacking significant sequence homology to known or predicted human genes, are made in parallel. Antisense and control oligonucleotides are transfected into Human Microvascular Endothelial Cells with LIPOFECTAMINE™ 2000 using conditions recommended by the manufacturer (Invitrogen, Inc.). Uptake efficiency is monitored in live cells using a fluorescently labeled oligonucleotide as described by the manufacturer (Sequitur, Inc.). At 24 h post-transfection, cells are lysed and polyadenylated mRNA is isolated with an mRNA CATCHER™ plate (Sequitur, Inc.), an mRNA isolation kit. Levels of HPTPbeta mRNA are determined by Real Time RT-PCR (Applied Biosystems) using TAQMAN™ (Applied Biosystems) gene expression assays and normalized to GAPDH mRNA. The PCR primers and probe used for HPTPbeta amplification hybridize upstream of the predicted sites of AS oligo annealing. Three AS oligos elicited potent inhibition of HPTPbeta mRNA showing an average 73% decrease in HPTPbeta mRNA levels as compared to chemistry matched oligo controls (Antisense oligos available from Sequitur, Inc.—part numbers S17924, S17929, and S17930).

Transfection in HUVEC's is performed with the above-mentioned antisense oligos at a 200 nM final concentration using LIPOFECTIN™ (Invitrogen), a reagent for transfectin of endothelial cells and transfection of DNA or RNA into cell lines, in OPTIMEM™-I (Gibco), a modification of Eagles Minimum Essential Medium, buffered with HEPES and sodium bicarbonate (2.4 g/L) and supplemented with hypoxanthine, thymidine, sodium pyruvate, L-glutamine, trace elements, and growth factors, according to the manufacturers instructions. After a 2-hour transfection, the cells are returned to normal growth media (EGM, Clonetics) and after 48 hours, assayed for VEGFR2 and Tie-2 receptor activity as described in example 4. Uptake efficiency is monitored in every transfection using a fluorescently labeled oligonucleotide and determined to be >90% in every experiment."

Figure 7:
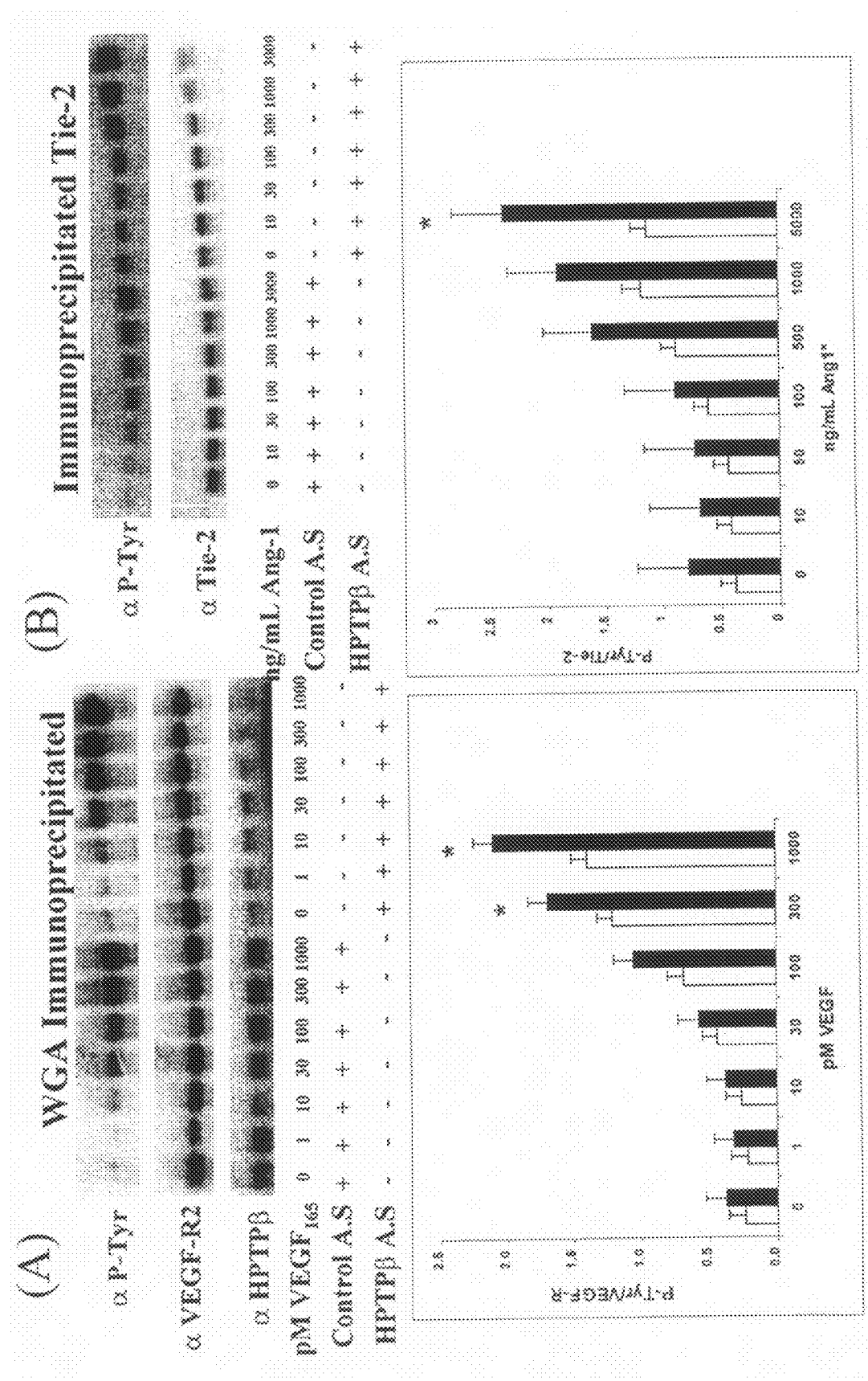
FIG. 7. Antisense "knockdown" of HPTPbeta expression enhances the activation of VEGFR2 and Tie2 in endothelial cells. (A) Western blots of VEGFR2 immunoprecipitates from VEGF stimulated HUVEC's shows a significant increase in the level of VEGFR2 phosphorylation when HPTPbeta protein levels are decreased by 60%. Graph depicts cumulative data from 3 experiments. (B) Western blots and graph showing increased Tie-2 phosphorylation in antisense oligo transfected cells (n=4). (□=control oligo, ■=HPTPbeta antisense oligo) (*=p<0.05).

Results: Western blotting of VEGF stimulated HUVEC's show significant increases in the level of VEGFR2 and Tie-2 phosphorylation when HPTPbeta protein levels are decreased by 60%. (FIG. 7) Taken together, these findings further support the findings in Example 4 and demonstrate that endogenous HPTPbeta can negatively regulate the activation of both Tie-2 and VEGFR2. These findings also demonstrate that the activity of HPTPbeta inhibitors could be measured using a receptor activation assay.

Example 6

Changes in HPTPbeta Expression Modulate VEGF Induced Endothelial Morphogenesis in the Microbead Sprouting Assay Methods: Evaluation of HPTPbeta overexpression in the micro-bead sprouting assay is performed by culturing $2 \times 10^6$ HUVECs with 5 mg of Cytodex beads (Sigma) in 10 ml of EGM (Clonetics) in 100 mm bacteriological dishes for 48 hours. Cell coated beads are transferred to a 50 ml conical tube washed and resuspended in 380 ul D-PBS. Collagen matrix is prepared by adding 71.4 ul of rinsed cell coated beads to 2.8 mL of a collagen matrix solution consisting of 8 volumes of 3 mg/ml rat tail collagen (Sigma) in 0.1% acetic acid, 1 volume of 10× M-199 supplemented with 100 mg/ml L-glutamine, and 1 volume of 10× collagen buffer (0.05N NaOH, 200 mM HEPES, 260 mM NaHCO$_3$). Three hundred and fifty microliters (350 uL) of the mixture is then dispensed immediately into a well on a 24 well tissue culture plate and the matrix was allowed to solidify for 45 minutes at 37° C./5% CO2. Afterwards 1 ml of EGM with or without 50 ng/ml VEGF was added per well and returned to the incubator. After 24 hours, the media was replaced with fresh EGM with or without VEGF (50 ng/ml), correspondingly. Forty-eight hours after matrix formation, a blinded observer visualized the sprouts with a phase contrast inverted microscope and observed 50 beads per well, in quadruplicate wells, for the presence of endothelial cell sprouts. Results are expressed as the number of sprouts per bead. To determine the effect of HPTPbeta overexpression, HUVEC coated beads are infected with an HPTPbeta or GFP adenovirus at 100 MOI in EGM 18 hours before plating in matrix. To evaluate the effects of HPTPbeta knockdown, cells attached to the beads were transfected with 200 nM antisense oligos using Lipofectin (Invitrogen) according to the manufacturers protocol for 2 hours in the original non-coated dish at 37° C./5% CO$_2$ before being introduced to the matrix. The transfected cell coated beads are transferred to a 50 ml conical tube, rinsed once with Dulbecco's phosphate buffered saline (D-PBS, Gibco) and resuspended in 3 ml D-PBS. Fibrin gels are prepared by adding 400 µl of rinsed cell coated beads to 1.6 mL of a matrix solution consisting of 2 mg/mL fibrinogen, 200 U/mL aprotinin and 2.5 U/mL thrombin in D-PBS with or without 10 ng/mL VEGF$_{165}$ (R&D Systems). Four hundred microliters (400 µL) of the beads are then dispensed immediately into a well on a 24 well tissue culture plate and the matrix was allowed to solidify for 10 minutes at 37° C./5% CO$_2$. Afterwards 500 µl of EGM was added per well and returned to the incubator. After 1 hour, the media is replaced with fresh EGM with or without VEGF (10 ng/ml), correspondingly, and again after 24 hours. After 48 hours, a blinded observer visualized the sprouts as described above.

Figure 8:
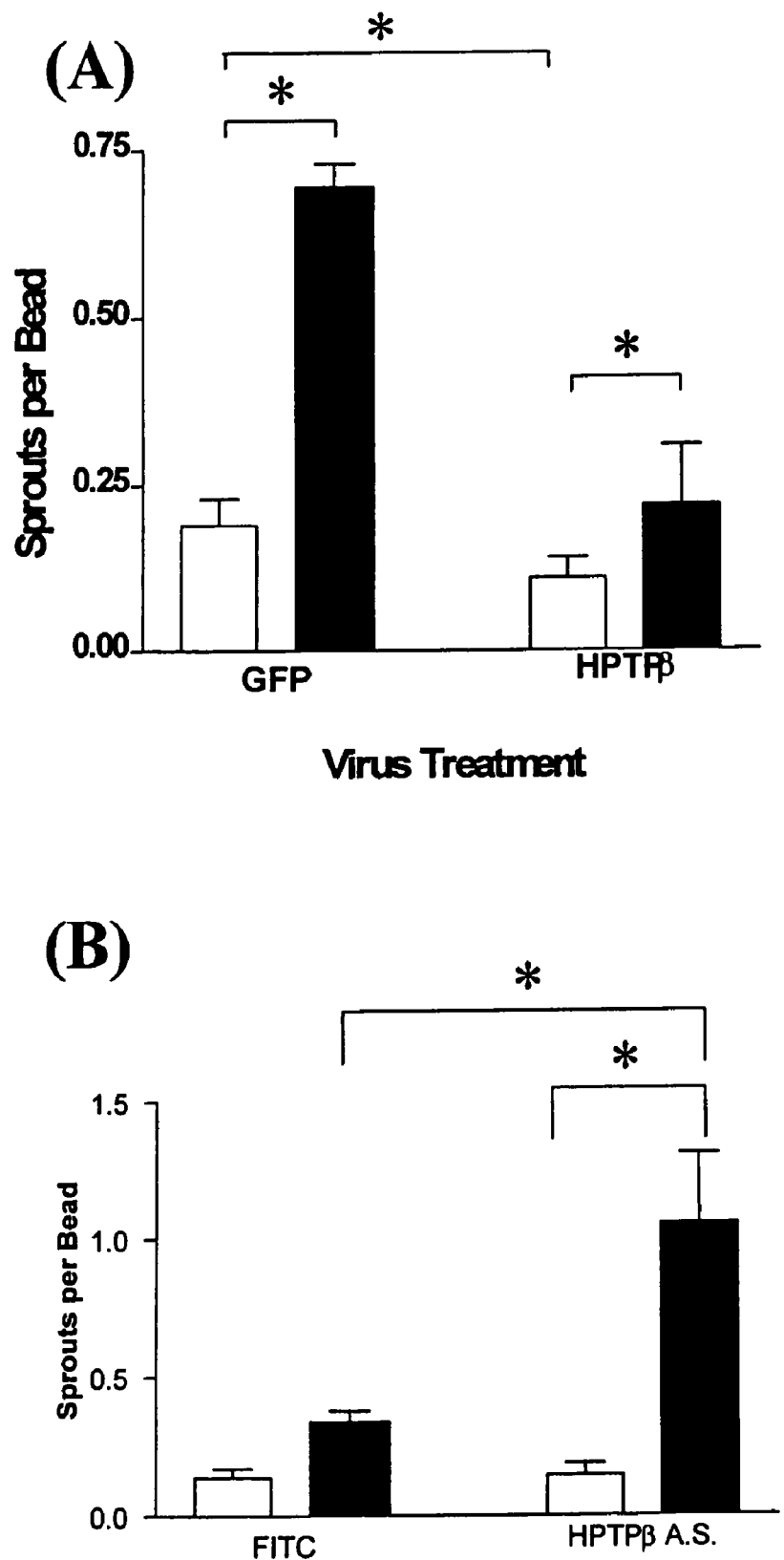
FIG. 8. Altering HPTPbeta expression in HUVECs using adenovirus overexpression or antisense knockdown modulates VEGF-mediated capillary morphogenesis in the endothelial cell bead sprouting assay. (A) HPTPbeta overexpression decreases VEGF-induced sprouting. HPTPbeta and GFP infected HUVECs are incubated in the presence (■) or absence (□) of VEGF$_{165}$. (B) Antisense knockdown of HPTPbeta enhances VEGF induced endothelial cell sprouting.

Results: HPTPbeta overexpression decreases VEGF-induced sprouting as compared to GFP infected controls in HUVEC's (FIG. 8A). Conversely, antisense knockdown of HPTPbeta enhances VEGF induced endothelial cell sprouting (FIG. 8B). These findings confirm the regulation of VEGFR2 by HPTPbeta in examples 4 and 5 and demonstrate that the angiogenic activity of VEGFR2 is modulated by HPTPbeta in parallel with receptor activation. These findings also demonstrate that this assay could be used to measure the effect of HPTPbeta inhibitors on endothelial cell sprouting in the absence or presence of additional growth factor.

Example 7

Adenoviral-mediated Overexpression of HPTPbeta Attenuates Angiogenesis in the Rat Aortic Ring Explant Assay Methods: The isolated rat aortic ring model of angiogenesis is performed using the thoracic aorta from 150-175 gram, male Sprague-Dawley rats (Charles River). The excised thoracic aorta is placed in sterile saline solution and transferred to endothelial basal media (EBM, Clonetics) containing 1% antibiotics/antimycotic (Gibco BRL). Periadventitial fibroadipose tissue and any visible blood clots were removed. Aortas are cross-sectioned at ~1 mm intervals and the resulting tissues placed in 100 µl of Dulbecco's Modified Eagle Medium (DMEM) containing 2% FBS, in the presence or absence of adenovirus for green fluorescent protein, empty virus or HPTPbeta (all at $1.0 \times 10^{11}$ virus particles/ml), as described. Rings are incubated for 30 minutes at 37° C. in a humidified incubator under a constant 5% CO$_2$ atmosphere. Following adenoviral infection, aortic rings were washed with EBM and placed in a 24-well tissue culture plate. Aortic rings are overlaid with 450 µl of collagen solution consisting of 8 volumes of 3 mg/ml rat tail collagen (Sigma) in 0.1% acetic acid, 1 volume of 10× M-199 supplemented with 100 mg/ml L-glutamine, and 1 volume of 10× collagen buffer (0.0SN NaOH, 200 mM HEPES, 260 mM NaHCO$_3$). The collagen solution is allowed to solidify for 1 hour and covered with 1 ml of EBM. Images (TIFF) are taken using a SPOT camera connected to a Nikon inverted microscope and analyzed (vessel extent and area) using automated image analysis software.

Figure 9:
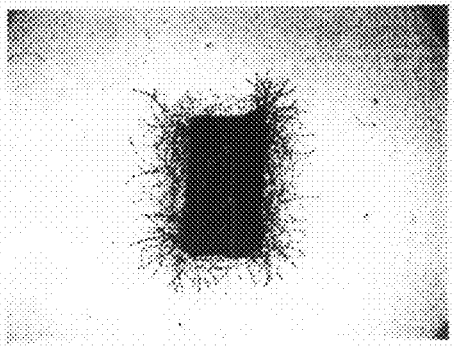
FIG. 9. Overexpression of HPTPbeta attenuates angiogenesis in the rat aortic ring explant assay. (A) Rat thoracic aortic rings are infected with empty virus, GFP containing virus or HPTPbeta containing virus and compared to uninfected rings. Representative images are shown for each group. (B) Quantitation of vessel extent and area indicate a significant reduction in both parameters only in HPTPbeta infected rings. Data are from 4-5 rings in each group. All viruses are administered at 1×10$^{11}$ virus particles/ml. Abbreviations: Basal—Uninfected; EV—rings infected with an empty adenoviral vector; GFP—rings infected with adenovirus encoding green fluorescent protein; HPTPbeta—rings infected with adenovirus encoding HPTPbeta. *P<0.001 vs. Basal, GFP, EV, One-way ANOVA, followed by Tukey's Multiple Comparison Test.
Figure 9:
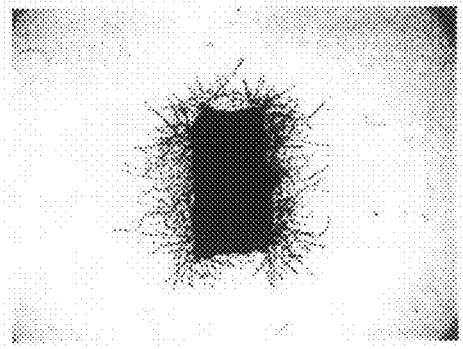
Figure 9:
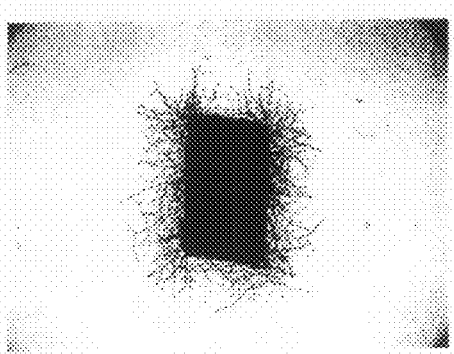
Figure 9:
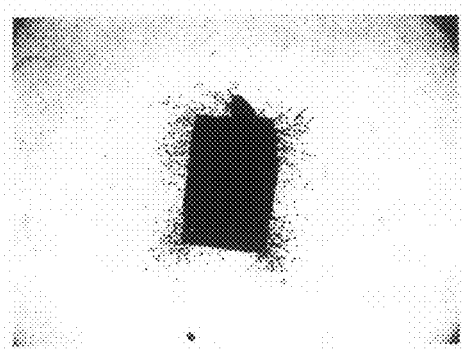
Figure 9:
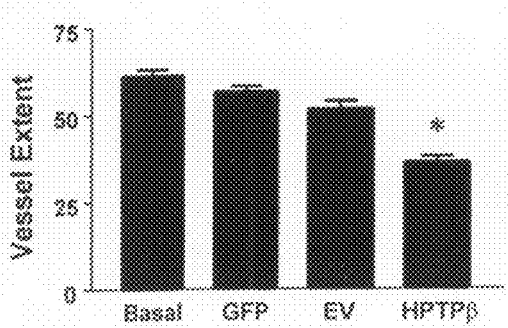
Figure 9:
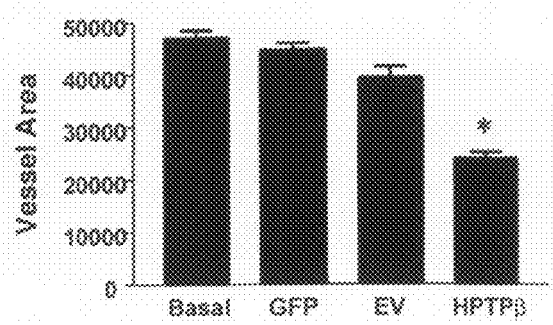

Results: Rat thoracic aortic rings are infected with empty virus, GFP containing virus or HPTPbeta containing virus showed that the parameters of vessel extent and area were significantly reduced in HPTPbeta infected rings (FIG. 9). These data demonstrate that HPTPbeta can negatively regulate blood vessel formation in a model that has been shown to be dependent on VEGFA.

Example 8

Figure 10:
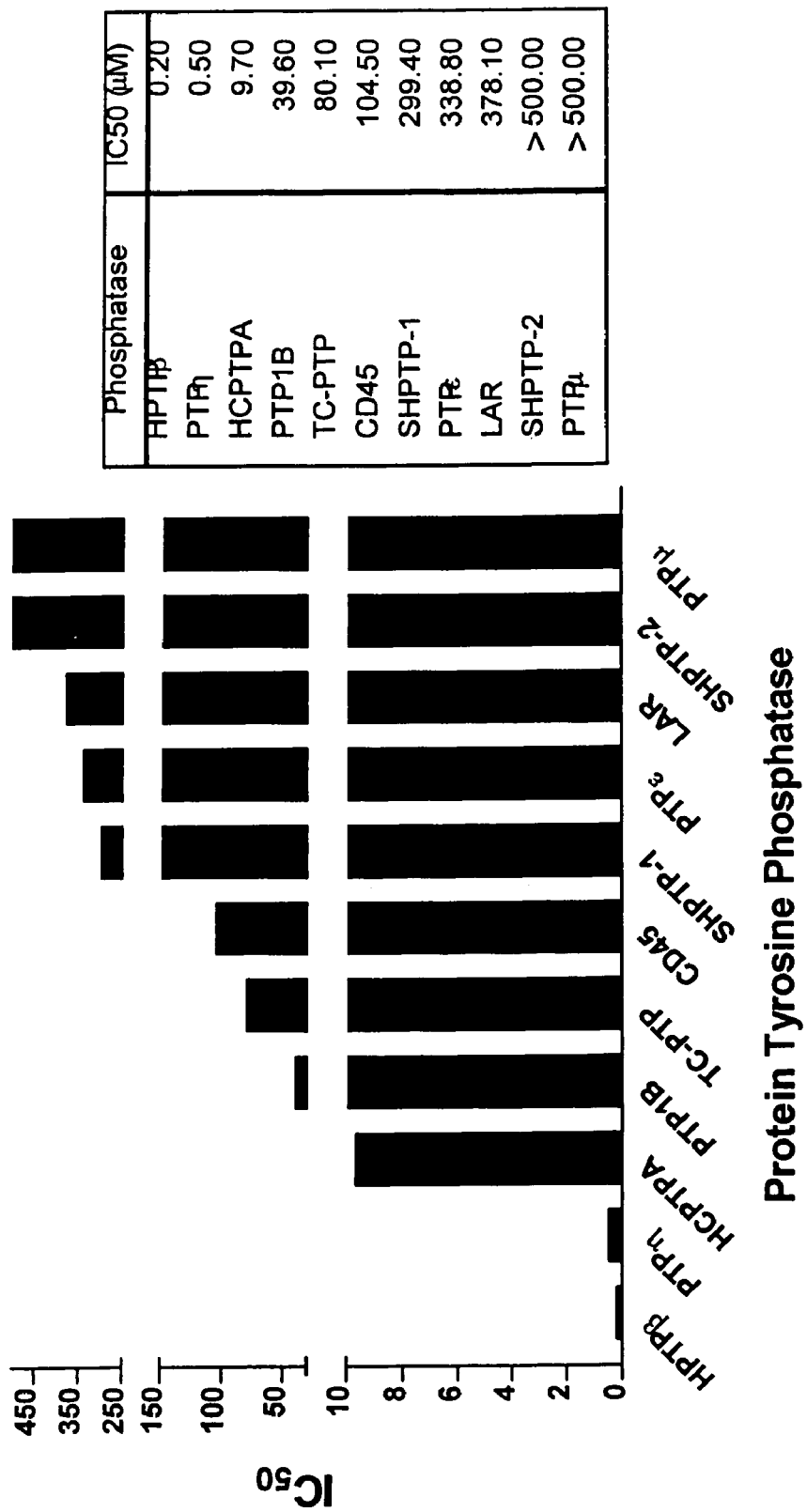
FIG. 10. Compound 1 ((R)-[1-Methylcarbamoyl-2-(4-sulfoamino-phenyl)-ethyl]-carbamic acid tert-butyl ester) is a selective HPTPbeta inhibitor. Compound 1 was assayed for inhibition of a panel of recombinant phosphatases essentially as described in Example 2 for HPTPbeta. This compound was at least 10 fold selective for HPTPbeta over the other phosphatases tested except for the closely related HPTPeta.

A selective HPTPbeta inhibitor (Compound 1 ((R)-[1-Methylcarbamoyl-2-(4-sulfoamino-phenyl)-ethyl]-carbamic Acid tert-butyl ester) Enhances the Ligand-induced VEGR2 and Tie2 Receptor Auto-phosphorylation Methods: The potency of a class of HPTPbeta inhibitors was optimized by iterative screening for inhibition of HPTPbeta activity measured as described in Example 2. This iterative screening process resulted in the discovery of a nanomolar HPTPbeta inhibitor. To determine selectivity, compound 1 was tested against a panel of several other recombinant phosphatases (FIG. 10). VEGFR2 and Tie-2 receptor activation was assayed as mentioned in example 4. However, to assess the effect of the HPTPbeta inhibitor, the cells were pretreated for 30 minutes prior to stimulation with either 0.1 mM or 1 mM Compound 1 in Opti-MEM media (Invitrogen) at 37° C./5% $CO_2$.

Figure 11:
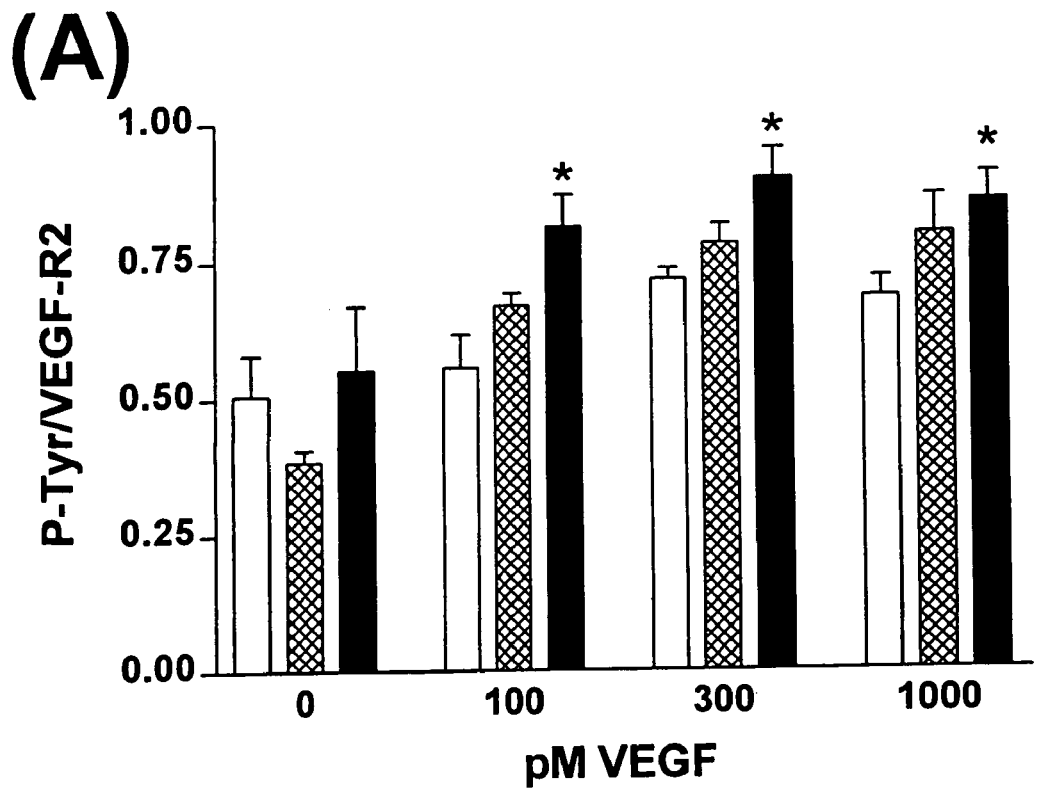
FIG. 11. A selective HPTPbeta inhibitor enhances ligand-induced phosphorylation of VEGFR2 and Tie2. Endothelial cells pretreated for 30 minutes with either 0.1 mM (▣) or 1 mM (■) Compound 1 show increased ligand stimulated tyrosine phosphorylation of the VEGFR2 (A) and Tie-2 (B) receptors compared to vehicle treated controls (□) as measured by anti-phosphotyrosine western blotting. *=p<0.05.
Figure 11:
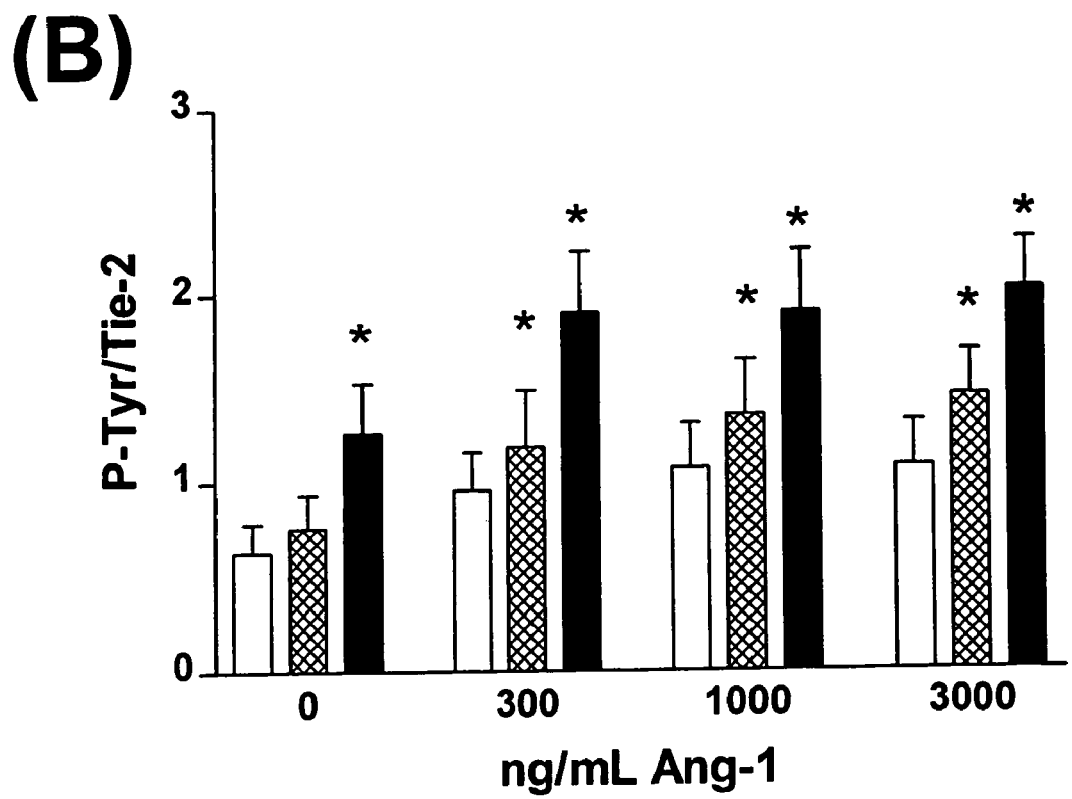

Results: A potent and selective HPTPbeta inhibitor (Compound 1) was developed (see Example 11) as an agent to enhance the activation of VEGFR2 and Tie2 (FIG. 10). Compound was at least 10 fold selective for HPTPbeta versus the any of the other phosphatases except for the closely related HPTPeta. As seen in FIG. 11, anti-phosphotyrosine western blotting revealed an increase in VEGFR2 and Tie-2 receptor activation following a 30-minute pre-treatment with a small molecule inhibitor of HPTPbeta. Clearly, these assays could be used to optimize the potency and selectivity and to test the efficacy of other HPTPbeta inhibitors.

Example 9

A Selective HPTPbeta Inhibitor Increases Ligand Induced Endothelial Cell Survival Methods: Human umbilical vein endothelial cells (HUVEC, Clonetics) were seeded at 10,000/well in a 96-well plate for 2 hours in EGM media (Clonetics). The cells were then serum-deprived for 2 hours in DMEM (Invitrogen) supplemented with 0.2% bovine serum albumin. Quadruplicate wells were then treated with either vehicle or 500 µM Compound in the presence or absence of either 500 pM recombinant human $VEGF_{165}$ or 250 ng/mL recombinant human Angiopoietin-1 (Ang-1) (R&D Systems) for 72 hours in DMEM supplemented with 0.2% bovine serum albumin. Cells remaining after incubation were detected using the CellTiter-Glo™ System according to the manufacturers instructions (Promega) and measured using a Victor V plate reader (Perkin Elmer/Wallac).

Figure 12:
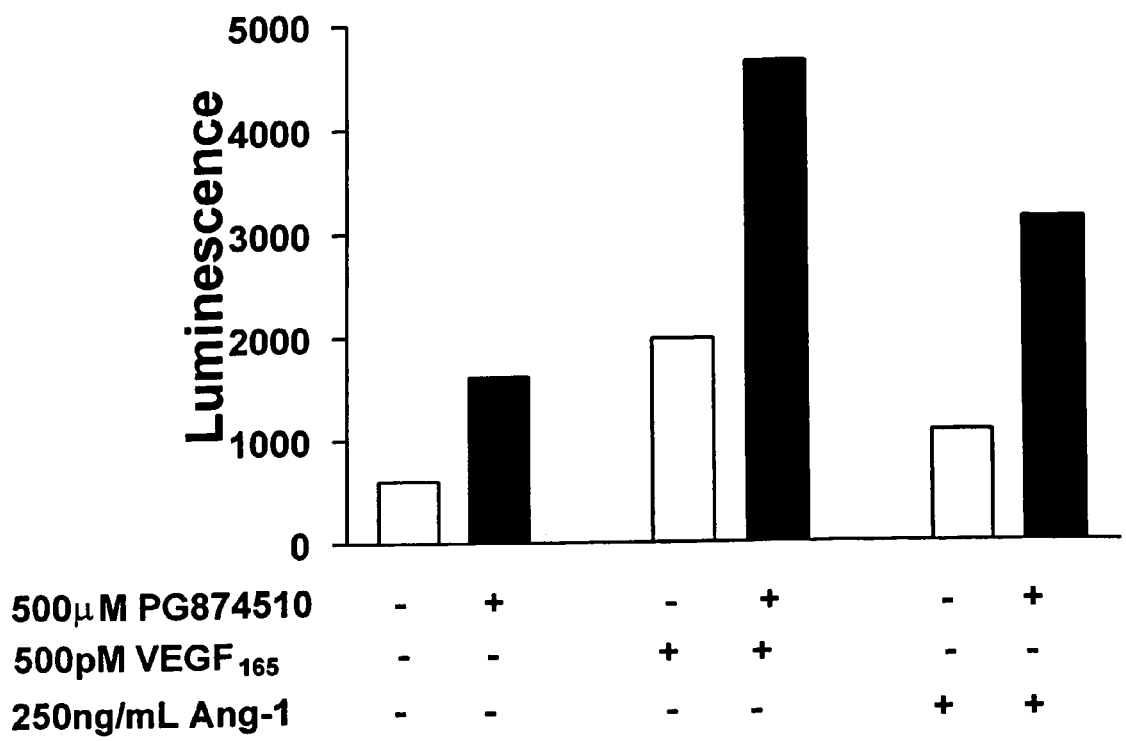
FIG. 12. A selective HPTPbeta inhibitor enhances VEGF and Angiopoietin-1 (Ang-1) mediated endothelial cell survival. Endothelial cells treated with 500 μM of the HPTPbeta inhibitor Compound 1 (■) show increased cell survival when stimulated with 500 pM $VEGF_{165}$ or 250 ng/mL Ang-1 compared to vehicle treated controls (□).

Results: As seen in FIG. 12, endothelial cells treated with 500 µM of the HPTPbeta inhibitor Compound show increased cell survival when stimulated with 500 µM $VEGF_{165}$ or 250 ng/mL Angiopoietin-1 (Ang-1). Interestingly, Compound 1 also increased basal levels of survival over untreated controls.

Example 10

A small Molecule Inhibitor of HPTPbeta Increases in vascular Sprouting in the Ex-vivo Rat Aortic Ring Model Methods: The rat aortic ring model was essentially performed as described in example 7 with the exception that increasing concentrations of Compound 1 was added to the final 1 L of EBM added on top of the solidified collagen mixture and was present for the remainder of the experiment.

Figure 13:
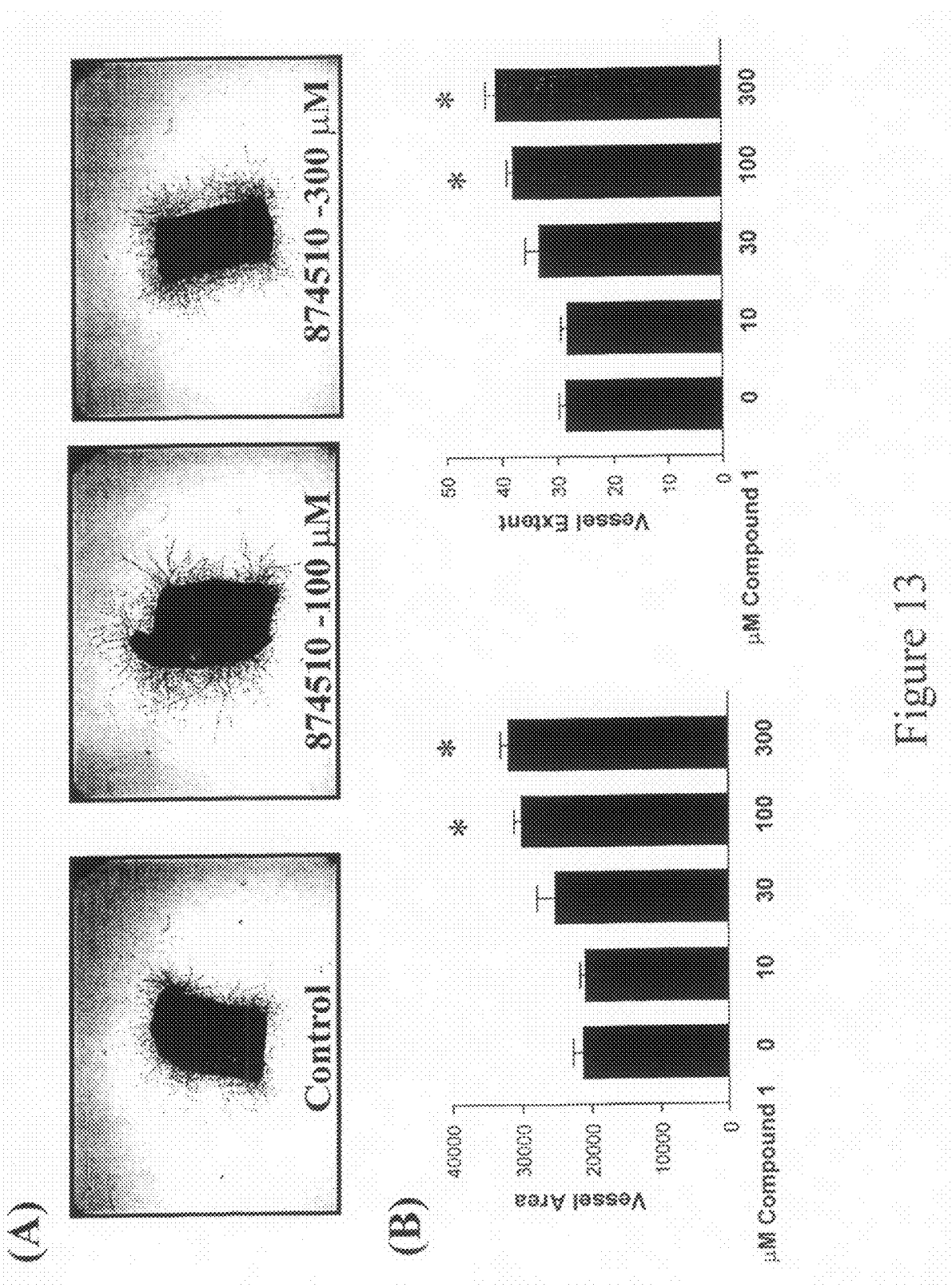
FIG. 13. A selective HPTPbeta inhibitor enhances angiogenesis in the rat aortic ring explant assay. Rat thoracic aortic rings were treated at the time of plating with increasing concentrations of a small molecule inhibitor of HPTPbeta. Representative pictures show increased sprouting in the rings treated with 100 μM and 300 μM Compound 1 (A). Graphed data from 8 quantitated pictures per treatment show significant increases in the parameters of vessel extent and area with 100 μM and 300 μM Compound 1 (B). *=p<0.05 vs. control.

Results: Rat thoracic aortic rings treated at the time of plating with increasing concentrations of a small molecule inhibitor of HPTPbeta demonstrate significant increases in the parameters of vessel extent and area with 100 µM and 300 µM Compound 1 (FIG. 13).

Example 11

Synthesis of Compound 1 ((R)-[1-Methylcarbamoyl-2-(4-sulfoamino-phenyl)-ethyl]-carbamic acid tert-butyl ester)

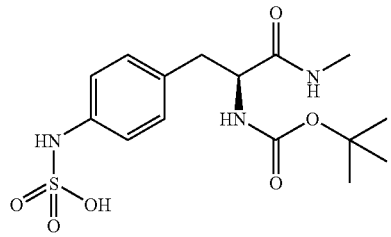

Compound 1 ((R)-[1-Methylcarbamoyl-2-(4-sulfoamino-phenyl)-ethyl]-carbamic acid tert-butyl ester)

Boc-Phe(4-$NO_2$)—NMe: Boc-Phe(4-$NO_2$)—OH (10.0 g, 32.3 mmol) is dissolved in anhydrous tetrahydrofuran (32.2 mL) with 4-methylmorpholine (3.90 mL, 35.4 mmol). Isobutylchloroformate (4.18 mL, 32.3 mmol) is dropwise added at 0° C. and the mixture is stirred for 1 hr. at 0° C. Methylamine (332.3 mL, 2.0 M in tetrahydrofuran) is added dropwise at 0° C. and the mixture is stirred for 18 hr. at room temperature. The mixture is then recrystallized from 1:1 DCM:methanol to give 6.69 g pure white solid.

Boc-Phe(4-$NH_2$)—NMe: Boc-Phe(4-$NO_2$)—NMe (500 mg, 1.55 mmol) is dissolved in methanol (10 mL). To this was added palladium on carbon (10% by weight, 50 mg). The reaction is placed under a hydrogen atmosphere until reaction is complete (tlc). The catalyst is removed by filtration and the filtrate is concentrated to provide the amine, which is used without purification.

(R)-[1-Methylcarbamoyl-2-(4-sulfoamino-phenyl)-ethyl]-carbamic acid tert-butyl ester: In a dry flask 0.420 g of the aniline compound is dissolved in 2 mL pyridine. To this solution is added 0.684 g of sulfurtrioxide-pyridine complex. The mixture is stirred 5 minutes then diluted with 25 mL of 7% ammonium hydroxide. The mixture is evaporated down to an off-white solid and purified to provide 0.106 g of product as its ammonium salt. $^1H(D_2O)$: δ 7.04 (s, 4H), 4.07-4.05 (m, 1H), 2.92-2.68 (m, 2H) 2.55 (s, 3H), 1.24 (s, 9H)

Miscellaneous

Except as otherwise noted, all amounts including quantities, percentages, portions, and proportions, are understood to be modified by the word "about", and amounts are not intended to indicate significant digits.

Except as otherwise noted, the articles "a", "an", and "the" mean "one or more".

All documents cited are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A pharmaceutical composition, comprising:
   a) an effective amount of (R)-[1-methylcarbamoyl-2-(4-sulfoaminophenyl)ethyl]-carbamic acid tert-butyl ester; and
   b) a pharmaceutically-acceptable carrier.

2. A pharmaceutical composition for modulating an angiogenesis mediated disorder, comprising:
   a) about 500 µM of (R)-[1-methylcarbamoyl-2-(4-sulfoaminophenyl)ethyl]-carbamic acid tert-butyl ester; and
   b) a pharmaceutically-acceptable liquid carrier.

3. The composition according to claim 2, wherein the angiogenesis mediated disorder is selected from disorders, diseases, and/or unwanted conditions characterized by a wanted increase in angiogenesis or characterized by reduced angiogenesis selected from the group consisting of skeletal muscle ischemia, myocardial ischemia, stroke, coronary artery disease, peripheral vascular disease, and tissue repair where tissue has been damaged by trauma, surgical procedures, irradiation, laceration, toxic chemicals, viral infection, bacterial infection, non-healing wounds, or burns, or where tissue has been damaged by arthritis or osteoporosis.

4. The composition according to claim 2, wherein the angiogenesis mediated disorder is tissue ischemia.

* * * * *